United States Patent [19]

Tachibana et al.

[11] Patent Number: 4,873,183
[45] Date of Patent: Oct. 10, 1989

[54] SILVER HALIDE COLOR PHOTOGRAPHIC LIGHT-SENSITIVE MATERIAL CONTAINING PYRAZOLOAZOLE TYPE CYAN COUPLER

[75] Inventors: Kimie Tachibana, Hino; Yutaka Kaneko, Sagamihara; Fumio Ishii, Akishima, all of Japan

[73] Assignee: Konica Corporation, Tokyo, Japan

[21] Appl. No.: 291,351

[22] Filed: Dec. 29, 1988

Related U.S. Application Data

[63] Continuation of Ser. No. 124,987, Nov. 24, 1987, abandoned.

[30] Foreign Application Priority Data

| Nov. 25, 1986 | [JP] | Japan | 61-280164 |
| Dec. 27, 1986 | [JP] | Japan | 61-313455 |
| Mar. 2, 1987 | [JP] | Japan | 62-47323 |
| Mar. 9, 1987 | [JP] | Japan | 62-53417 |
| Mar. 17, 1987 | [JP] | Japan | 62-62162 |
| Mar. 17, 1987 | [JP] | Japan | 62-62163 |
| Jul. 23, 1987 | [JP] | Japan | 62-184552 |

[51] Int. Cl.[4] .............................. G03C 7/38
[52] U.S. Cl. ..................... 430/550; 430/384; 430/385; 430/558
[58] Field of Search ............. 430/384, 385, 558 R, 430/550

[56] References Cited

U.S. PATENT DOCUMENTS

| 3,369,897 | 2/1968 | Menzel et al. | 430/558 |
| 3,725,067 | 4/1973 | Bailey et al. | 430/558 |
| 4,639,415 | 1/1987 | Kaneko et al. | 430/558 |
| 4,704,350 | 11/1987 | Morigaki et al. | 430/558 |
| 4,741,995 | 5/1988 | Tani et al. | 430/558 |

*Primary Examiner*—Richard L. Schilling
*Attorney, Agent, or Firm*—Finnegan, Henderson, Farabow, Garrett, & Dunner

[57] ABSTRACT

A light-sensitive silver halide color photographic material comprising a support and, provided thereon, a red light-sensitive silver halide emulsion layer containing a novel pyrazoloazole type cyan dye-forming coupler having at least one electron attractive group at a substitutable position except the active site of the coupler for coupling reaction.

11 Claims, 4 Drawing Sheets

SILVER HALIDE COLOR PHOTOGRAPHIC LIGHT-SENSITIVE MATERIAL CONTAINING PYRAZOLOAZOLE TYPE CYAN COUPLER

This application is a continuation of application Ser. No. 124,987, filed Nov. 24, 1987, now abandoned.

FIELD OF THE INVENTION

This invention relates to a silver halide color photographic light-sensitive material containing a novel cyan dye-forming coupler and more particularly to a silver halide color photographic light-sensitive material containing a cyan dye-forming coupler excellent in spectral absorption characteristics.

BACKGROUND OF THE INVENTION

A color image is formed by exposing a silver halide photographic light-sensitive material to light and then treating the light-sensitive material in a color development process in which an oxidized aromatic primary amine color developing agent is reacted with a dye-forming coupler (this term will sometimes be referred to simply as coupler) so as to form a dye.

Generally, to the above-mentioned photographic process, a color reproduction method using a color subtraction technique is applied, so that color images in yellow, magenta and cyan may be formed, respectively.

As for the cyan color image dye-forming couplers, phenols or naphthols have popularly been used so far.

From the viewpoint of color reproduction, however, cyan images obtained from phenols or naphthols have had serious problems. Namely, there have been the poor sharpness of spectral absorption on the short wavelength side as well as an undesirable absorption, i.e., an irregular absorption, in green spectral region. The present situation is that, with a negative light-sensitive material, therefore, it cannot help masking or taking some measure to remedy the irregular absorption; and with a paper light-sensitive material, there have not been any remedying measures, but the color reproducibility thereof has considerably been worsened.

With dye images obtained from phenols and naphthols having so far been used, there have still been several unsolved problems in their preservability. For example, the dye images obtained from 2-acylaminophenol cyan coupler described in U.S. Pat. Nos. 2,367,531 and 2,423,730 are generally poor in fastness against heat; the dye images obtained from 2,5-diacylaminophenol cyan coupler described in U.S. Pat. Nos. 2,369,929 and 2,772,162 are generally poor in fastness against light; and dye images obtained from 1-hydroxy-2-naphthamide cyan coupler are generally poor in fastness against both light and heat. They have therefore been unsatisfactory.

Also, with 2,5-diacylaminophenol cyan couplers described in U.S. Pat. No. 4,122,369, Japanese Patent Publication Open to Public Inspection (hereinafter called Japanese Patent O.P.I. Publication) Nos. 155538-1982 and 157246-1982, and so forth, and 2,5-diacylamino phenol cyan coupler having a hydroxy group in the ballast portion thereof described in U.S. Pat. No. 3,880,661, each of them has still been unable to reach a satisfactory level, from the viewpoints of the fastness against light and heat and yellow-stain prevention.

SUMMARY OF THE INVENTION

It is, therefore, an object of the invention to provide a silver halide color photographic light-sensitive material containing a novel cyan-dye forming coupler.

Another object of the invention is to provide a silver halide color photographic light-sensitive material in which the above-mentioned defects of the cyan couplers having been used so far are improved, namely, the spectral absorption thereof is sharp and the absorption in the green spectral region is reduced, so that a clear cyan image excellent in spectral absorption characteristics can be formed.

A further object of the invention is to provide a silver halide color photographic light-sensitive material capable of forming a cyan image without causing any change in hue against hear and moisture.

A still further object of the present invention is to provide a light-sensitive silver halide photographic material containing a novel cyan dye-forming coupler which has an improved dispersion stability especially in the storage in the cooled condition.

The above-mentioned objects of the invention can be accomplished with a silver halide color photographic light-sensitive material comprising a support bearing thereon at least one red-light-sensitive silver halide emulsion layer containing a pyrazoloazole type cyan dye-forming coupler having at least one electron withdrawing (or attracting) group in a substitutable position excluding the active site of the coupler.

DETAILED DESCRIPTION OF THE INVENTION

Figure 1:
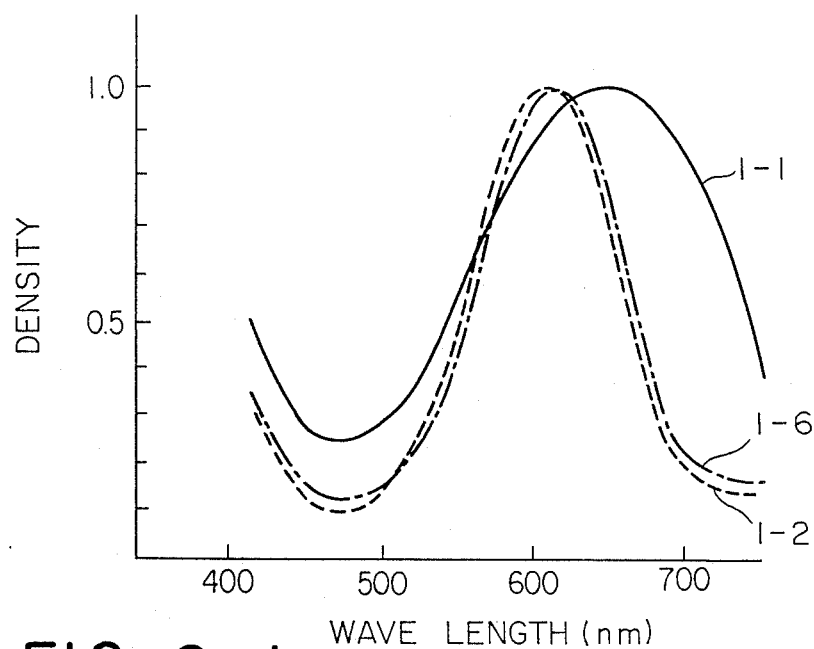
FIGS. 1-1 to 7-1 show the curves of absorption spectra of the processed samples of the present invention and ones for comparison.

According to the preferable embodiment of the present invention, the cyan dye-forming coupler of the present invention is represented by following Formula [I]-1:

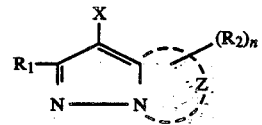

Formula [I]-1 wherein at least one group, selected from the group consisting of $R_1$ and at least one of a plurality of $R_2$, is an electron withdrawing group; Z represents a group of non-metal atoms required for completing a nitrogen-containing heterocyclic ring; each of $R_2$s is bonded to the carbon atom of the heterocyclic ring; X represents a hydrogen atom or a substituent capable of splitting off upon reaction with the oxidized product of a color developing agent; and n is an integer of 1 or 2.

The spectral absorption maximum of the cyan dye-forming coupler of the present invention in the visible wavelength region is between 580 to 710 nm, and more preferably within the range between 600 to 700 nm.

Now, the invention will be described in detail.

According to one of the preferable embodiments of the invention, the cyan dye-forming coupler is represented by the above-given Formula [I]-1.

In Formula [I]-1, the electron withdrawing groups, which are represented by at least one group selected from the group consisting of $R_1$ and at least one $R_2$, are preferably the substituents having a substituent constant σp (defined by Hammett) of not less than +0.20. They include, typically, each group of carbamoyl, acyl, acyloxy, oxycarbonyl, halogenated alkyl, halogenated aryl, carboxyl, cyano and so forth.

The carbamoyl groups may be substituted by an alkyl group, an aryl group (preferably, a phenyl group), or the like.

The acyl groups include, for example, an alkylcarbonyl group, an arylcarbonyl group and so forth.

The acyloxy groups include, preferably, an alkylcarbonyloxy group and so forth.

The oxycarbonyl groups include, for example, an alkoxycarbonyl group, an aryloxycarbonyl group, and so forth.

The halogenated alkoxy groups include, preferably, a 1-halogenated alkoxy group.

The halogenated aryloxy groups include, preferably, a tetrafluoroaryloxy group, a pentafluoroaryloxy group, and so forth.

The halogenated alkyl groups preferably used include, for example, a trifluoromethyl group, a heptafluoroisopropyl group, a nonylfluoro(t)butyl group and so forth.

The halogenated aryl groups preferably used include, for example, a tetrafluorophenyl group, a pentafluorophenyl group and so forth.

Besides the above-given substituents, an alkylsulfonylmethyl group, an arylsulfonylmethyl group and so forth may also preferably be used.

The above-given substituents are allowed to have a further substituent including ballast groups such as a long-chained hydrocarbon group, a polymer residual group and so forth; substituents such as an electron withdrawing group; and so forth.

When $R_1$ or $R_2$ is a substituent other than the above-mentioned electron withdrawing groups, $R_1$ or $R_2$ may be either a hydrogen atom or any of substituents including, typically, each group of alkyl, aryl, anilino, acylamino, sulfonamido, alkylthio, arylthio, alkenyl, cycloalkyl and so forth and, in addition to the above, each group of cycloalkenyl, alkinyl, heterocyclic ring, alkoxy, aryloxy, heterocyclic-oxy, siloxy, carbamoyloxy, amino, alkylamino, imido, ureido, sulfamoylamino, carbonylamino and heterocyclic-thio; a spiro compound residual group; a cross-linked hydrocarbon compound residual group; and so forth.

The alkyl groups represented by $R_1$ may preferably be those having 1 to 32 carbon atoms and may be either straight chained or branched.

The aryl groups represented by $R_1$ include, preferably, a phenyl group.

The acylamino groups represented by $R_1$ include, for example, an alkylcarbonylamino group, an arylcarbonylamino group and so forth.

The sulfonamido groups represented by $R_1$ include, for example, an alkylsulfonylamino group, an arylsulfonylamino group and so forth.

In the alkylthio groups and the arylthio groups each represented by $R_1$, the alkyl component and aryl component thereof include, for example, the alkyl groups and aryl groups each represented by the above $R_1$, respectively.

The alkenyl groups represented by $R_1$ may preferably be those having 2 to 32 carbon atoms, and the cycloalkyl groups may be those having 3 to 12 carbon atoms preferably and those having 5 to 7 carbon atoms more preferably. The alkenyl groups may be either straight chained or branched.

The cycloalkenyl groups represented by $R_1$ may be those having 3 to 12 carbon atoms preferably and those having 5 to 7 carbon atoms more preferably.

The carbamoyloxy groups include, for example, an alkylcarbamoyloxy group, an arylcarbamoyloxy group and so forth;

The ureido groups include, for example, an alkylureido group, an arylureido group and so forth;

The sulfamoylamino groups include, for example, an alkylsulfamoylamino group, an arylsulfamoylamino group and so forth;

The heterocyclic groups may preferably be the 5- to 7-membered and they include typically a 2-furyl group, a 2-thienyl group, a 2-pyrimidinyl group, a 2-benzothiazolyl group and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth;

The imido groups include, for example, a succinimido group, a 3-heptadecylsuccinimido group, a phthalimido group, a glutarimido group and so forth;

The spiro compound residual groups include, for example, a spiro [3,3] heptane-1-yl and so forth;

The cross-linked hydrocarbon compound residual groups include, for example, a bicyclo [2,2,1] heptane-1-yl, a tricyclo [3,3,1,1$^{37}$]decane-1-yl, a 7,7-dimethylbicyclo [2,2,1] heptane-1-yl and so forth; and The carbonylamino groups include, for example, an alkoxycarbonylamino group, an aryloxycarbonylamino group and so forth.

The above-given groups are allowed to have such a ballast group as a long-chained hydrocarbon group, a polymer residual group and so forth, to serve as a substituent.

The substituents represented by X, which are capable of splitting off upon reaction with the oxidized product of a color developing agent, include, for example, a halogen atom such as a chlorine atom, a bromine atom, a fluorine atom and so forth and each of the groups including alkoxy, aryloxy, heterocyclic-oxy, acyloxy, sulfonyloxy, alkoxycarbonyloxy, aryloxycarbonyl, alkyloxalyloxy, alkoxyoxalyloxy, alkylthio, arylthio, heterocyclic-thio, alkyloxythiocarbonylthio, acylamino, sulfonamido, nitrogen-containing heterocyclic ring bonded to an N atom, alkyloxycarbonylamino, aryloxycarbonylamino, carboxyl,

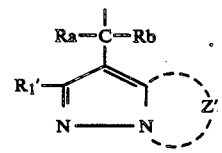

wherein R₁' and Z' are synonymous with the aforegiven R₁ and Z, respectively; and Ra and Rb each represent a hydrogen atom, an aryl group, an alkyl group or a heterocyclic group; and so forth; and among them, a halogen atom and particularly a chlorine atom are preferable.

The nitrogen-containing heterocyclic rings completed by either Z or Z' include, for example, a pyrazole ring, an imidazole ring, a triazole ring or the like.

According to another one of the preferable embodiments of the invention, the cyan dye-forming coupler is one represented by the following Formula [I]-2:

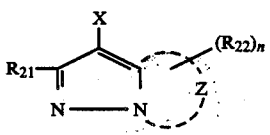

Formula [I]-2 wherein Z represents a group of non-metal atoms required for completing a nitrogen-containing heterocyclic ring; X represents a hydrogen atom or a substituent capable of splitting off upon reaction with the oxidized product of a color developing agent; $R_{21}$ represents an electron withdrawing group; $R_{22}$ represents a hydrogen atom or a substituent; and n is an integer of 1 or 2.

The couplers represented by the above-given Formula [I]-2 relating to the invention are characterized by having the electron withdrawing group in the pyrazolo portion of the pyrazoloazole nucleus of the coupler.

The electron withdrawing groups, which are represented by $R_{21}$ are preferably the substituents having a $\delta\rho$ value of +0.20 in quantitative structural active relation defined in Hansch method. They include, typically, a halogen atom and each group of nitro, cyano, acyloxy, halogenated alkyl, halogenated alkoxy, sulfonyl, carboxyl, sulfonyloxy, sulfinyl, sulfamoyl, phosphonyl, pyrrole, tetrazolyl, acyl, carbamoyl, oxycarbonyl and so forth.

For example, the halogen atoms represente by $R_{21}$ include, a fluorine atom, a chlorine atom, a bromine atom and so forth.

The acyloxy groups represented by $R_{21}$ include each group of acetyloxy, 2-chloroacetyloxy, benzoyloxy and so forth.

The halogenated alkyl groups represented by $R_{21}$ include, each group od trifluoromethyl, 2-chloroethyl and so forth.

The sulfonyl groups represented by $R_{21}$ include each group of methyl sulfonyl, trifluoromethyl sulfonyl, benzene sulfonyl, p-toluene sulfonyl and so forth.

The sulfonyloxy groups include each group of methyl sulfonyloxy, trufluoromethyl sulfonyloxy, benzene sulfonyloxy and so forth.

The sulfinyl groups include methyl sulfinyl, octyl sulfinyl, 3-phenoxybutyl sulfinyl, m-pentadecylphenyl sulfinyl and so forth.

The sulfamoyl groups include each group of N,N-dipropyl sulfamoyl, N-phenyl-N-methyl sulfamoyl, N,N-diethyl sulfamoyl, N-ethyl-N-dodecyl sulfamoyl and so forth.

The phoshonyl groups include each group of ethoxy phosphonyl, butoxy phosphonyl, phenoxy phosphonyl and so forth.

The tetrazolyl groups include each group of 1-tetrazolyl, 5-chloro-1-tetrazolyl and so forth.

The halogenated alkoxy groups include each group of trifluoromethoxy and so forth.

The acyl groups include each group of acetyl, dodecanoyl, benzoyl, p-chlorobenzoyl and so forth.

The carbamoyl groups include each group of N,N-dibutyl carbamoyl, N-ethyl-N-dodecyl carbamoyl and so forth.

The oxycarbonyl groups include each group of alkoxycarbonyl such as ethoxycarbonyl, aryloxycarbonyl such as phenoxycarbonyl, and so forth.

Besides the above-given electron withdrawing groups, each group of fluoroalkylamido, trifluoropropynyl, carboxyethenyl, dicyanoethenyl, trifluoromethane sulfenyl, thiocyanate, isothiocyanate and so forth may also be included.

The above-given groups are also allowed to have a substituent such as a ballast group or an electron withdrawing group.

The substituents represented by $R_{22}$ include, typically, each of group of alkyl, aryl, anilino, acylamino, sulfonamido, alkylthio, arylthio, alkenyl, cycloalkyl and so forth. Besides the above, they also include each group of cycloalkenyl, alkinyl, heterocyclic, alkoxy, aryloxy, heterocyclic-oxy, siloxy, carbamoyloxy, amino, alkylamino, imido, ureido, sulfamoylamino, alkoxycarbonylamino, aryloxycarbonylamino, alkoxycarbonyl, aryloxycarbonyl and heterocyclic-thio, as well as a spiro-compound residual group, a cross-linked hydrocarbon compound residual group and so forth.

The alkyl groups represented by $R_{22}$ preferably include those having 1 to 32 carbon atoms and they may be straight-chained or branched.

The aryl groups represented preferably by $R_{22}$ include a phenyl group.

The acylamino groups represented by $R_1$ include each group of alkylcarbonylamino, arylcarbonylamino and so forth.

The sulfonamido groups represented by $R_{22}$ include each group of alkylsulfonylamino, arylsulfonylamino and so forth.

The alkyl components and aryl components of the alkylthio groups and arylthio groups each represented by $R_{22}$ include the alkyl groups and aryl groups each represented by the above-denoted $R_{21}$, respectively.

The alkenyl groups represented by $R_{22}$ include, preferably, those having 2 to 32 carbon atoms. The cycloalkyl groups represented thereby include preferably those having 3 to 12 carbon atoms and, more preferably, those having 5 to 7 carbon atoms. The above-mentioned alkenyl groups may be straight-chained or branched.

The cycloalkenyl groups represented by $R_{22}$ include, preferably, those having 3 to 12 carbon atoms and, more preferably, those having 5 to 7 carbon atoms.

The carbamoyloxy groups include, for example, an alkylcarbamoyloxy group, an arylcarbamoyloxy group and so forth;

The ureido groups include, for example, an alkylureido group, an arylureido group and so forth;

The sulfamoylamino groups include, for example, an alkylsulfamoylamino group, an arylsulfamoylamino group and so forth;

The heterocyclic groups may preferably be the 5- to 7-membered and they include typically a 2-furyl group, a 2-thienyl group, a 2-pyrimidinyl group, a 2-benzothiazolyl group and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylbutylsiloxy group, a triethylsiloxy group, a dimethylbutylsiloxy group and so forth;

As regards X, and Z the same definitions as in formula [I]-1 are respectively applied.

According to a further embodiment of the invention, the cyan dye-forming coupler is represented by the following Formula [I]-3:

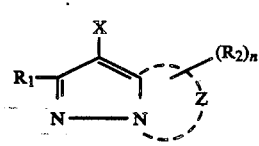

Formula [I]-3 wherein at least $R_1$ represented a group slected from the group consisting of each group of sulfonyl, sulfinyl, sulfonyloxy, sulfonylmethyl, sulfamoyl, phosphoryl, tetrazolyl, pyrrolyl, halogenated alkoxy, halogenated aryloxy, acyl, halogen, nitro and carboxy; X represents a hydrogen atom or a substituent capable of splitting off upon reaction with the oxidized product of a color developing agent; Z represents a group of non-metal atoms required for completing a nitrogen-containing heterocyclic ring; $R_2$ represents a hydrogen atom or a substituent and is bonded to the carbon atom of the above-mentioned nitrogen-containing heterocyclic ring; n is an integer of 1 or 2, provided that $R_2$ may be the same with or the different from each other if n is 2.

In the above-given Formula [I]-3, at least $R_1$ represents a substituent selected from the group consisting of each group of sulfonyl, sulfinyl, sulfonyloxy, sulfonylmethyl, sulfamoyl, phosphoryl, halogenated alkoxy, halogenated aryloxy, acyl, halogen, nitro, tetrazolyl, pyrrolyl, carboxyl and so forth.

For example, the sulfonyl groups include each group of alkylsulfonyl, arylsulfonyl, halogenated alkylsulfonyl, halogenated arylsulfonyl and so forth.

The sulfinyl groups include each group of alkylsulfinyl, arylsulfinyl, halogenated alkylsulfinyl, halogenated arylsulfinyl and so forth.

The sulfonyloxy groups include each group of alkylsulfonyloxy, arylsulfonyloxy and so forth.

The sulfamoyl groups may be substituted with each group of alkyl, aryl or the like.

The phosphoryl groups include each group of alkoxyphosphoryl, alkylphosphoryl, arylphosphoryl and so forth.

The halogenated alkoxy groups include, preferably, a 1-halogenated alkoxy group such as a trifluoromethoxy group and so forth.

The halogenated aryloxy groups include, preferably, a tetrafluoroaryloxy group, a pentafluoroaryloxy group and so forth.

The halogen atoms include a bromine atom, chlorine atom and so forth.

The tetrazolyl groups include such a 1-tetrazolyl group and so forth.

The pyrrolyl groups include a 1-pyrrolyl group and so forth.

The acyl groups include each group of alkylcarbonyl, arylcarbonyl and so forth.

The sulfonylmethyl groups include each group of alkylsulfonylmethyl, arylsulfonylmethyl and so forth;

The particularly preferable substituents of the above-given ones include each group of sulfonyl, sulfinyl, sulfonyloxy, sulfamoyl, phosphoryl, tetrazolyl, pyrrolyl, halogenated alkoxy, halogenated aryloxy and acyl. In Formula [I]-3, at least $R_1$ having the above-given substituent is capable of providing particularly desirable spectral absorption characteristics.

Among the above-given substituents, the further preferable ones include each group of sulfonyl, sulfinyl, sulfonyloxy, sulfamoyl and acyl. These having the above-given substituents is capable of displaying more desirable spectral absorption characteristics.

The above-given groups are also allowed to have a substituent including a ballast group such as a long-chained hydrocarbon group and a polymer residual group, an electron withdrawing group, and so forth.

In Formula [I]-3, $R_2$ may be introduced thereinto with the above-given substituents, any other substituents or a hydrogen atom.

The substituents represented by $R_2$ include, typically, each group of alkyl, aryl, anilino, acylamino, sulfonamido, alkylthio, arylthio, alkenyl, cycloalkyl and so forth and, besides the above, each group of cycloalkenyl, alkinyl, heterocyclic, alkoxy, aryloxy, heterocyclic-oxy, siloxy, carbamoyloxy, amino, alkylamino, imido, ureido, sulfamoylamino, carbonylamino and heterocyclic-thio, as well as a spiro-compound residual group, a cross-linked hydrocarbon compound residual group and so forth.

The alkyl groups represented by $R_2$ include, preferably, those having 1 to 32 carbon atoms and they may be straight-chained or branched.

The aryl groups represented by $R_2$ include, preferably, a phenyl group.

The acylamino groups represented by $R_2$ include each group of alkylcarbonylamino, arylcarbonylamino and so forth.

The sulfonamido groups represented by $R_2$ include each group of alkylsulfonylamino, arylsulfonylamino and so forth.

The alkyl components and aryl components of the alkylthio groups and arylthio groups each represented by $R_2$ include the alkyl groups and aryl groups each represented by the above-denoted $R_2$, respectively.

The alkenyl groups represented by $R_2$ include, preferably, those having 2 to 32 carbon atoms. The cycloalkyl groups represented thereby include preferably those having 3 to 12 carbon atoms and, more preferably, those having 5 to 7 carbon atoms. The above-mentioned alkenyl groups may be straight-chained or branched.

The cycloalkenyl groups represented by $R_2$ include, preferably, those having 3 to 12 carbon atoms and, more preferably, those having 5 to 7 carbon atoms.

The carbamoyloxy groups include, for example, an alkylcarbamoyloxy group, an arylcarbamoyloxy group and so forth;

The ureido groups include, for example, an alkylureido group, an arylureido group and so forth;

The sulfamoylamino groups include, for example, an alkylsulfamoylamino group, an arylsulfamoylamino group and so forth;

The heterocyclic groups may preferably be the 5- to 7-membered and they include typically a 2-furyl group, a 2-thienyl group, a 2-pyrimidinyl group, a 2-benzothiazolyl group and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth;

The imido groups include each group of succinimido, 3-heptadecyl succinimido, phthalimido, glutarimido and so forth;

The spiro-compound residual groups include a spiro[3.3]heptane-1-yl and so forth;

The cross-linked hydrocarbon compound residual groups include each group of bicyclo[2.2.1]heptane-1-yl, tricyclo [3.3.1.1$^{37}$]decane-1-yl, 7,7-dimethyl-bicyclo[2.2.1]heptane-1-yl and so forth;

The carbonylamino groups include each group of alkoxycarbonylamino, aryloxycarbonylamino and so forth;

The above-given groups may also have a substituent including a ballast group such as a long-chained hydrocarbon group, a polymer residual group and so forth, or an electron withdrawing group and so forth.

As regads X and Z the same definitions as in formula [I]-1 are respectively applied.

According to a still further embodiment of the invention, the cyan dye-forming coupler is represented by the following Formula [I]-4;

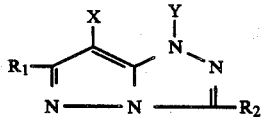

Formula [I]-4 wherein R$_1$ represents a cyano group, an acyloxy group, an oxycarbonyl group or a carbamoyl group; R$_2$ and Y represent a hydrogen atom or a substituent; and X represents a hydrogen atom or a group capable of splitting off upon reaction with the oxidized product of a color developing agent.

The cyan dye-forming couplers represented by the above-given Formula [I]-4 relating to the invention are pyrazoloazole type compounds having an electron withdrawing group.

In Formula [I]-4, the electron withdrawing groups are preferably the substituents having a substituent constant $\sigma p$ (defined by Hammett) of not less than +0.20.

In the cyan couplers represented by Formula [I]-4, R$_1$ represents, typically, each group of cyano, acyloxy, oxycarbonyl or carbamoyl.

The acyloxy groups include, prefrably, an alkylcarbonyloxy group and so forth.

The oxycarbonyl groups include, for example, an alkoxycarbonyl group, an aryloxycarbonyl group, and so forth.

The carbamoyl groups may be substituted with an alkyl group, an aryl group and preferably a phenyl group, and so forth.

There shall be no special limitation to the substituents represented by R$_2$ in Formula [I]-4, however, they include each group of alkyl, aryl, anilino, acylamino, sulfonamido, alkyl-thio, arylthio, alkenyl, cycloalkenyl and so forth and, besides the above, they include a halogen atom and each group of cycloalkenyl, alkinyl, heterocyclic, sulfonyl, sulfinyl, phosphonyl, acyl, sulfamoyl, sulfonyloxy, alkoxy, aryloxy, heterocyclic-oxy, siloxy, carbamoyloxy, amino, alkylamino, imido, ureido, sulfamoylamino, alkoxycarbonylamino, aryloxy-carbonylamino, heterocyclic-thio, thioureido, carboxy, hydroxy, mercapto, nitro, sulfonic acid and so forth, as well as a spiro-compound residual group, a cross-linked hydro-carbon compound residual group and so forth;

The alkyl groups represented by R$_2$ may preferably be those having 1 to 32 carbon atoms and may be either straight chained or branched;

The aryl groups include, preferably, a phenyl group.

The acylamino groups include, for example, an alkylcarbonylamino group, an arylcarbonylamino group and so forth.

The sulfonamido groups include, for example, an alkylsulfonylamino group, an arylsulfonylamino group and so forth;

In the alkylthio groups and the arylthio groups, the alkyl component and aryl component thereof include the alkyl groups and aryl groups each represented by the above R$_2$, respectively;

The alkenyl groups may preferably be those having 2 to 32 carbon atoms, and the cycloalkyl groups may be those having 3 to 12 carbon atoms preferably and those having 5 to 7 carbon atoms more preferably. The alkenyl groups may be either straight chained or branched;

The cycloalkenyl groups may be those having 3 to 12 carbon atoms preferably and those having 5 to 7 carbon atoms more preferably;

The sulfonyl groups include each group of alkylsulfonyl, arylsulfonyl and so forth;

The sulfinyl groups include each group of alkylsulfinyl, arylsulfinyl and so forth;

The phosphonyl groups include each group of alkylphosphonyl, alkoxyphosphonyl, aryloxyphosphonyl, arylphosphonyl and so forth;

The acyl groups include each group of alkylcarbonyl, arylcarbonyl and so forth;

The sulfamoyl groups include each group of alkylsulfamoyl, arylsulfamoyl and so forth;

The carbamoyloxy groups include each group of alkylcarbamoyloxy, arylcarbamoyloxy and so forth;

The ureido groups include each group of alkylureido, arylureido and so forth;

The sulfamoylamino groups include each group of alkylsulfamoylamino, arylsulfamoylamino and so forth;

The heterocyclic groups may preferably be the 5- to 7-membered and they include typically a 2-furyl group, a 2-thienyl group, a 2-pyrimidinyl group, a 2-benzothiazolyl group, a 1-pyrrolyl group, a 1-tetrazolyl group and so forth;

The heterocyclic-oxy groups may preferably be those having a 5- to 7-membered heterocyclic ring and they include, for example, a 3,4,5,6-tetrahydropyranyl-2-oxy group, a -1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth;

The imido groups include, for example, a succinimido group, a 3-heptadecylsuccinimido group, a phthalimido group, a glutarimido group and so forth;

The spiro compound residual groups include, for example, a spiro[3.3]heptane-1-yl and so forth;

The cross-linked hydrocarbon compound residual groups include, for example, a bicyclo[2.2.1]heptane-1-yl, a tricyclo[3.3.1.1$^{27}$]decane-1-yl, a 7,7-dimethylbicyclo[2.2.1]heptane-1-yl and so forth; and The aforementioned substituents represented by $R_1$ and $R_2$ each are also allowed to have a substituent including a ballast group such as long-chained hydrocarbon group, a polymer residual group and so forth.

As regards X, the same definition as given in formula [I]-1 is applied.

The substituent advantageous for Y includes those which are split off from the resulting compound after the reaction of the cyan dye-forming coupler of the formula with the oxidation product of a color developing agent. For example, those which can be split off under alkaline condition as disclosed in Japanese Patent O.P.I. publication No. 228444/1986 or those which are coupling-off upon reaction with the oxydation product of the color developing agent as disclosed in Japanese Patent O.P.I. Publication No. 133734/1981 can be mentioned. Hydrogen atom is most Preferable for Y.

According to still another embodiment of the invention, the cyan dye-forming coupler is one represented by the following Formula [I]-5:

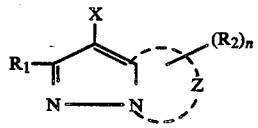

Formula [I]-5 wherein Z represents a group of non-metal atoms required for completing a nitrogen-containing heterocyclic ring; X represents a hydrogen atom or a substituent capable of splitting off upon reaction with the oxidized product of a color developing agent; $R_1$ represents a hydrogen atom or a substituent; $R_2$ represents an electron withdrawing group; and n is an integer of 1 or 2.

The cyan dye-forming couplers represented by the above-given Formula [I]-5 relating to the invention are characterized by having at least one electron withdrawing group $R_2$ in the azole portion of the pyrazoloazole nucleus of the coupler.

The substituents represented by $R_2$ include, typically, each of group of alkyl, aryl, anilino, acylamino, sulfonamido, alkylthio, arylthio, alkenyl, cycloalkyl and so forth. Besides the above, they also include a halogen atom and each group of cycloalkenyl, alkinyl, heterocyclic, alkoxy, aryloxy, heterocyclic-oxy, siloxy, carbamoyloxy, amino, alkylamino, imido, ureido, sulfamoylamino, alkoxycarbonylamino, aryloxycarbonylamino, alkoxycarbonyl, aryloxycarbonyl and heterocyclic-thio, as well as a spiro-compound residual group, a cross-linked hydrocarbon compound residual group and so forth.

The alkyl groups represented by $R_1$ preferably include those having 1 to 32 carbon atoms and they may be straight-chained or branched.

The aryl groups represented preferably by $R_1$ include a phenyl group.

The acylamino groups represented by $R_1$ include each group of alkylcarbonylamino, arylcarbonylamino and so forth.

The sulfonamido groups represented by $R_1$ include each group of alkylsulfonylamino, arylsulfonylamino and so forth.

The alkyl components and aryl components of the alkylthio groups and arylthio groups each represented by $R_1$ include the alkyl groups and aryl groups each represented by the above-denoted $R_1$, respectively.

The alkenyl groups represented by $R_1$ include, preferably, those having 2 to 32 carbon atoms. The cycloalkyl groups represented thereby include preferably those having 3 to 12 carbon atoms and, more preferably, those having 5 to 7 carbon atoms. The above-mentioned alkenyl groups may be straight-chained or branched.

The cycloalkenyl groups represented by $R_{22}$ include, preferably, those having 3 to 12 carbon atoms and, more preferably, those having 5 to 7 carbon atoms.

The sulfonyl groups represented by $R_1$ include each group of akylsulfonyl, arylsulfonyl and so forth;

The sulfinyl groups include each group of alkylsulfinyl, arylsulfinyl and so forth;

The phosphonyl groups include each group of alkylphosphonyl, alkoxyphosphonyl, aryloxyphosphonyl, arylphosphonyl and so forth;

The acyl groups include each group of alkylcarbonyl, arylcarbonyl and so forth;

The carbamoyl groups include each group of alkylcarbamoyl, arylcarbamoyl and so forth;

The sulfamoyl groups include each group of alkylsulfamoyl, arylsulfamoyl and so forth;

The acyloxy groups include each group of alkylcarbonyloxy, arylcarbonyloxy and so forth;

The carbamoyloxy groups include each group of alkylcarbamoyloxy, arylcarbamoyloxy and so forth;

The ureido groups include each group of alkylureido, arylureido and so forth;

The sulfamoylamino groups include each group of alkylsulfamoylamino, arylsulfamoylamino and so forth;

The heterocyclic groups may preferably be the 5- to 7-membered and they include typically a 2-furyl group, a 2-thienyl group, a 2-pyrimidinyl group, a 2-benzothiazolyl group, and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth;

The imido groups include, for example, a succinimido group, a 3-heptadecylsuccinimido group, a phthalimido group, a glutarimido group and so forth;

The spiro compound residual groups include, for example, a spiro[3.3]heptane-1-yl and so forth;

The cross-linked hydrocarbon compound residual groups include, for examle, a bicyclo[2.2.1]heptane- 1-yl, a tricyclo[3.3.1.1³⁷]decane-1-yl, a 7,7-dimethyl-bicyclo[2.2.1]heptane-1-yl and so forth;

The electron withdrawing groups represented by $R_2$ are the substituents having an F value of not less than +0.30 in quantitative structural active relation according to Hansch Method. They include, typically, a halogen atom and each group of nitro, cyano, acylamino, acyloxy, halogenated alkyl, sulfonyl, carboxyl, sulfonyloxy, sulfinyl, sulfamoyl, phosphonyl, pyrrole, tetrazolyl, and so forth:

The halogen atoms represente by $R_2$ include, a fluorine atom, a chlorine atom, a bromine atom and so forth.

The acylamino groups represented by $R_2$ include each group of acetylamino, trifluoroacetylamino, benzoylamino and so forth:

The acyloxy groups represented by $R_2$ include each group of acetyloxy, 2-chloroacetyloxy, benzoyloxy and so forth.

The halogenated alkyl groups represented by $R_2$ include, each group od trifluoromethyl, 2-chloroethyl and so forth.

The sulfonyl groups represented by $R_2$ include each group of methyl sulfonyl, trifluoromethyl sulfonyl, benzene sulfonyl, p-toluene sulfonyl and so forth.

The sulfonyloxy groups include each group of methyl sulfonyloxy, trufluoromethyl sulfonyloxy, benzene sulfonyloxy and so forth.

The sulfinyl groups include methyl sulfinyl, octyl sulfinyl, 3-phenoxybutyl sulfinyl, m-pentadecylphenyl sulfinyl and so forth.

The sulfamoyl groups include each group of N-propyl sulfamoyl, N-phenyl sulfamoyl, N,N-diethyl sulfamoyl, N-ethyl-N-dodecyl sulfamoyl and so forth.

The phophonyl groups include each group of ethoxy phosphonyl, butoxy phosphonyl, phenoxy phosphonyl and so forth.

The tetrazolyl groups include each group of 1-tetraazolyl, 5-chloro-1-tetrazolyl and so forth.

Among the above-given groups, the preferable ones are each group of cyano, acyloxy, sulfonyl, sulfinyl, sulfamoyl, phosphonyl, and tetrazolyl.

The above-given groups are also allowed to have a substituent such as a ballast group, an electron withdrawing group and so forth.

As for X and Z, the same definitions are applied as in formula [I]-1.

Among substituents for $R_1$ electron withdrawing groups are preferable, and more preferably, those having F-value of not less than +0.30 can be mentioned. To be concrete, a halogen atom, such as chlorine, bromine or fluorine atom, an alkylchloride group such as trifluoromethyl group, an acyloxy group such as acetyloxy group or γ-chloroacetyloxy group, a sulfonyl group, such as methyl sulfonyl group, dodecyl sulfonyl group, benzene sulfonyl group or p-chlorobenzene sulfonyl group, a sulfinyl group such as methylsulfinyl group, 3-phenoxybutyl sulfinyl group, phenyl sulfinyl group or m-pentadecylphenyl sulfinyl group, a sulfamoyl group such as N-propyl sulfamoyl group, N-phenyl sulfamoyl group. N,N-diethyl sulfamoyl group or N-ethyl-N-dodecylsulfamoyl group, a phosphonyl group such as ethoxyphosphonyl group or phenoxyphosphonyl group, a heterocyclic group such as pyrrolyl group or 5-chlorotetrazolyl group can be mentioned provided that these groups may be substituted.

According to an additional embodiment of the invention, the cyan dye-forming coupler coupler is represented by the following Formula [I]-6:

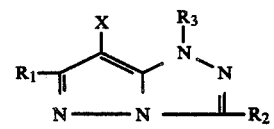

Formula [I]-6 wherein at least $R_2$ represents a substituent selected from the group consisting of sulfonyl, sulfonyloxy, sulfinyl, sulfamoyl, phosphoryl, tetrazolyl, pyrrolyl, halogenated alkoxy, halogenated aryloxy, halogen, cyano, nitro, acyl and carbamoyl groups; $R_1$ and $R_3$ represent a hydrogen atom or a substituent; and X represents a hydrogen atom or a group capable of splitting off upon reaction with the oxidized product of a color developing agent.

The couplers represented by the above-given Formula [I]-6 relating to the invention are characterized in that the pyrazoloazole nucleus of the coupler has an electron with-drawing group.

The substituents represented by at least $R_2$ include each group of sulfonyl, sulfinyl, sulfonyloxy, sulfamoyl, cyano, acyl, phosphoryl, tetrazolyl, pyrrolyl, carbamoyl, halogenated alkoxy, halogenated aryloxy and nitro, and a halogen atom.

For example, the sulfonyl groups include each group of alkylsulfonyl, arylsulfonyl, halogenated alkylsulfonyl, halogenated arylsulfonyl and so forth.

The sulfinyl groups include each group of alkylsulfinyl, arylsulfinyl, halogenated alkylsulfinyl, halogenated arylsulfinyl and so forth.

The sulfonyloxy groups include each group of alkylsulfonyloxy, arylsulfonyloxy and so forth.

The sulfamoyl groups may be substituted with each group of alkyl, aryl or the like.

The acyl groups include each group of alkylcarbonyl, arylcarbonyl, and so forth;

The phosphoryl groups include each group of alkoxyphosphoryl, alkylphosphoryl and so forth.

The tetrazolyl groups include each group of 1-tetrazolyl and so forth;

The pyrrolyl groups include each group of 1-pyrrolyl and so forth;

The carbamoyl groups may be substituted by a group of alkyl, aryl and so forth;

The halogenated alkoxy groups include, preferably, a 1-halogenated alkoxy group such as a trifluoromethoxy group and so forth.

The halogenated aryloxy groups include, preferably, a tetrafluoroaryloxy group, a pentafluoroaryloxy group and so forth.

The halogen atoms include a bromine atom, chlorine atom and so forth.

The particularly preferable substituents of the above-given ones include each group of sulfonyl, sulfinyl, sulfonyloxy, sulfamoyl, acyl, cyano, phosphoryl, tetrazolyl and pyrrolyl. In Formula [I]-6, at least $R_1$ having the above-given substituent is capable of displaying particularly desirable spectral absorption characteristics.

Among the above-given substituents, the further preferable ones include each group of sulfonyl, sulfinyl, sulfonyloxy, sulfamoyl acyl and cyano. These having the above-given substituents is capable of displaying more particularly desirable spectral absorption characteristics.

The above-given groups are allowed to have a substituent including a ballast group such as a long-chained hydrocarbon group and a polymer residual group, an elecron withdrawing group, and so forth.

In Formula [I]-6, $R_1$ may be introduced thereinto with the above-given substituents, any other substituents or a hydrogen atom.

The substituents represented by $R_1$ include, typically, each group of alkyl, aryl, anilino, acylamino, sulfonamido, alkylthio, arylthio, alkenyl, cycloalkyl and so forth and, besides the above, each group of cycloalkenyl, alkinyl, heterocyclic, alkoxy, aryloxy, heterocyclic-oxy, siloxy, carbamoyloxy, amino, alkylamino, imido, ureido, sulfamoylamino, carbonylamino and heterocyclic-thio, as well as a spiro-compound residual group, a cross-linked hydrocarbon compound residual group and so forth.

The alkyl groups represented by $R_1$ include, preferably, those having 1 to 32 carbon atoms and they may be straight-chained or branched.

The aryl groups represented by $R_1$ include, preferably, a phenyl group.

The acylamino groups represented by $R_1$ include each group of alkylcarbonylamino, arylcarbonylamino and so forth.

The sulfonamido groups represented by $R_1$ include each group of alkylsulfonylamino, arylsulfonylamino and so forth.

The alkyl components and aryl components of the alkylthio groups and arylthio groups each represented by $R_1$ include the alkyl groups and aryl groups each represented by the above-denoted $R_1$, respectively.

The alkenyl groups represented by $R_1$ include, preferably, those having 2 to 32 carbon atoms. The cycloalkyl groups represented thereby include preferably those having 3 to 12 carbon atoms and, more preferably, those having 5 to 7 carbon atoms. The above-mentioned alkenyl groups may be straight-chained or branched.

The cycloalkenyl groups represented by $R_1$ include, preferably, those having 3 to 12 carbon atoms and, more preferably, those having 5 to 7 carbon atoms.

The carbamoyloxy groups include, for example, an alkylcarbamoyloxy group, an arylcarbamoyloxy group and so forth;

The ureido groups include, for example, an alkylureido groups, an arylureido group and so forth;

The sulfamoylamino groups include, for example, an alkylsulfamoylamino group, an arylsulfamoylamino group and so forth;

The heterocyclic groups may preferably be the 5- to 7-membered and they include typically a 2-furyl group, a 2-thienyl group, a 2-pyrimidinyl group, a 2-benzothiazolyl group and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth;

The imido groups include each group of succinimido, 3-heptadecyl succinimido, phthalimido, glutarimido and so forth;

The spiro-compound residual groups include a spiro [3.3] heptane-1-yl and so forth;

The cross-linked hydrocarbon compound residual groups include each group of bicyclo[2.2.1]heptane-1-yl, tricyclo8 3.3.1.1$^{27}$]decane-1-yl, 7,7-dimethyl-bicyclo[2.2,1] heptane-1-yl and so forth;

The carbonylamino groups include each group of alkoxycarbonylamino, aryloxycarbonylamino and so forth; and The above-given groups may also have a substituent including a ballast group such as a long-chained hydrocarbon group, a polymer residual group and so forth, or an electron withdrawing group and so forth.

As for X, the same definition can be applied as in formula [I]-1.

Further as $R_3$, those substituents as mentioned in formula [I]-4 can be mentioned. Among them hydrogen atom is most preferable.

According to another embodiment of the Invention, the cyan dye-forming coupler is one represented by the following Formula [I]-7:

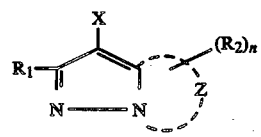

Formula [I]-7 wherein at least two group, selected from the group consisting of $R_1$ and $R_2$, is an electron withdrawing group; Z represents a group of non-metal atoms required for completing a nitrogen-containing hetero-cyclic ring; each of $R_2$s is bonded to the carbon atom of the heterocyclic ring; X represents a hydrogen atom or a substituent capable of splitting off upon reaction with the oxidized product of a color developing agent; and n is an integer of 1 to 2. When n is 1, $R_2$ represents an electron withdrawing group, and when n is 2, $R_2$ represents either electron withdrawing groups or substituents which may be the same with or the different from each other and at least one thereof is an electron withdrawing group. $R_2$ is bonded to the carbon atom of the above-mentioned nitrogen-containing heterocyclic ring.

The couplers represented by Formula [I]-7 relating to the invention are characterized in that the pyrazoloazole nucreus thereof has an electron withdrawing group. At least two of the electron withdrawing groups selected from the group consisting of $R_1$ and $R_2$ are preferably the substituents having a substituent constant $\sigma p$ (defined by Hammett) of not less than +0.20. They include, typically, each group of sulfonyl, sulfonyloxy, sulfinyl, sulfamoyl, phosphoryl, halogen, halogenated alkoxy, halogenated aryloxy, nitro, pyrrolyl, tetrazolyl, cyano, carbamoyl, acyl, acyloxy, carboxyl, oxycarbonyl and so forth;

The sulfonyl groups include each group of alkylsulfonyl, arylsulfonyl, halogenated alkylsulfonyl, halogenated arylsulfonyl and so forth.

The sulfonyloxy groups include each group of alkylsulfonyloxy, arylsulfonyloxy and so forth.

The sulfinyl groups include each group of alkylsulfinyl, arylsulfinyl, halogenated alkylsulfinyl, halogenated arylsulfinyl and so forth.

The sulfamoyl groups may be substituted with each group of alkyl, aryl or the like.

The phosphoryl groups include each group of alkoxyphosphoryl, alkylphosphoryl, arylphosphoryl and so forth.

The halogen atoms include each atom of bromine, chlorine and so forth;

The halogenated alkoxy groups include, preferably, a 1-halogenated alkoxy group.

The halogenated aryloxy groups include, preferably, a tetra- or pentafluoroaryloxy group and so forth.

The pyrrolyl groups include a 1-pyrrolyl group and so forth.

The tetrazolyl groups include such a 1-tetrazolyl group and so forth.

The acyl groups include each group of alkylcarbonyl, arylcarbonyl and so forth.

The acyloxy groups include each group of alkylcarbonyloxy and so forth; The oxycarbonyl groups include each group of alkoxy-carbonyl, aryloxycarbonyl and so forth;

Besides the above, for the halogenated alkyl groups, a 1-halogenated alkyl groups such as a trifluoromethyl group and so forth may preferably be used.

For the halogenated aryl groups, a tetra- or pentafluoroaryl group may preferably be used.

Further, an arylsulfonylmethyl group, an alkylsulfonylmethyl group and so forth may preferably be used.

The above-given groups are also allowed to have a substituent including a ballast group such as a long-chained hydrocarbon group and a polymer residual group, an elecron withdrawing group, and so forth.

In Formula [I]-7, when n is 2 and $T_1$ or $R_2$ is a substituent other than an electron withdrawing group, the substituent is preferably a hydrogen atom or may be any substituent.

The substituents include, typically, each group of alkyl, aryl, anilino, acylamino, sulfonamido, alkylthio, arylthio, alkenyl, cycloalkyl and so forth and, besides the above, each group of cycloalkenyl, alkinyl, heterocyclic, alkoxy, aryloxy, heterocyclic-oxy, siloxy, carbamoyloxy, amino, alkylamino, imido, ureido, sulfamoylamino, alkoxycarbonylamino, alkoxycarbonyl, aryloxycarbonyl, and heterocyclic-thio, as well as a spiro-compound residual group, a cross-linked hydrocarbon compound residual group and so forth.

The alkyl groups represented by $R_1$ or $R_2$ include, preferably, those having 1 to 32 carbon atoms and they may be straight-chained or branched.

The aryl groups include, preferably, a phenyl group.

The sulfonamido groups include each group of alkylsulfonylamino, arylsulfonylamino and so forth.

The alkyl components and aryl components of the alkylthio groups and arylthio groups include the alkyl groups and aryl groups, respectively.

The alkenyl groups include, preferably, those having 2 to 32 carbon atoms. The cycloalkyl groups represented thereby include preferably those having 3 to 12 carbon atoms and, more preferably, those having 5 to 7 carbon atoms. The above-mentioned alkenyl groups may be straight-chained or branched.

The cycloalkenyl groups include, preferably, those having 3 to 12 carbon atoms and, more preferably, those having 5 to 7 carbon atoms.

The carbamoyloxy groups include an alkyl carbamoyloxy group, an arylcarbamoyloxy group and so forth;

The ureido groups include an alkylureido group, an arylureido group and so forth;

The sulfamoylamino groups include an alkylsulfamoylamino group, an arylsulfamoylamino group and so forth;

The heterocyclic groups may preferably be the 5- to 7-membered and they include typically a 2-furyl group, a 2-thienyl group, a 2-pyrimidinyl group, a 2-benzothiazolyl group and so forth;

The heterocyclic-oxy groups may preferably be those having a 5- to 7-membered heterocyclic ring and they include, for example, a 3,4,5,6-tetrahydropyranyl-2-oxy group, a 1-phenyltetrazole-5-oxy group and so forth;

The heterocyclic-thio groups may preferably be a 5- to 7-membered heterocyclic-thio group and they include, for example, a 2-pyridylthio grop, a 2-benzothiazolylthio group, a 2,4-diphenoxy-1,3,5-triazole-6-thio group and so forth;

The siloxy groups include, for example, a trimethylsiloxy group, a triethylsiloxy group, a dimethylbutylsiloxy group and so forth.

As for X and Z, those atoms and groups as in formula [I]-1 are mentioned.

The cyan dye-forming couplers which are advantageously used in the present invention are further represented by the following Formulas [II] through [VI]:

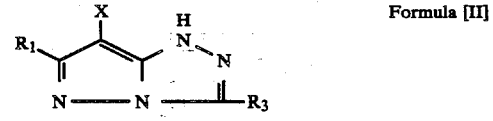

Formula [II]

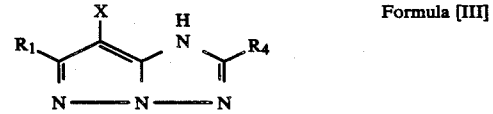

Formula [III]

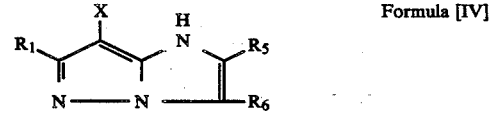

Formula [IV]

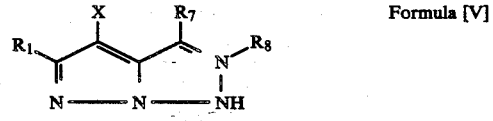

Formula [V]

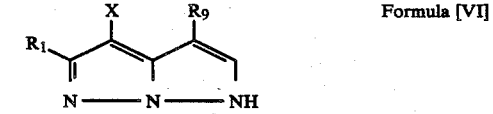

Formula [VI]

In the above-given Formulas [II] through [VI], $R_1$ is synonymous with $R_1$ denoted in Formula [I]-1; and $R_3$ through $R_9$ and X are synonymous with the aforegiven $R_2$ and X, respectively.

The typical examples of the compounds relating to the invention will be given below. It is, however, to be understood that these examples are merely some of the compounds relating to the invention and the compounds shall not be limited thereto.

Formula [II]

$$\begin{array}{c} X \\ \| \\ R_1-C \\ \phantom{R_1-}\diagdown N \\ \phantom{R_1-}\phantom{\diagdown}N-N \end{array} \begin{array}{c} H \\ N-N \\ \diagup \\ C-R_3 \end{array}$$

| Coupler No. | $R_1$ | $R_3$ | X |
|---|---|---|---|
| [II]-1-1 | $CF_3$— | —$(CH_2)_3SO_2$—C₆H₄—$C_{12}H_{25}$ | H |
| [II]-1-2 | $C_2H_5$—C(Cl)—$C_2H_5$ | 4-$C_4H_9(t)$-C₆H₃(NHCOCHC₂H₅-C₆H₄-CH₃)O— (phenoxy with NHCOCH(C₂H₅)-p-tolyl and p-C₄H₉(t) substituents) | —O—C₆H₅ |
| [II]-1-3 | $CH_3$—C(Br)—$CH_3$ | 2-$OC_{12}H_{25}$-5-$CH_3$-C₆H₃-SO₂CH(CH₃)CH₂CH₂— | Cl |
| [II]-1-4 | C₆F₅ (pentafluorophenyl) | 2-Cl-C₆H₄-N(C₆H₄-CH₃)COCHO-$C_{12}H_{25}$ | H |
| [II]-1-5 | C₆H₅—(phenyl) | —O—C(=O)—$C_{18}H_{37}$ | —S—C₆H₄—NHCOCF₃ |
| [II]-1-6 | $C_{11}H_{23}$ | —COOH | H |
| [II]-1-7 | $C_2H_5$ | —COO$C_{10}H_{21}$ | Cl |
| [II]-1-8 | $(t)C_4H_9$ | —CH₂—SO₂—C₆H₄—NHCO$C_{12}H_{25}$ | —SCH₃ |

-continued

Formula [II]

$$\underset{R_1}{\overset{X}{\underset{N}{\bigg|}}}\!\!\!\!\!\!\!\!\!\!\!\!\!\!\!\!\!\!\!\!\!\!\!\!\!\!\!\!\!\!\!\!\!\underset{N-N}{\overset{H}{N-N}}\!\!\!\!R_3$$

| Coupler No. | $R_1$ | $R_3$ | X |
|---|---|---|---|
| [II]-1-9 | $CH_3-$ | 2,3,5,6-tetrafluoro-4-(NHCOCHO($C_8H_{17}$))phenyl with $OC_4H_9$ and (t)$OC_8H_{17}$ substituents | $-NHCOCF_3$ |
| [II]-1-10 | $CF_3-$ | 3-methylphenyl-NHCOCH($C_{12}H_{25}$)- with (t)$C_5H_{11}$ and (t)$C_5H_{11}$ | H |
| [II]-1-11 | (t)$OC_4H_9-$ | $-COOCH_2$—C$_6$H$_4$—NHCOC$_{12}$H$_{25}$ | Cl |
| 2-1 | 2-Cl-phenyl-SO$_2$— | $-(CH_2)_3-SO_2-$ phenyl with $OC_4H_9$ and $C_8H_{17}$(t) | H |
| 2-2 | pentafluorophenyl-SO$_2$— | phenyl-NHCOCH($C_4H_9$)— with $C_5H_{11}(t)$, $C_5H_{11}(t)$, and 3-Cl-phenyl | H |

-continued

Formula [II]

$$\begin{array}{c} X \\ | \\ R_1 \end{array} \underset{N=N}{\overset{H}{\underset{|}{N-N}}} R_3$$

| Coupler No. | $R_1$ | $R_3$ | X |
|---|---|---|---|
| 2-3 | —SO$_2$—C$_6$H$_4$—CF$_3$ | 4-OH, 3-C$_4$H$_9$(t), phenyl with NHCOCHO-C$_{12}$H$_{25}$ substituent | H |
| 2-4 | —SO$_2$C$_4$H$_9$ | phenyl-SO$_2$-C$_6$H$_4$-OH with NHCOCHO-C$_{10}$H$_{21}$ | Cl |
| 2-5 | —PO(C$_8$H$_{17}$)$_2$ | —(CH$_2$)$_3$—CHCH$_2$SO$_2$C$_{18}$H$_{37}$ / C$_2$H$_5$ | H |
| 2-6 | —OSO$_2$CF$_3$ | phenyl with C$_5$H$_{11}$(t), C$_5$H$_{11}$(t), NHCO(CH$_2$)$_3$O— substituent | Cl |
| 2-7 | —C(CF$_3$)$_3$ | 3-Cl, 4-methyl phenyl with CH$_2$CH$_2$SO$_2$CH$_2$CH(C$_8$H$_{17}$)$_2$ | Cl |
| 2-8 | pentafluorobenzoyl (C$_6$F$_5$-CO—) | —CHCH$_2$CH$_3$SO$_2$—C$_6$H$_4$—OC$_{12}$H$_{25}$ / CH$_3$ | Cl |

-continued
Formula [II]
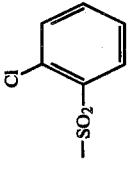
| Coupler No. | $R_1$ | $R_3$ | X |
|---|---|---|---|
| 2-9 | 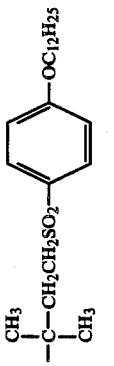 |  | H |
| 2-10 | —SO$_2$N(C$_2$H$_5$)$_2$ | 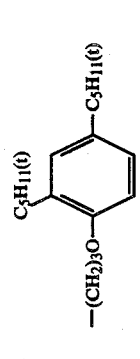 | Cl |
| 2-11 | —CO(CF$_2$)$_3$H |  | Cl |
| 2-12 | —O(CF$_2$)$_{11}$H | 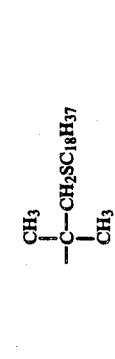 | Cl |
| 2-13 |  | 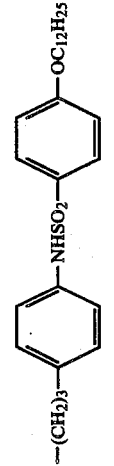 | Cl |
| 2-14 |  | 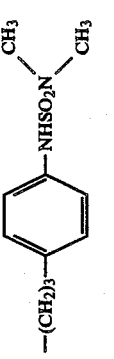 | Cl |

-continued

Formula [II]:

$$R_1 \underset{N}{\overset{X}{\underset{\|}{\text{C}}}} \underset{N}{\overset{H}{\underset{\|}{N}}} - N \underset{\|}{\overset{}{\underset{N}{\|}}} R_3$$

| Coupler No. | $R_1$ | $R_3$ | X |
|---|---|---|---|
| 2-15 | 2-OC$_4$H$_9$, 4-C$_8$H$_{17}$(t)-phenyl-SO$_2$- | -(CH$_2$)$_2$-[4-(NHCOCH(CH(CH$_3$)$_2$)-C$_6$H$_4$-]; with 2-C$_5$H$_{11}$(t), 4-C$_5$H$_{11}$(t) on NHCO-phenyl ring | H |
| 2-16 | 4-CF$_3$-phenyl-SO$_2$- | -(CH$_2$)$_3$-[4-(NHCOCH(C$_6$H$_{13}$))-C$_6$H$_4$-]; with 2-Cl, 4-C$_5$H$_{11}$(t) on NHCO-phenyl ring | H |
| 2-17 | -SO$_2$-C$_8$H$_{17}$ | -(CH$_2$)$_3$-[2-(NHCOCH(C$_{12}$H$_{25}$))-C$_6$H$_4$-]; with 2-C$_4$H$_9$(t), 4-OH on NHCO-phenyl ring | phenoxy |
| 2-18 | -COOH | -CH$_2$-[4-(NHCOCH(C$_4$H$_9$))-C$_6$H$_4$-]; with 2-C$_4$H$_9$(t), 4-C$_4$H$_9$(t) on NHCO-phenyl ring | pyrazolyl |
| 2-19 | -PO(OC$_2$H$_5$)$_2$ | -(CH$_2$)$_3$-[4-(NHCOCH(C$_{12}$H$_{25}$))-C$_6$H$_4$-]; with 4-NHSO$_2$C$_4$H$_9$ on NHCO-phenyl ring | H |

-continued
Formula [II]
| Coupler No. | $R_1$ | $R_3$ | X |
|---|---|---|---|
| 2-20 | 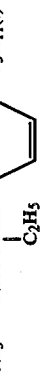 |  | H |
| 2-21 |  | 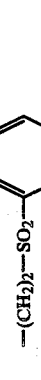 | Cl |
| 2-22 | —CN |  | Cl |
| 2-23 | —OCO(CF$_2$)$_{11}$H | 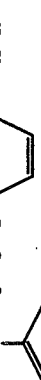 | Cl |
| 2-24 |  | 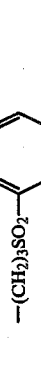 | Cl |

-continued

Formula [II]

$$\underset{R_1}{\overset{X}{\underset{N-N}{\bigg|}}}\hspace{-2pt}\underset{N}{\overset{H}{\underset{\|}{N}}}\hspace{-2pt}R_3$$

| Coupler No. | $R_1$ | $R_3$ | X |
|---|---|---|---|
| 2-25 | pentafluorophenyl-OSO$_2$– | 2,5-bis(OC$_8$H$_{17}$)phenyl with –CH$_2$CH$_2$CHSO$_2$–  group (C$_2$H$_5$) | H |
| 2-26 | 2-chlorophenyl-SO$_2$– | 3-chloro-4-(NHSO$_2$-(4-OC$_{12}$H$_{25}$phenyl))phenyl-NH– | H |
| 2-27 | 3-chloro-4-(NHCOC$_2$H$_5$)phenyl-SO$_2$– | –SC$_{18}$H$_{37}$ | H |
| 2-28 | –OCCF$_2$CF$_3$ (C=O) | 2-C$_5$H$_{11}$(t)-4-C$_5$H$_{11}$(t)phenyl-NHCOCHO-phenyl | Cl |
| 2-29 | –CON(C$_4$H$_9$)$_3$ | 4-(NHCOC$_{13}$H$_{27}$)phenyl-CH$_2$– | Cl |

-continued

Formula [II]

[Structure: pyrazolotriazole with R1, X, R3 substituents]

| Coupler No. | R₁ | X | R₃ |
|---|---|---|---|
| 2-30 | —SO₂N(C₂H₅)₂ | H | 4-OC₁₂H₂₅-phenyl |
| 2-31 | —Cl | Cl | 3-C₁₅H₃₁-phenyl-(CH₂)₃— |
| 2-32 | 2-Cl-phenyl-SO₂— | H | 2-OC₈H₁₇-5-C₅H₁₁(t)-phenyl with —CH₂CH₂SO₂—C(CH₃)₂CH₃ |
| 2-33 | —NHCO(CF₂)₅H | Cl | 4-[2-C₅H₁₁(t)-4-C₅H₁₁(t)-phenyl-NHCOCH(C₂H₅)—]-phenyl-SCH₂CH₂— |
| 2-34 | phenyl-SO₂— | Cl | 4-[3-C₄H₉(t)-4-OH-phenyl-NHCOCH(C₁₂H₂₅)—]-phenyl— |

-continued

Formula [II]:

$$\text{structure with } X, R_1, R_3 \text{ on pyrazolotriazole ring}$$

| Coupler No. | $R_1$ | $R_3$ | X |
|---|---|---|---|
| [II]-3-1 | $C_2H_5-SO_2-$ | 3-($t$-C$_4$H$_9$)-phenyl; NHCOCH(C$_{16}$H$_{33}$)-O-phenyl | H |
| [II]-3-2 | phenyl-SO$_2-$ | 4-OC$_{14}$H$_{29}$-phenyl; NHSO$_2$-phenyl | H |
| [II]-3-3 | 4-(C$_{11}$H$_{23}$SO$_2$NH)-phenyl-SO$_2-$ | $-CH(CH_3)-CH_2CH_2SO_2C_{15}H_{31}$ | H |
| [II]-3-4 | pentafluorophenyl-SO$_2-$ | 2-OCH$_3$, 5-OC$_4$H$_9$, with NHCOCH(C$_{12}$H$_{25}$)-(4-$t$-C$_8$H$_{17}$)phenyl | H |
| [II]-3-5 | $CF_3SO_2-$ | $-(CH_2)_2SO_2NHC_{18}H_{37}$ | Cl |
| [II]-3-6 | 4-CH$_3$O-phenyl-SO$_2-$ | $-CH(CH_2OC_8H_{17})$-(4-NHCOCH$_2$OC$_{16}$H$_{33}$)phenyl | H |

-continued

Formula [II]:

$$\underset{R_1}{\overset{X}{\underset{N-N}{\vphantom{X}}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \underset{}{\overset{H}{N}\!-\!N} \!\!=\!\! R_3$$

| Coupler No. | $R_1$ | $R_3$ | X |
|---|---|---|---|
| [II]-3-7 | 2,4-dichlorophenyl-SO$_2$- | 2-OC$_4$H$_9$-5-tC$_8$H$_{17}$-phenyl-(CH$_2$)$_3$SO$_2$- | Cl |
| [II]-3-8 | 1-naphthyl-SO$_2$- | -C$_{15}$H$_{31}$ | F |
| [II]-3-9 | tC$_4$H$_9$SO$_2$- | 2-OC$_4$H$_9$-5-tC$_8$H$_{17}$-phenyl-(CH$_2$)$_3$SO$_2$- | Br |
| [II]-3-10 | 3-chlorophenyl-SO- | 4-(4-C$_{16}$H$_{33}$-phenyl)-(CH$_2$)$_3$-phenyl-NHCOCH(C$_8$H$_{17}$)O- | Cl |
| [II]-3-11 | phenyl-CH$_2$CH$_2$SO- | 3-Cl-4-(4-OC$_{12}$H$_{25}$-phenyl-NHSO$_2$)-phenyl-NH- | pyrazol-1-yl |

-continued

Formula [II]

$$\begin{array}{c} X \\ | \\ R_1 \end{array} \diagdown \begin{array}{c} H \\ | \\ N-N \\ \| \\ N-N \end{array} \diagdown R_3$$

| Coupler No. | $R_1$ | $R_3$ | X |
|---|---|---|---|
| [II]-3-12 | 2,3,4,5,6-pentafluorophenyl-SO$_2$O— | 3-(phenyl-NHSO$_2$)-4-OC$_{12}$H$_{25}$-phenyl | H |
| [II]-3-13 | C$_8$H$_{17}$SO$_2$O— | 4-(NHSO$_2$-(4-OH-phenyl))-α-(O(CH$_2$)$_2$OC$_{12}$H$_{25}$)benzyl | Cl |
| [II]-3-14 | (C$_{12}$H$_{25}$)$_2$NSO$_2$— | 2-OC$_4$H$_9$-3-(phenyl-NHSO$_2$)-5-tC$_8$H$_{17}$-phenyl | phenoxy |
| [II]-3-15 | (C$_6$H$_5$)(C$_2$H$_5$)NSO$_2$— | —(CH$_2$)$_3$SO$_2$-(2-OC$_4$H$_9$-5-tC$_8$H$_{17}$-phenyl) | Cl |
| [II]-3-16 | (C$_6$H$_5$)$_2$PO— | —(CH$_2$)$_3$NHCOCH(C$_{12}$H$_{25}$)-O-phenyl | H |

-continued

Formula [II]

$$\begin{array}{c} X \\ | \\ R_1-C=C-NH \\ \phantom{R_1-}N\phantom{=C}N-R_3 \\ \phantom{R_1-C=C-}N \end{array}$$

| Coupler No. | $R_1$ | $R_3$ | X |
|---|---|---|---|
| [II]-3-17 | (tetrazolyl with Cl) | $-(CH_2)_2-C_6H_4-NHSO_2C_{18}H_{37}$ | Cl |
| [II]-3-18 | $C_2H_5CO-$ | $-CH_2CH_2CH_2SO_2-$ (2-OC$_4$H$_9$, 4-tC$_8$H$_{17}$ phenyl) | Cl |
| [II]-3-19 | $C_6H_5CO-$ | $-(CH_2)_3-$ (2-NHCOCHC$_{10}$H$_{21}$, 3-CH$_3$ phenyl) | N-pyrazolyl |
| [II]-3-20 | $HCF_2CF_2O-$ | $-C(CH_3)_2-CH_2SO_2C_{18}H_{37}$ | H |
| [II]-3-21 | $C_6F_5O-$ | (4-C$_{18}$H$_{37}$-phenyl)-NHSO$_2$-(phenyl) | Cl |
| [II]-3-22 | $HOOC-$ | $-(CH_2)_4SO_2-$(4-C$_{12}$H$_{25}$ phenyl) | H |

-continued

Formula [II]

$$\underset{R_1}{\overset{X}{\underset{N}{\bigwedge}}}\overset{H}{\underset{N-N}{\bigwedge}}R_3$$

| Coupler No. | R₁ | R₃ | X |
|---|---|---|---|
| [II]-3-23 | C₆H₅-SO₂CH₂— | 2-tC₄H₉-4-(NHCOCHC₁₂H₂₅ where CO bears OH position)... phenyl: 4-OH, 2-tC₄H₉, with NHCOCH(C₁₂H₂₅)— at position (see structure) | Br |
| [II]-4-1 | —CN | 2-OC₄H₉-5-tC₈H₁₇-phenyl-(CH₂)₃SO₂— | Cl |
| [II]-4-2 | —CN | —CHCH₂CH₂SO₂C₁₆H₃₃ with CH₃ branch | H |
| [II]-4-3 | —CN | 4-OC₁₂H₅-phenyl-(CH₂)₃NHSO₂— | H |
| [II]-4-4 | —CN | 4-(NHCOC₁₁H₂₃)-phenyl | H |
| [II]-4-5 | —O—C(=O)—CH₃ | 2-tC₅H₁₁-4-tC₅H₁₁-phenyl, NHCOCH(C₄H₉)O— | Cl |

-continued

Formula [II]

$$\text{structure with } R_1, X, R_3 \text{ on pyrazolo-triazole core}$$

| Coupler No. | $R_1$ | $R_3$ | X |
|---|---|---|---|
| [II]-4-6 | −OCOCH$_3$ | −(CH$_2$)$_3$SO$_2$− (2-OC$_4$H$_9$, 5-tC$_8$H$_{17}$ phenyl) | Cl |
| [II]-4-7 | −OCOC$_2$H$_5$ | 2-Cl, 4-(NHCOCHC$_8$H$_{17}$)-phenol | Cl |
| [II]-4-8 | −OCOC$_3$H$_7$ | −CH$_2$CH$_2$NHCOCH(C$_4$H$_9$)− (2-tC$_5$H$_{11}$, 4-tC$_5$H$_{11}$ phenyl) | Cl |
| [II]-4-9 | −OCOC$_3$H$_7$ | −CH(CH$_3$)CH$_2$SO$_2$C$_{18}$H$_{37}$ | pyrazol-1-yl |
| [II]-4-10 | −OCOC$_{12}$H$_{25}$ | 4-OCH$_3$-phenyl | H |
| [II]-4-11 | −COOCH$_3$ | −(CH$_2$)$_3$SO$_2$− (2-OC$_4$H$_9$, 5-tC$_8$H$_{17}$ phenyl) | Cl |

-continued

Formula [II]

$$\begin{array}{c} X \\ | \\ R_1 \end{array} \begin{array}{c} H \\ N-N \\ \parallel \\ N-N \end{array} R_3$$

| Coupler No. | $R_1$ | $R_3$ | $X$ |
|---|---|---|---|
| [II]-4-12 | —COOCH$_3$ | 2-chloro-4-(3-chloro-4-(CH$_2$CH$_2$CHO-C$_7$H$_{15}$)phenylsulfonyl)phenol | H |
| [II]-4-13 | —COOC$_2$H$_5$ | 3-tC$_4$H$_9$-phenyl-NHCOCHO-C$_{12}$H$_{25}$ | Cl |
| [II]-4-14 | —COOC$_6$H$_5$ | 2-tC$_5$H$_{11}$-5-tC$_5$H$_{11}$-phenyl-CH$_2$CH$_2$NHCOCHO-C$_5$H$_{11}$ | Br |
| [II]-4-15 | —COOC$_6$H$_5$ | —C(CH$_3$)$_2$CH$_2$SO$_2$C$_{18}$H$_{37}$ | H |
| [II]-4-16 | —COOCH$_2$C$_6$H$_5$ | 4-OC$_4$H$_9$-2-(CH$_2$)$_3$SO$_2$-phenyl-tC$_8$H$_{17}$ | H |
| [II]-4-17 | —COOCH$_2$C$_6$H$_5$ | 2-tC$_5$H$_{11}$-4-tC$_5$H$_{11}$-phenyl-NHCOCHO-C$_8$H$_{17}$ | H |

-continued

Formula [II]

$$\underset{R_1}{\overset{X}{\underset{N}{\bigvee}}}\overset{H}{\underset{N}{\bigvee}}\overset{N}{\underset{N}{\bigvee}}R_3$$

| Coupler No. | R₁ | R₃ | X |
|---|---|---|---|
| [II]-4-18 | —COOCH₂C₆H₅ | 4-[4-(4-hydroxyphenylsulfonyl)phenyl]-NHCOCH(C₁₀H₂₁)O(CH₂)₃— anilino group | Cl |
| [II]-4-19 | —COOCH₂C₆H₅ | 4-methyl-NHCOCH(CH₃)CH₂SO₂C₁₂H₂₅ anilino | Cl |
| [II]-4-20 | 3-(—COOCH₂—)-NHCOCH(C₁₁H₂₃)O-phenyl anilino | —CH₃ | H |
| [II]-4-21 | —CON(C₂H₅)₂ | 2-OC₄H₉-5-tC₈H₁₇-phenyl-(CH₂)₃SO₂— | Cl |
| [II]-4-22 | —CON(C₂H₅)₂ | 4-OC₁₂H₂₅-phenyl (methyl) | Cl |

-continued
Formula [II]
| Coupler No. | R₁ | R₃ | X |
|---|---|---|---|
| [II]-4-23 | —CON(C₂H₅)₂ |  | H |
| [II]-4-24 | —CON(CH₃)₂ |  | 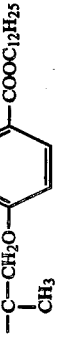 |
| [II]-4-25 | —CON(C₆H₅)₂ |  | Cl |
| [II]-4-26 | —CON(C₈H₁₇)₂ |  | H |
| [II]-4-27 | —CON(C₂H₅)(C₈H₁₇) | 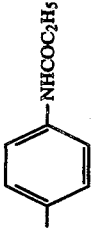 | Cl |
| 5-1 | —C₁₇H₃₅ | —SO₂CH₃ | H |
| 5-2 | —C₃H₇(i) | —SO₂C₁₈H₃₇ | Cl |

-continued

Formula [II]

$$\begin{array}{c} X \\ | \\ R_1-C=C-N \\ \phantom{XXX} | \phantom{X} \diagdown \\ \phantom{XXXX} N \phantom{X} N-H \\ \phantom{XXXXX} \diagdown \phantom{X} / \\ \phantom{XXXXXX} C \\ \phantom{XXXXXXX} | \\ \phantom{XXXXXXX} R_3 \end{array}$$

| Coupler No. | $R_1$ | $R_3$ | X |
|---|---|---|---|
| 5-3 | 2-$OC_4H_9$, 4-$C_8H_{17}(t)$-phenyl-$SO_2-$ | phenyl-$SO_2-$ | Cl |
| 5-4 | $-SO_2C_{18}H_{37}$ | 4-$CH_3$-phenyl-$SO_2-$ | Cl |
| 5-5 | $-SO_2N(C_{10}H_{21})_2$ | 4-$CF_3$-phenyl-$SO_2-$ | H |
| 5-6 | 2-$OC_4H_9$, 4-$C_8H_{17}(t)$-phenyl-$SO_2-$ | $-SO_2CF_3$ | pyrazolyl |
| 5-7 | 4-[-(CH$_2$)$_3$-phenyl-NHCOCH($C_{12}H_{25}$)-$SO_2$-phenyl-$SO_2$-4-OH-phenyl] | 4-Cl-phenyl-$SO_2-$ | Cl |
| 5-8 | $-CN$ | 3-Cl, 4-($NHCOC_{13}H_{27}$)-phenyl-$SO_2-$ | Cl |

-continued

Formula [II]

![structure](R1, X, N-N-H, N=N-R3)

| Coupler No. | R₁ | R₃ | X |
|---|---|---|---|
| 5-9 | pentafluorophenyl-SO₂- | —SO₂C₁₈H₃₇ | Cl |
| 5-10 | —OCOCH₂Cl | (2,4-di-t-C₅H₁₁ phenyl)-NHCOCH(C₂H₅)-O-(3-SO₂-phenyl)- | Cl |
| 5-11 | —NHCOCF₃ | —SOC₈H₁₇ | Br |
| 5-12 | —SO₂N(C₁₀H₂₁)₂ | —SOCH₂CH(CH₃)CH₂O-phenyl | phenoxy |
| 5-13 | —CH₃ | (3-C₁₅H₃₁-phenyl)-SO- | Br |
| 5-14 | —SO₂C₈H₁₇ | —SOCF₃ | H |
| 5-15 | —SO₂CH₂-phenyl | (2-Cl-4-C₁₅H₃₁-phenyl)-SO- | Cl |

-continued

Formula [II]

[structure: pyrazolotriazole core with X, R1, R3, NH]

| Coupler No. | R₁ | R₃ | X |
|---|---|---|---|
| 5-16 | 4-C₁₂H₂₅-C₆H₄-SO₂— | —PO(OC₂H₅)₂ | Cl |
| 5-17 | —CF₃ | —SO₂N(C₁₀H₂₁)₂ | 4-COOH-C₆H₄-O— |
| 5-18 | —SO₂C₁₈H₃₇ | —OCOCH₂Cl | Cl |
| 5-19 | 4-C₁₂H₂₅-C₆H₄-SO₂— | —OSO₂CF₃ | H |
| 5-20 | —CN | 2-OC₄H₉-5-C₈H₁₇(t)-C₆H₃-SO₂— | Cl |
| 5-21 | —SOC₃H₇ | 2-OC₄H₉-5-C₈H₁₇(t)-C₆H₃-SO— | Cl |
| 5-22 | —NO₂ | —NHCO(CF₂)₈H | Br |

-continued

Formula [II]:

structure with R1, X, N-N-H, N=N, R3

| Coupler No. | R1 | R3 | X |
|---|---|---|---|
| 5-23 | —Cl | —SO₂—C₆H₄—C₁₂H₂₅ | Cl |
| 5-24 | —F | —OCOC₁₁H₂₃ | Cl |
| [II]-6-1 | C₁₈H₃₇— | —SO₂CH₂—C₆H₄—NHSO₂—C₆H₄—OC₁₂H₂₅ | H |
| [II]-6-2 | CH₃— | —SO₂—C₆H₃(C₅H₁₁(t))—NHSO₂—C₆H₃(C₅H₁₁(t)) | Cl |
| [II]-6-3 | CH₃CONH—C₆H₄— | —SO₂CH₂—C₆H₄—NHSO₂—C₆H₃(OC₈H₁₇)(OC₈H₁₇) | H |
| [II]-6-4 | tC₄H₉— | —SO₂—C₆H₄—NHCOCHO(C₁₀H₂₁)—C₆H₄—SO₂—C₆H₄—OH | H |

-continued

Formula [II]

$$\text{Pyrazolotriazole with substituents } R_1, R_3, X$$

| Coupler No. | R₁ | R₃ | X |
|---|---|---|---|
| [II]-6-5 | cyclohexyl (with H) | 2,3,5,6-tetrafluoro-4-(—SO₂NHSO₂C₁₂H₂₅)phenyl | pyrazol-1-yl |
| [II]-6-6 | phenyl | 4-chloro-3-(—SO₂NHCOCH₂O-[2-(t)C₅H₁₁-4-(t)C₅H₁₁-phenyl])phenyl | Cl |
| [II]-6-7 | 4-[2-(t)C₅H₁₁-4-(t)C₅H₁₁-phenoxy]-OCH(C₂H₅)CONH-(4-methylphenyl) | —SO₂CF₃ | Br |
| [II]-6-8 | 4-chlorophenyl (with 4-methyl) | 4-(t)C₃H₁₁-2-C₅H₁₁(t)-phenyl-SO₂(CH₂)₃O— | phenoxy (—OC₆H₄—OCH₃) |
| [II]-6-9 | CH₃SO₂NH— | 4-(tC₈H₁₇)-2-(OC₄H₉)phenyl-SO₂— | H |

-continued

Formula [II]:

$$\begin{array}{c} R_1-\underset{N-N}{\overset{X}{\diagdown}}\!\!\!=\!\!\!\underset{N}{\overset{H}{\diagdown}}\!\!-\!\!N\!=\!\!\underset{N}{\overset{R_3}{\diagdown}} \end{array}$$

| Coupler No. | R$_1$ | R$_3$ | X |
|---|---|---|---|
| [II]-6-10 | (i)C$_3$H$_7$— | 2-Cl-4-(NHSO$_2$C$_{16}$H$_{33}$)phenyl-SO$_2$— | Cl |
| [II]-6-11 | (t)C$_4$H$_9$— | 4-[2,4-di(t)C$_5$H$_{11}$-phenyl-NHSO$_2$]phenyl-SO$_2$— | H |
| [II]-6-12 | C$_6$H$_5$— | 4-OC$_{12}$H$_{25}$-phenyl-SOCH$_2$CH$_2$— | Cl |
| [II]-6-13 | CH$_3$— | —OSO$_2$C$_{18}$H$_{37}$ | H |
| [II]-6-14 | (C$_2$H$_5$)(CH$_3$)$_2$C— | —OSO$_2$C$_{18}$H$_{37}$ | Cl |
| [II]-6-15 | 4-(C$_{11}$H$_{23}$CONH)phenyl- | 3-OSO$_2$-(3-OC$_{12}$H$_{25}$-phenyl-NHCOCHC$_8$H$_{17}$)phenyl | H |
| [II]-6-16 | (t)C$_4$H$_9$— | —SO$_2$N(C$_{14}$H$_{29}$)$_2$ | Cl |
| [II]-6-17 | C$_6$H$_5$— | —SO$_2$N(C$_2$H$_5$)(C$_8$H$_{17}$) | H |

-continued
Formula [II]
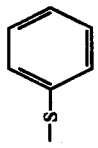
| Coupler No. | R₁ | R₃ | X |
|---|---|---|---|
| [II]-6-18 | 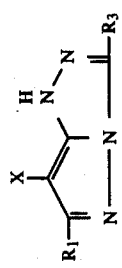 CH₃CONH— | 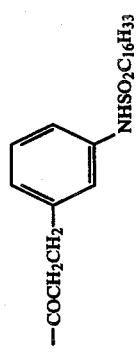 | H |
| [II]-6-19 | (i)C₃H₇— | | 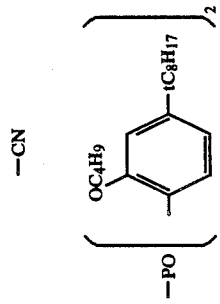 —S— |
| [II]-6-20 | C₁₈H₃₇— | —COCH₂CH₂— 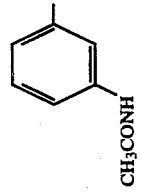 NHSO₂C₁₆H₃₃ | Cl |
| [II]-6-21 | (i)C₃H₇— | —CN | Cl |
| [II]-6-22 | C₈H₁₇S— | —PO— 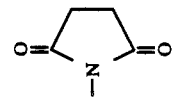 | |
| [II]-6-23 | C₁₅H₃₁— | —PO(OC₂H₅)₂ | |

-continued

Formula [II]

[Structure: pyrazolo-triazole with X, R₁, R₃ substituents]

| Coupler No. | R₁ | R₃ | X |
|---|---|---|---|
| [II]-6-24 | (i)C₃H₇— | 2,5-bis(C₈H₁₇)-pyrrol-1-yl | Cl |
| [II]-6-25 | 4-CH₃-C₆H₄— | —CON(C₁₁H₂₃)₂ | Cl |
| [II]-6-26 | (t)C₄H₉— | —CON(C₂H₅)(C₁₂H₂₅) | H |
| [II]-6-27 | (i)C₃H₇— | 4-(NHSO₂C₁₈H₃₇)-2,3,5,6-tetrafluorophenoxy | Cl |
| [II]-6-28 | 2-(t)C₅H₁₁-4-(t)C₅H₁₁-phenyl-O-CH(C₂H₅)-CONH-(3-CH₃-C₆H₄) | —O(CF₂)₈H | H |
| [II]-6-29 | 4-(4-HO-C₆H₄-SO₂)-phenyl-O-CH(C₁₀H₂₁)-CONH-(4-(CH₂)₃-C₆H₄)— | —Cl | Cl |

-continued

Formula [II]:

structure: pyrazolotriazole with R₁, X, R₃ substituents

| Coupler No. | R₁ | R₃ | X |
|---|---|---|---|
| [II]-6-30 | 2-(2,4-di-(t)C₅H₁₁-phenoxy)-C₄H₉-OCHCONH- | —NO₂ | H |
| [II]-6-31 | CH₃— | —SO₂NH(C₁₂H₂₅) | H |
| [II]-6-32 | (i)C₃H₇— | 4-OC₁₈H₃₇-phenyl-CONH— | Cl |
| [II]-7-1 | —SO₂CH₃ | —SO₂CH₃ | H |
| [II]-7-2 | C₆H₅—SO₂— | 4-NHSO₂C₁₄H₂₉-phenyl-SO₂— | H |
| [II]-7-3 | C₆H₅—SO₂— | —OCC₁₄H₂₉ (—O—C(=O)—C₁₄H₂₉) | H |
| [II]-7-4 | C₆H₅—SO₂— | 3-NHCOC₁₄H₂₉-phenyl-OSO₂— | H |
| [II]-7-5 | C₆F₅—SO₂— | 2-Cl-4-OC₁₂H₂₅-phenyl-SO₂— | H |

-continued

Formula [II]

$$\underset{R_1}{\overset{X}{\underset{N}{\bigvee}}}\overset{H}{\underset{N-N}{\bigvee}}R_3$$

| Coupler No. | R₁ | R₃ | X |
|---|---|---|---|
| [II]-7-6 | —SO₂N(C₂H₅)₂ | 3-(NHCOC₁₄H₂₉)-C₆H₄-CH₂SO₂— | Cl |
| [II]-7-7 | C₆H₅—SO— | 3-(SO—)-C₆H₄—NHCOCH(C₁₂H₂₅)—O—C₆H₄—C₈H₁₇(4) | Cl |
| [II]-7-8 | —CN | 4-(NHCOC₁₃H₂₇)-3-Cl-C₆H₃—SO₂— | pyrazol-1-yl |
| [II]-7-9 | 3-Cl-4-(SO₂—)-C₆H₃—OC₁₂H₂₅ | 3-(SO₂—)-C₆H₄—NHCOCH(C₂H₅)—(2,5-di-tC₅H₁₁-C₆H₃O)— | Cl |

-continued

Formula [II]:

$$\underset{R_1}{\overset{X}{\underset{N=N}{\bigvee}}}\overset{H}{\underset{N-N}{\bigvee}}R_3$$

| Coupler No. | $R_1$ | $R_3$ | X |
|---|---|---|---|
| [II]-7-10 | —$CF_3$ | (3-sulfonamidophenyl group with —$SO_2$— linked to 2,5-di-t$C_5H_{11}$ phenyl bearing —NHCOCHO—$C_2H_5$) | H |
| [II]-7-11 | pentafluorophenoxy (—O—$C_6F_5$) | —C(=O)—N($C_{12}H_{25}$)$_2$ | Cl |
| [II]-7-12 | 4-$C_{12}H_{25}$-phenyl-$SO_2$— | —PO(O$C_2H_5$)$_2$ | H |
| [II]-7-13 | —Cl | —$SO_2(CF_2)_{11}$H | Cl |
| [II]-7-14 | —O$SO_2CF_3$ | —O$(CF_2)_{12}$H | Cl |
| [II]-7-15 | (4-t$C_8H_{17}$-2-O$C_4H_9$-phenyl)—$SO_2$— | —$SO_2N(C_4H_9)_2$ | Cl |
| [II]-7-16 | —CON($C_4H_9$)$_2$ | —CO$(CF_2)_8$H | 4-methoxyphenyl |

-continued

Formula [II]:

structure with X, R₁, R₃ on a pyrazolo-triazole ring system (X, N-N, N=N, R₁, R₃, NH)

| Coupler No. | R₁ | R₃ | X |
|---|---|---|---|
| [II]-7-17 | —C(=O)—CF₃ | 4-Cl-3-(—SO₂—)-phenyl-NHCOC₁₄H₂₉ | Cl |
| [II]-7-18 | —SO₂CF₃ | 2,3,5,6-tetrafluoro-4-phenoxyphenyl with NHCOCH(—O—C₆H₅)—C₁₂H₂₅ | 4-CH₃-phenyl-S— |
| [II]-7-19 | pyrrol-1-yl (N-pyrrolyl) | 4-OC₄H₉-3-(—SO—)-phenyl-tC₈H₁₇ | Cl |
| [II]-7-20 | 2,4-di(tC₅H₁₁)-phenyl with NHCOCH(C₂H₅)-(3-SO₂-phenyl) | 2-Cl-(—SO₂—)-phenyl | H |

-continued

Formula [II]

| Coupler No. | R₁ | R₃ | X |
|---|---|---|---|
| [II]-7-21 | —SO₂C₁₀H₂₁ | 4-tC₈H₁₇-2-(—SO₂—)-1-OC₄H₉ phenyl | H |
| [II]-7-22 | 4-(NHSO₂C₄H₉)-phenyl-SO₂CH₂— | 4-C₁₂H₂₅-2-Cl-1-(—SO₂—) phenyl | H |
| [II]-7-23 | pentafluorophenyl-NHSO₂C₁₄H₂₉ with C(=O)— | —SO₂C₁₀H₃₇ | Cl |
| [II]-7-24 | —COOH | (4-tC₈H₁₇-2-OC₄H₉-phenyl-O—)₂PO— | Cl |
| [II]-7-25 | pentafluorophenyl-SO₂— | 4-NHCOC₁₄H₂₉-2-Cl-1-C(=O)— | H |

-continued

Formula [II]:

$R_1$—[pyrazolotriazole ring with NH, N, N, N, X, $R_3$]

| Coupler No. | $R_1$ | $R_3$ | X |
|---|---|---|---|
| [II]-7-26 | —NHCOCF$_3$ | 4-Cl-3-SO$_2$-phenyl-NHCOCH(C$_{12}$H$_{25}$)O-(4-hydroxyphenyl) | Cl |
| [II]-7-27 | —SO$_2$N(C$_{10}$H$_{21}$)$_2$ | 4-CF$_3$-phenyl-SO$_2$— | H |

Formula [III]

structure: pyrazolotriazole with substituents X, R₁, R₄

| Coupler No. | R₁ | R₄ | X |
|---|---|---|---|
| [III]-1-1 | CF₃— | | H |
| [III]-1-2 | (C₂H₅)₂N—NCO— | 4-tC₈H₁₇-2-(-(CH₂)₃SO₂-)-phenyl with OC₄H₉ | pyrazolyl (N-N) |
| [III]-1-3 | tC₄H₉ | 4-OC₁₂H₂₅-phenyl-CH(CH₃)CH₂CH₂SO₂— | Cl |
| [III]-1-4 | CH₃— | 4-(4-tC₄H₉-phenyl-NHCOCHO(C₁₂H₂₅))-phenyl-CO-; with —CO(CH₂)₃SO₂— and tC₅H₁₁, OC₈H₁₇ | 4-CH₃-phenyl-O— |
| [III]-1-5 | cyclohexyl-H | 2,4-di-tC₅H₁₁-phenyl-NHCOCHO-C(CH₃)₂CH₃ on 2,3,5,6-tetrafluorophenyl | 4-HO-phenyl-S— |

-continued

Formula [III]

| Coupler No. | $R_1$ | $R_4$ | X |
|---|---|---|---|
| [III]-1-6 | (C$_{12}$H$_{25}$)$_2$NCO— | —(CH$_2$)$_3$—C$_6$H$_3$(C$_5$H$_{11}$(t))$_2$-NHCOCHO-C$_5$H$_{11}$(t) | H |
| [III]-1-7 | CF$_3$— | 2-Cl-C$_6$H$_4$-NHCOCH(C$_{12}$H$_{25}$)— | Cl |
| [III]-1-8 | C$_6$H$_5$NHCOO— | 4-CH$_3$-C$_6$H$_4$-NHCOCH(C$_2$H$_5$)-C$_6$H$_4$-C$_{15}$H$_{31}$ | H |
| [III]-1-9 | CH$_3$C(O)O— | —CH(C$_2$H$_5$)CH$_2$CH$_2$SO$_2$-C$_6$H$_4$-OC$_{16}$H$_{33}$ | H |
| 2-35 | C$_6$H$_5$SO$_2$— | 4-CH$_3$-C$_6$H$_4$-NHSO$_2$-C$_6$H$_4$-OC$_{12}$H$_{25}$ | H |
| 2-36 | —OSO$_2$CF$_3$ | —(CH$_2$)$_3$-C$_6$H$_3$(C$_4$H$_9$(t))-OH-NHCOCH(C$_{12}$H$_{25}$) | Cl |

-continued

Formula [III]

$$\begin{array}{c} X \\ | \\ R_1 - C = C - NH - R_4 \\ | \quad\quad | \\ N \quad\quad N \\ \diagdown N \diagup \end{array}$$

| Coupler No. | $R_1$ | $R_4$ | X |
|---|---|---|---|
| 2-37 | 2-chlorophenyl-SO$_2$– | –NHCOCHO(C$_4$H$_9$)-phenyl with C$_5$H$_{11}$(t) substituents | Cl |
| 2-38 | –SO$_2$–C$_{13}$H$_{37}$ | 4-OC$_{12}$H$_{25}$-phenyl | Cl |
| 2-39 | –PO(C$_8$H$_{17}$)$_2$ | –CH$_2$-(4-methylphenyl)-NHCOCHO(C$_{10}$H$_{21}$)-(3-Cl,4-SO$_2$-(3-Cl-4-OH-phenyl))phenyl | Cl |
| 2-40 | –C(CF$_3$)$_3$ | –(CH$_2$)$_3$-phenyl-NHCOCHO(C$_6$H$_{13}$)-(2-C$_5$H$_{11}$(t),4-C$_5$H$_{11}$(t))phenyl | Cl |
| 2-41 | –SO$_2$N(C$_2$H$_5$)$_2$ | –(4-methylphenyl)-NHCOCHO(C$_{10}$H$_{21}$)-(4-NHSO$_2$-(4-OH-phenyl))phenyl | Cl |
| 2-42 | –CO(CF$_2$)$_3$H | –(CH$_2$)$_3$O-phenyl-NHCOCHO(C$_{10}$H$_{21}$)-(3-Cl,4-SO$_2$-(3-Cl-4-OH-phenyl))phenyl | H |

-continued

Formula [III]

$$\text{structure with } R_1, X, R_4, \text{ and } N-N-N \text{ ring with NH}$$

| Coupler No. | $R_1$ | $R_4$ | X |
|---|---|---|---|
| 2-43 | pentafluorophenyl-SO$_2$- | 4-[4-(NHCOCHC$_{10}$H$_{21}$)phenyl-SO$_2$-]phenyl with OH | H |
| 2-44 | 2-chlorophenyl-SO$_2$- | -(CH$_2$)$_3$SO$_2$-(2-OC$_4$H$_9$-4-C$_8$H$_{17}$(t))phenyl | H |
| 2-45 | -PO(OC$_2$H$_5$)$_2$ | -(CH$_2$)$_3$NHSO$_2$-(2-OC$_8$H$_{17}$-4-C$_8$H$_{17}$(t))phenyl | H |
| 2-46 | 2-chlorophenyl-SO$_2$- | -C(CH$_3$)$_2$-CH$_2$CH$_2$NHCOCH(C$_{12}$H$_{25}$)-(3-NHSO$_2$-(2-OC$_8$H$_{17}$-5-C$_8$H$_{17}$(t))phenyl)phenyl | phenoxy |
| 2-47 | -CN | -(CH$_2$)$_3$O-(3-C$_{15}$H$_{31}$)phenyl | Cl |

-continued

Formula [III]

| Coupler No. | $R_1$ | $R_4$ | X |
|---|---|---|---|
| 2-48 | $-OC(CF_2)_4H$ | 3-Cl-4-OH-phenyl-SO$_2$-(3-Cl-4-(NHCOCHC$_{12}$H$_{25}$)phenyl)-(4-methylphenyl) | Cl |
| 2-49 | $-CON(C_4H_9)_2$ | 2,4-di-C$_5$H$_{11}$(t)-phenyl-NHCOCHC$_{12}$H$_{25}$-O-(CH$_2$)$_3$- | Cl |
| 2-50 | $-OSO_2(CF_2)_6H$ | 4-CN-phenyl-NHCOCHC$_{12}$H$_{25}$-(CH$_2$)$_3$- | Cl |
| 2-51 | $-O(CF_2)_{11}H$ | 2-C$_5$H$_{11}$(t)-4-C$_5$H$_{11}$(t)-phenyl-NHCO(CH$_2$)$_3$O-(CH$_2$)$_3$- | H |
| 2-52 | $-COCF_3$ (with C=O) | $-C(CH_3)_2-CH_2CH_2SO_2C_{16}H_{33}$ | pyrazolyl |
| 2-53 | 2-Cl-phenyl-OCO- | $-CH(CH_3)-CH_2CH_2SO_2$-(4-OC$_{12}$H$_{25}$)phenyl | Cl |

-continued
Formula [III]
| Coupler No. | R₁ | R₄ | X |
|---|---|---|---|
| 2-54 | 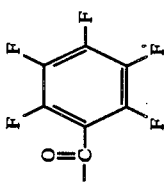 | 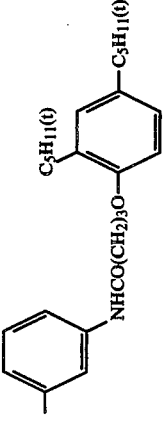 | H |
| 2-55 | 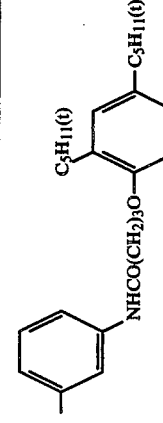 | 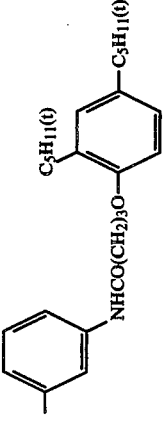 | Cl |
| 2-56 | 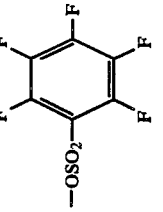 | 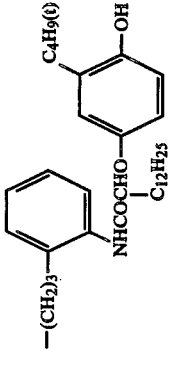 | H |
| 2-57 |  | 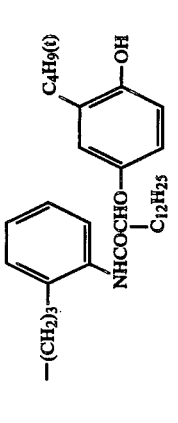 | Cl |
| [III]-3-1 | 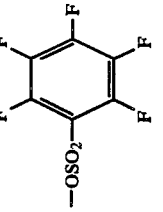 | 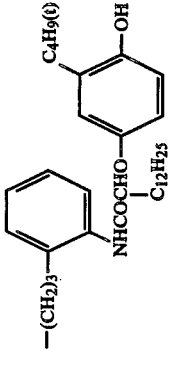 | Cl |

-continued

Formula [III]

| Coupler No. | R₁ | R₄ | X |
|---|---|---|---|
| [III]-3-2 | C₆H₅SO₂— | 2-OC₄H₉, 4-tC₈H₁₇-phenyl with NHCOCHO-C₁₂H₂₅ | Cl |
| [III]-3-3 | C₆F₅SO₂— | 2-OC₈H₁₇, 4-tC₈H₁₇-phenyl-(CH₂)₂NHSO₂— | H |
| [III]-3-4 | —C₁₈H₃₇SO₂— | 4-OC₁₂H₂₅-phenyl-NHSO₂-(4-CH₃-phenyl) | Cl |
| [III]-3-5 | 4-CH₃O-phenyl-CH₂SO₂— | 2,4-di-CH₃-6-CH₃-phenyl with NHCOCHO-C₂H₅, tC₅H₁₁, tC₅H₁₁ | Cl |
| [III]-3-6 | 2-OC₄H₉, 4-tC₈H₁₇-phenyl-SO₂— | 2-OC₄H₉, 4-tC₈H₁₇-phenyl-(CH₂)₃SO₂— | Cl |

-continued

Formula [III]

[Structure: pyrazolotriazole core with R1, R4, X substituents and NH group]

| Coupler No. | R1 | R4 | X |
|---|---|---|---|
| [III]-3-7 | 4-HO-C6H4-SO2- | -CHCH2CH2SO2C18H37 with CH3 | H |
| [III]-3-8 | 4-CH3-C6H4-SO2- | -CH2CH2NHSO2-(2-OC18H37, 5-tC8H17-phenyl) | Cl |
| [III]-3-9 | CH3SO2- | -CH2CH2NHCOCHO(C12H25)-phenyl-NHSO2-(2-OC8H17, 5-tC8H17-phenyl) | Cl |
| [III]-3-10 | cyclohexyl-SO2- | 4-Cl, 3-(4-OC12H25-phenyl-NHSO2)-phenyl-NH- | -NHCOCF3 |
| [III]-3-11 | CF3SO- | 2-tC4H9, 4-OH, 5-(NHCOCHO(C12H25)-p-tolyl)-phenyl | Br |

-continued

Formula [III]

$$\begin{array}{c} X \\ | \\ R_1 \end{array} \begin{array}{c} H \\ | \\ N \end{array} \begin{array}{c} R_4 \\ | \\ N \end{array}$$

| Coupler No. | R₁ | R₄ | X |
|---|---|---|---|
| [III]-3-12 | 4-CH₃-C₆H₄-SO- | —(CH₂)₃O—C₆H₄—NHCOCHO(C₁₂H₂₅)(2-Cl-C₆H₄) | Cl |
| [III]-3-13 | CF₃SO₂O— | —CH(CH₂CH₂)CH₃ phenyl-NHCOCHO(C₁₀H₂₁)(4-(4-OH-C₆H₄)SO₂-C₆H₄) | Cl |
| [III]-3-14 | 4-CH₃O-C₆H₄-SO₂O— | 4-OC₁₂H₂₅-C₆H₄-NHSO₂- phenyl | Cl |
| [III]-3-15 | (C₄H₉)₂NSO₂— | 4-CH₃-C₆H₄-NHSO₂C₁₈H₃₇ | Cl |
| [III]-3-16 | (C₂H₅)₂NSO₂— | —CH₂—C₆H₄—NHCOCHO(C₁₀H₂₁)(4-(4-OH-C₆H₄)SO₂-C₆H₄) | H |
| [III]-3-17 | (C₂H₅O)₂PO— | —(CH₂)₃SO₂—C₆H₄—NHCOCHO(C₂H₅)(3-OC₁₂H₂₅-C₆H₄) | H |

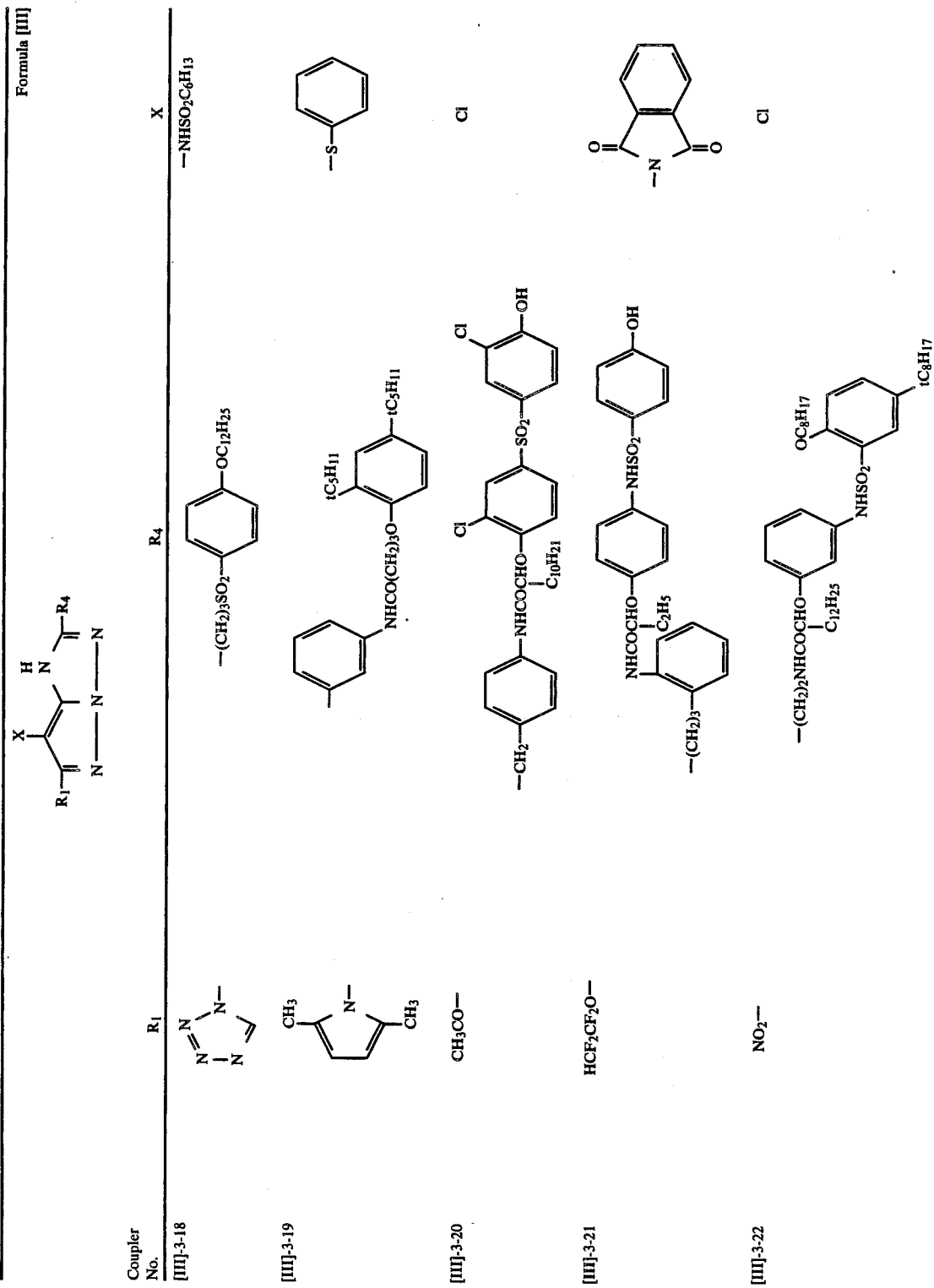

-continued

Formula [III]:

structure showing pyrazolotriazole core with R1, R4, X, and NH substituents

| Coupler No. | R1 | R4 | X |
|---|---|---|---|
| [III]-3-23 | phenyl-CH$_2$CH$_2$-SO$_2$CH$_2$- | -C$_{15}$H$_{31}$ | -O-phenyl |
| [III]-3-24 | HOOC- | -NHCOCHO(C$_4$H$_7$)-(2-tC$_5$H$_{11}$, 4-tC$_5$H$_{11}$)phenyl | Cl |
| 5-25 | pentafluorophenyl-SO$_2$- | -SO$_2$C$_{18}$H$_{37}$ | Cl |
| 5-26 | -NHCOC$_3$F$_7$ | -SO$_2$C$_{18}$H$_{37}$ | Br |
| 5-27 | phenyl-SO$_2$CH$_2$- | -(2-SO$_2$-, 4-C$_8$H$_{17}$(t), OC$_4$H$_9$)phenyl | Cl |
| 5-28 | -CF$_3$ | -(4-C$_{12}$H$_{25}$)phenyl-SO- | Cl |
| 5-29 | -SO$_2$CH$_3$ | -PO(OC$_8$H$_{17}$)$_2$ | H |

-continued

Formula [III]

[Structure: pyrazolotriazole with R₁, R₄, X substituents]

| Coupler No. | R₁ | R₄ | X |
|---|---|---|---|
| 5-30 | C₆H₅—SO₂— | —SO₂N(C₁₀H₂₁)₂ | [imidazole with two CH₃ groups] |
| 5-31 | —NO₂ | —SO₂C₁₈H₃₇ | Cl |
| 5-32 | —Cl | —OCOC₁₁H₂₃ | Cl |
| 5-33 | —F | | H |
| 5-34 | 4-OC₄H₉, 2-SO₂— (phenyl with C₈H₁₇(t)) | 4-OC₄H₉, 2-SO₂— (phenyl with C₈H₁₇(t)) | Cl |
| 5-35 | C₁₅H₃₁-phenyl-SO— | —OSO₂CF₃ | Cl |

Note: 5-34 R₄ is —SO₂CF₃

-continued

Formula [III]

$$\underset{R_1}{\underset{|}{\overset{X}{\underset{\|}{C}}}}\overset{H}{\underset{N-N}{\overset{|}{C}}}\overset{R_4}{\underset{\|}{C}}$$

| Coupler No. | $R_1$ | $R_4$ | X |
|---|---|---|---|
| 5-36 | CN | 3-($SO_2$-phenyl) with NHCOCHO($C_2H_5$) linked to 2-$C_5H_{11}(t)$, 4-$C_5H_{11}(t)$ phenyl | Cl |
| 5-37 | —OCOCH$_2$Cl | 2-Cl, 4-$C_{14}H_{29}$ phenyl-$SO_2$— | Cl |
| [III]-7-1 | phenyl-$SO_2$— | 3-NHCOC$_{14}H_{29}$ phenyl-$SO_2$— | H |
| [III]-7-2 | phenyl-$SO_2$— | 3-OCH$_3$ phenyl with NHCOCH($C_{12}H_{25}$)—O—(3-tC$_4H_9$ phenyl) | H |
| [III]-7-3 | 4-$C_{12}H_{25}$ phenyl-$SO_2$— | —SC$_2$C$_{18}H_{37}$ | H |

-continued

Formula [III]

$$\underset{R_1}{\overset{X}{\diagdown}}\!\!\!\!\!\!\!\!\!\!\!\!\!\!\!\!\!\!\underset{N-N}{\overset{H}{\underset{N}{\diagdown}}}\!\!\!\!\!\!\!\!\!\!\!\!\!\!\!\!\!\!\!\!\!\!\!\!\!\!\!\!\!R_4$$

| Coupler No. | $R_1$ | $R_4$ | X |
|---|---|---|---|
| [III]-7-4 | $-SO_2-CH_3$ | 3-($NHCOC_{14}H_{29}$)phenyl-$SO_2CH_2-$ | Cl |
| [III]-7-5 | phenyl-$SO_2CH_2-$ | 4-Cl-3-($NHCOC_{14}H_{29}$)phenyl-$OSO_2-$ | H |
| [III]-7-6 | $-CON(C_2H_5)_2$ | 3-($SO_2$-(3-tC$_4$H$_9$-phenyl))phenyl-NHCOCH-$C_{12}H_{25}$ | H |
| [III]-7-7 | $-SO_2N(C_3H_7)_2$ | 4-Cl-3-($NHCOC_{12}H_{25}$)phenyl-C(=O)- | H |
| [III]-7-8 | $-CN$ | 3-($NHCOC_{14}H_{29}$)phenyl-$SO_2-$ | Cl |

-continued

Formula [III]:

$$\underset{R_1}{\overset{X}{\diagdown}}\!\!\!\underset{N}{\diagup}\!\!\!\underset{N}{\diagdown}\!\!\!\underset{N}{\diagup}\!\!\!\underset{H}{\overset{R_4}{\diagup}}$$

| Coupler No. | R$_1$ | R$_4$ | X |
|---|---|---|---|
| [III]-7-9 | 3-(phenylsulfonyl)phenyl-NHCOCH(C$_{12}$H$_{25}$)-O-phenyl | —CON(C$_4$H$_9$)$_2$ | phenoxy |
| [III]-7-10 | pentafluorophenyl-SO$_2$— | 4-Cl-3-(NHCOC$_{13}$H$_{27}$)-phenyl-SO$_2$— | H |
| [III]-7-11 | —NHCOC$_3$F$_7$ | 4-Cl-3-(NHCOC$_{16}$H$_{33}$)-phenyl-SO$_2$— | Cl |
| [III]-7-12 | —SO$_2$CF$_3$ | —PO(OC$_8$H$_{17}$)$_2$ | H |
| [III]-7-13 | 1-methyl-5-chloro-1,2,3-triazol-4-yl | —O(CF$_2$)$_{15}$H | Cl |
| [III]-7-14 | —O—C(=O)(CF$_2$)$_{11}$H | 3-Cl-4-(C$_{14}$H$_{29}$)-phenyl-SO$_2$— | Cl |

-continued

Formula [III]

| Coupler No. | R₁ | R₄ | X |
|---|---|---|---|
| [III]-7-15 | —COCF₃ | 2,3,5,6-tetrafluoro-4-(NHCOC₁₄H₂₉)phenylsulfonyl | Cl |
| [III]-7-16 | —Cl | —COOC₁₁H₂₁ | phenylthio |
| [III]-7-17 | phenylsulfonyl | 2,3,5,6-tetrafluoro-4-methoxyphenyl-NHCOCH(C₄H₉)-O-(3-chlorophenyl) | pyrazolyl |
| [III]-7-18 | 3-chlorophenylsulfinyl | 3-(phenylsulfinyl)phenyl-NHCOCH(C₃H₇)-O-(4-chlorophenyl) | H |
| [III]-7-19 | pentafluorophenylsulfonyl | 4-chloro-3-(SO₂)-phenyl-NHCOC₁₄H₂₉ | H |

-continued

Formula [III]

| Coupler No. | $R_1$ | $R_4$ | X |
|---|---|---|---|
| [III]-7-20 | $-OSO_2(CF_2)_{10}H$ | $(CH_2)_6H$, pyrrole with $(CH_2)_6H$ | Cl |
| [III]-7-21 | $-CF(CF_3)_2$ | tetrafluorophenyl with $OCOC_{12}H_{25}$ and $-C(=O)-$ | Cl |
| [III]-7-22 | $-COOCF_3$ | phenyl-$NHCOCHO(C_{10}H_{21})$-phenyl-$C(=O)-$ | Cl |
| [III]-7-23 | $-COOC_{12}H_{25}$ | $-SO_2-$phenyl-$C_{12}H_{25}$ | H |

Formula [IV]

$$\text{[IV]: pyrazole structure with } R_1, R_5, R_6, X, \text{ and NH}$$

| Coupler No. | R₁ | R₅ | R₆ | X |
|---|---|---|---|---|
| [IV]-1-1 | C₁₇H₃₅— | —CH₃ | —CN | N-methylphthalimide group |
| [IV]-1-2 | CF₃— | —H | 4-(—O(CH₂)₃—)-phenyl-NHCOCH(C₁₂H₂₅)-(2-Cl) | H |
| [IV]-1-3 | (C₁₂H₂₅)(C₁₂H₂₅)N—CO— | —C₂H₅ | 2,4-di-tC₅H₁₁-phenyl-O(CH₂)₃NHCO(CH₂)₃— | Cl |
| [IV]-1-4 | tC₄H₉— | —CO— | —CH₃ | H |
| [IV]-1-5 | C₂H₅— | —COCH₂CH₂— | —C₁₈H₃₇ | phenoxy (—O—C₆H₅) |

-continued

Formula [IV]

| Coupler No. | $R_1$ | $R_5$ | $R_6$ | X |
|---|---|---|---|---|
| [IV]-1-6 | $C_{16}H_{33}OC(O)-$ | H | $-(CH_2)_3SO_2$-(4-tC$_8$H$_{17}$, 2-OC$_4$H$_9$-phenyl) | Cl |
| [IV]-1-7 | $CH(C_7H_{15})_2$ | H | $-COOCH_3$ | H |
| 2-58 | $C_6H_5-SO_2-$ | phenyl-$CH_2-$ | 4-[$CH(C_{10}H_{21})$NHCOCH$-$(2,4-di-tC$_5$H$_{11}$-phenoxy)]phenyl, $-(CH_2)_3-$ | Cl |
| 2-59 | pentafluorophenyl-$SO_2-$ | H | 4-[$CH(C_2H_5)$NHCOCH$-$(2,4-di-tC$_5$H$_{11}$-phenoxy)]phenyl, $-CH_3$ | H |
| 2-60 | 2-chlorophenyl-$OSO_2-$ | H | 3-[$CH(C_2H_5)$NHCOCH$-$(2,4-di-tC$_5$H$_{11}$-phenoxy)]phenyl, $-CH_3$ | Cl |

-continued

Formula [IV]

$$\begin{array}{c} X \\ | \\ R_1 \end{array} \begin{array}{c} H \\ | \\ N \end{array} \begin{array}{c} R_5 \\ | \\ R_6 \end{array}$$

| Coupler No. | $R_1$ | $R_5$ | $R_6$ | X |
|---|---|---|---|---|
| 2-61 | $-SO_2N(C_2H_5)_2$ | H | ![4-(4-hydroxyphenylsulfonyl)phenyl with NHCOCH($C_4H_9$)O-(CH$_2$)$_3$- substituent] | Cl |
| 2-62 | $-NHCO(CF_2)_8H$ | ![2-chloro-phenyl with $C_{12}H_{25}$-NHCOCHO- on 4-methylphenyl] | $-CH_3$ | Cl |
| 2-63 | ![2-chlorophenylsulfonyl] | $-CH_3$ | ![3-$C_{15}H_{31}$-phenyl-O-(CH$_2$)$_3$-] | H |
| [IV]-3-1 | $CH_3SO_2-$ | — | H | H |
| [IV]-3-2 | ![phenylsulfonyl] | –H | ![2,4-di-tC$_5$H$_{11}$-phenyl with NHCOCH($C_{10}H_{21}$)O- on 4-(CH$_2$)$_3$-phenyl-$C_{18}H_{37}$] | H |
| [IV]-3-3 | ![4-chlorobenzyl-CH$_3$SO$_2$-] | $-CH_2CH_3$ | ![3-$C_{15}H_{31}$-phenyl-O-(CH$_2$)$_3$-] | Cl |

-continued

Formula [IV]

| Coupler No. | $R_1$ | $R_5$ | $R_6$ | X |
|---|---|---|---|---|
| [IV]-3-4 | C8H17SO2NH—⟨phenyl-SO2—⟩ | —(CH2)3NHSO2—⟨phenyl with OC8H17 and tC8H17⟩ | H | —O—⟨phenyl⟩ |
| [IV]-3-5 | ⟨phenyl with OC4H9 and tC8H17⟩—SO— | —NHCOCHO(C2H5)—⟨phenyl with C11H23 and phenyl⟩ | H | Cl |
| [IV]-3-6 | CH3SO2O— | —H | —NHCOCHO(C2H5)—⟨phenyl with tC5H11⟩ | ⟨succinimide-S⟩ |
| [IV]-3-7 | (C2H5)2NSO2— | —(CH2)3SO2—⟨phenyl with OC4H9 and tC8H17⟩ | H | Cl |
| [IV]-3-8 | (C4H9)2PO— | —H | —C18H37 | Cl |
| [IV]-3-9 | CH3NH—⟨phenyl⟩—CO— | —CH3 | —(CH2)3—⟨phenyl⟩—NHCOCHO(C2H5)—⟨phenyl with tC5H11, tC5H11⟩ | Cl |

-continued

Formula [IV]:

$$\begin{array}{c} X \quad H \\ R_1 \diagdown \diagup N \diagdown \diagup R_5 \\ \| \quad \| \\ N - N \diagdown R_6 \end{array}$$

| Coupler No. | $R_1$ | $R_5$ | $R_6$ | X |
|---|---|---|---|---|
| [IV]-3-10 | $C_{11}H_{25}OCHCONH$—(2,3,5,6-tetrafluoro-4-oxyphenyl), with $C_2H_5$ branch | —$(CH_2)_3NHCOCH_3$ | 2-$OC_4H_9$-5-$tC_8H_{17}$-phenyl with —$(CH_2)_3SO_2$— | Br |
| [IV]-3-11 | $CH_3SO_2CH_2$— | —H | 4-methylphenyl-NHCOCHO-(2-Cl-phenyl), with $C_{12}H_{25}$ | H |
| 5-38 | —$CF_3$ | 4-methylphenyl-NHCOCHO-(2-Cl-phenyl), with $C_{12}H_{25}$ | —$CF_3$ | H |
| 5-39 | —$OCOCH_2Cl$ | —$C_3H_7(i)$ | —$SO_2C_{18}H_{37}$ | Br |
| 5-40 | —$OSO_2CH_3$ | 2-$OC_4H_9$-5-$C_8H_{17}(t)$-phenyl with —$SO_2$— | —$CF_3$ | Cl |
| [IV]-7-1 | —$CF_3$ | H | CN | H |

-continued

Formula [IV]:

$$\begin{array}{c} X \\ R_1 \end{array} \diagdown N \diagup \overset{H}{N} \diagdown \begin{array}{c} R_5 \\ R_6 \end{array}$$

| Coupler No. | $R_1$ | $R_5$ | $R_6$ | X |
|---|---|---|---|---|
| [IV]-7-2 | —COO.CH$_3$ | —CH$_2$—C$_6$H$_4$—NHCOC$_{18}$H$_{37}$ (m) | CN | H |
| [IV]-7-3 | —CN(C$_2$H$_5$)$_2$ with C=O | —CH$_2$—C$_6$H$_4$—NHCOC$_{18}$H$_{37}$ (m) | CN | H |
| [IV]-7-4 | —CCH$_3$ with C=O | —CH$_2$—C$_6$H$_4$—NHCOC$_{18}$H$_{37}$ (m) | CN | H |
| [IV]-7-5 | —COOH | —CH$_2$—C$_6$H$_4$—NHCOC$_{18}$H$_{37}$ (m) | CN | H |
| [IV]-7-6 | —SO$_2$—C$_6$H$_5$ | H | —SO$_2$—C$_6$H$_4$—NHCOC$_{12}$H$_{25}$ (m) | H |
| [IV]-7-7 | —OCOCH$_2$Cl | —OC$_3$H$_7$ | —SO$_2$C$_{18}$H$_{37}$ | Br |

-continued

Formula [IV]

| Coupler No. | R$_1$ | R$_5$ | R$_6$ | X |
|---|---|---|---|---|
| [IV]-7-8 | -OSO$_2$-C$_6$H$_5$ | -SO-C$_6$H$_3$(OC$_4$H$_9$)(tC$_8$H$_{17}$) | -CF$_3$ | Cl |
| [IV]-7-9 | CF$_3$ | -OSO$_2$CF$_3$ | -SO$_2$N(C$_{10}$H$_{21}$)$_2$ | Cl |
| [IV]-7-10 | -NHCOCF$_3$ | -PO(OC$_8$H$_{17}$)$_2$ | -C(CH$_3$)$_2$(CH$_2$)$_2$NHCO(CH$_2$)$_2$O-C$_6$H$_4$-C$_{15}$H$_{31}$ | Cl |

| Coupler No. | $R_1$ | $R_7$ | $R_8$ | X | Formula [V] |
|---|---|---|---|---|---|
| [V]-1-1 | CN— | —H | ![]: 4-(NHCOCHO-C12H25)-phenyl-CH2-C6H4-tC4H9 | H | |
| [V]-1-2 | CH3— | —COCH3 | —C15H37 | Cl (pyrazolyl) | |
| [V]-1-3 | CF3— | —H | 4-(NHSO2-(4-OC12H25-phenyl))-phenyl-CH3 | H | |
| [V]-1-4 | CH3OCO— (O=) | —H | —(CH2)3NHCOCH2O-(4-OC14H29-phenyl)—C15H37 | H | |
| [V]-1-5 | C8H17OCO— (O=) | —CH3 | 4-(NHCOCHO-C12H25)-phenyl-SO2-(2-Cl, 4-OH)-phenyl, with 3-Cl, NHCO-(m-tolyl) | H | |
| 2-68 | —SO2—C6H5 | —CH3 | | H | |
| 2-69 | —OSO2—(2-Cl-phenyl) | H | 2,4-di(C5H11(t))-phenyl-NHCOCHO-(CH2)2O-, C2H5 | Cl | |

-continued

Formula [V]

[Structure: pyrazolotriazole-type coupler skeleton with substituents $R_1$, $R_7$, $R_8$, X, and NH group on the fused ring system]

| Coupler No. | $R_1$ | $R_7$ | $R_8$ | X |
|---|---|---|---|---|
| 2-70 | —OCO(CF$_2$)$_6$H | H | —(CH$_2$)$_2$O—C$_6$H$_4$—C$_{15}$H$_{31}$ (meta) | Cl |
| 2-71 | C$_6$H$_5$—SO$_2$— | H | —(CH$_2$)$_3$—C$_6$H$_4$—NHCOCH(C$_2$H$_5$)—C$_6$H$_3$(C$_5$H$_{11}$(t))(C$_5$H$_{11}$(t)) | Cl |
| 2-72 | —SO$_2$N(C$_2$H$_5$)$_2$ | H | —C$_6$H$_4$—NHCOCH(C$_{12}$H$_{25}$)—C$_6$H$_4$—C$_4$H$_9$(t) | Cl |
| 2-73 | —OCO(CF$_2$)$_5$H | H | —(CH$_2$)$_3$—C$_6$H$_4$—NHSO$_2$—C$_6$H$_4$—OC$_{13}$H$_{25}$ | Cl |
| [V]-3-1 | C$_4$H$_9$SO$_2$NH—C$_6$H$_4$—CH$_2$SO$_2$— | —H | —C$_6$H$_4$—NHCOCH(C$_4$H$_9$)O—C$_6$H$_3$(tC$_5$H$_{11}$)(tC$_5$H$_{11}$) | Cl |

-continued
Formula [V]

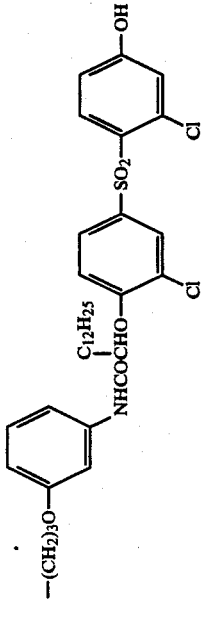

| Coupler No. | $R_1$ | $R_7$ | $R_8$ | X |
|---|---|---|---|---|
| [V]-3-2 | CF$_3$SO$_2$O— | —CH$_3$ | (3-O(CH$_2$)$_3$-phenyl)-NHCOCHO(C$_{12}$H$_{25}$)-2-Cl-4-SO$_2$-(3-Cl-4-OH-phenyl) | H |
| [V]-3-3 | (C$_6$H$_5$)$_2$NSO$_2$— | H | | phthalimido |
| [V]-3-4 | 2,5-dimethylpyrrol-1-yl | H | (4-CH$_3$-phenyl)-NHCOCHO(C$_2$H$_5$)-(3-C$_{15}$H$_{31}$-phenyl) | Cl |
| [V]-3-5 | Cl— | H | (4-CH$_3$-phenyl)-NHCOCHO(C$_{12}$H$_{25}$)-(4-tC$_4$H$_9$-phenyl) | H |
| [V]-3-6 | HOOC— | H | —C$_{18}$H$_{37}$ | Cl |
| [V]-3-7 | tC$_4$H$_9$SO$_2$— | —CH$_3$ | —(CH$_2$)$_3$SO$_2$C$_{18}$H$_{37}$ | Br |
| 5-41 | —CN | —SO$_2$C$_{18}$H$_{37}$ | —(CH$_2$)$_3$SO$_2$-(4-OC$_{12}$H$_{25}$-phenyl) H | Cl |

-continued

Formula [V]

| Coupler No. | R₁ | R₇ | R₈ | X |
|---|---|---|---|---|
| 5-42 | ‒NHSO₂‒(C₆H₅) | ‒SO₂N(C₁₆H₃₃)₂ | H | Cl |
| 5-43 | ‒(C₆H₄)‒SO₂‒C₁₂H₂₅ | ‒NHCOCF₃ | H | H |
| [V]-7-1 | ‒(C₆H₅)‒SO₂‒ | H | 3-SO₂-C₆H₄-NHCOCH(C₁₂H₂₅)O-C₆H₅ | H |
| [V]-7-2 | ‒(C₆H₄)‒SO₂‒C₁₂H₂₅ | H | ‒SO₂N(C₁₀H₂₁)₂ | H |
| [V]-7-3 | ‒CN | H | 2-OC₄H₉-4-(iC₆H₁₇)-C₆H₃-SO₂‒ | Cl |

-continued

Formula [V]

| Coupler No. | $R_1$ | $R_7$ | $R_8$ | X |
|---|---|---|---|---|
| [V]-7-4 | —SO—C$_{18}$H$_{37}$ | H | —SO— (phenyl)—NHCOC$_{12}$H$_{25}$ | —O—(phenyl) |
| [V]-7-5 | (pentafluorophenyl)—SO$_2$— | —OSO$_2$CF$_3$ | CF$_3$ | Cl |
| [V]-7-6 | —CF$_3$ | CN | —SO$_2$—(2-OC$_4$H$_9$, 4-tC$_8$H$_{17}$-phenyl) | Cl |

Formula [VI]
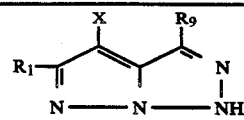
| Coupler No. | $R_1$ | $R_9$ | X |
|---|---|---|---|
| [VI]-1-1 | 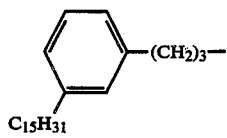 | —CN | Cl |
| [VI]-1-2 | $H_{35}C_{17}$— | —COCH$_3$ | 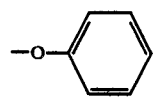 |
| [VI]-1-3 | CF$_3$— | —(CH$_2$)$_3$—O—C$_{12}$H$_{25}$ | H |
| [VI]-1-4 | 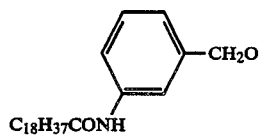 | —H | H |
| 2-64 | 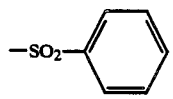 | 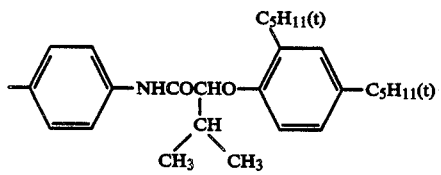 | H |
| 2-65 | 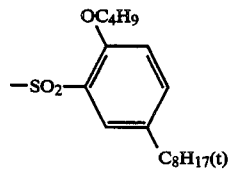 | —CH$_3$ | Cl |
| 2-66 | 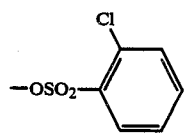 | 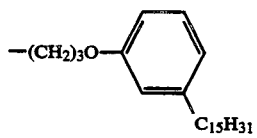 | Cl |
| 2-67 | —OCO(CF$_2$)$_3$H | 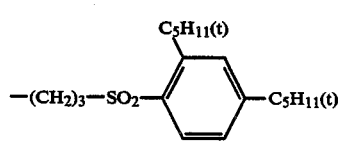 | Cl |
| [VI]-3-1 | 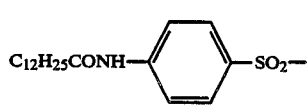 | —H | Cl |
| [VI]-3-2 | C$_{18}$H$_{37}$SO— | 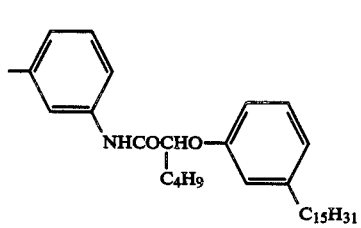 | H |

Formula [VI]

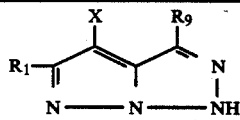

| Coupler No. | $R_1$ | $R_9$ | X |
|---|---|---|---|
| [VI]-3-3 | $(C_{12}H_{25})_2NSO_2-$ | $-CH_3$ | H |
| [VI]-3-4 | $(CH_3)_2CHCO-$ | $-(CH_2)_3O-\text{C}_6H_4-C_{15}H_{31}$ | $-O-C_6H_4-CH_3$ |
| 5-44 | $-SO_2CF_3$ | $-SO_2C_{18}H_{37}$ | Cl |
| 5-45 | $-SO_2C_{18}H_{37}$ | $-CN$ | Cl |
| 5-46 | $-CF_3$ | $-OCOC_{15}H_{23}$ | H |
| [VI]-7-1 | $-SO_2-C_6H_5$ | $-SO_2-C_6H_4-NHCOCH(C_{12}H_{25})O-C_6H_4-Cl$ | H |
| [VI]-7-2 | $-SO_2CF_3$ | $-SO_2N(C_{10}H_{21})_2$ | Cl |
| [VI]-7-3 | $-CF_3$ | $-OCOC_{11}H_{23}$ | H |
| [VI]-7-4 | $-SO_2C_{18}H_{37}$ | $-CN$ | H |
| [VI]-7-5 | $-CN$ | $-SO_2-C_6H_3(Cl)-NHCOC_{12}H_{25}$ | Cl |

The above-mentioned cyan couplers of the invention may readily be synthesized by anybody who is skilled in the art, with reference to, for example, Journal of the Chemical Society, Perkin I, 1977, pp. 2047-2052; J. Heterocycl. Chem., 11, p.423, 1974; Chem. Ber., 32, p.797, 1899 and 95, p.2861 and p.2881, 1962; U.S. Pat. Nos. 3,705,896 and 3,725,067; Japanese Patent Publication Open to Public Inspection (hereinafter called Japanese Patent O.P.I. Publication) Nos. 99437-1984, 42045-1983, 162548-1984, 171956-1984, 3552-1985, 42659-1985, 172982-1985, 190779-1985, 197688-1985 and 65247-1986; Japanese Patent Publication Nos. 43947-1971 and 43977-1971; Japanese Patent Application Nos. 120054-1986 and 122450-1986; and so forth.

Typical examples of synthesizing cyan couplers will be given below.

SYNTHESIS EXAMPLE 2-1

A sample will be represented by the following formulas.

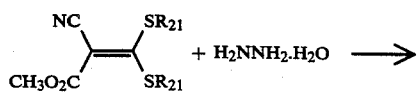

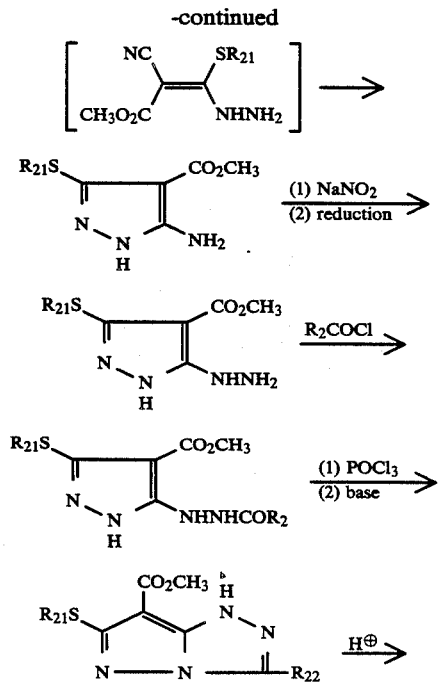

-continued
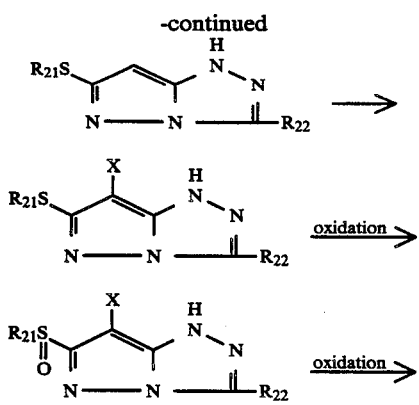
-continued
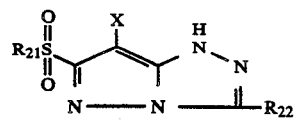
In the above-given reaction formulas, $R_{21}$, $R_{22}$ and X are synonymous with those given in Formula [I].
X can be introduced in the method described in Japanese Patent Publication No. 43947-1971.
Synthesis Example 3-1 (Synthesis of Cyan coupler II-3-1)
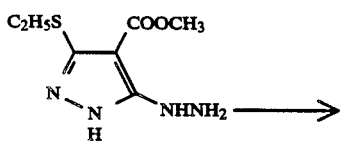
3-1-a
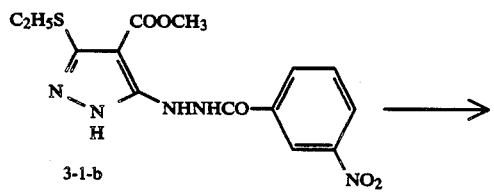
3-1-b
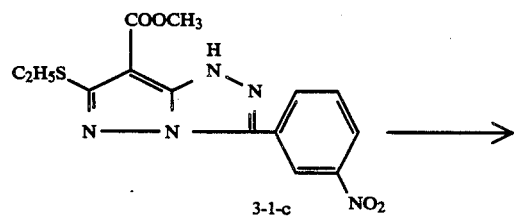
3-1-c
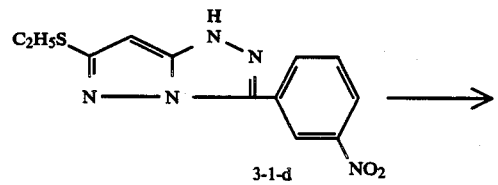
3-1-d
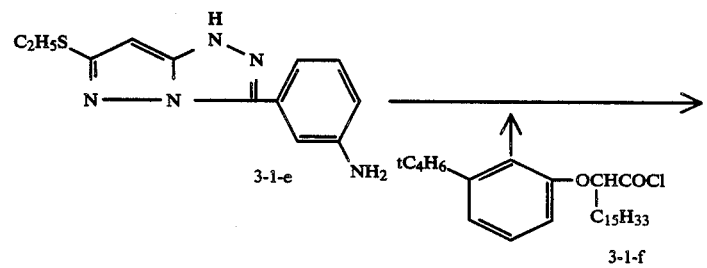
3-1-e  3-1-f

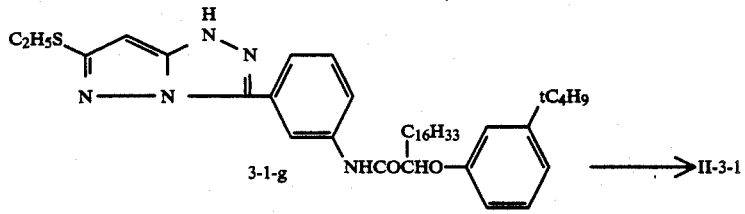

3-1-a was synthesized in the method described in Japanese Patent Application No. 120054-1986.

[3-1-a→3-1-b]

3-1-a of 0.01 mole was dissolved in 50 ml of acetonitrile and 0.012 moles of m-nitrobenzoyl chloride were then added thereto. An amount of 0.1 mole of triethylamine was dropped into the resulted solution. After stirring for 3 hours at room temperature, the resulted crystals were filtrated. Thus, 0.0072 moles of 3-1-b were obtained.

[3-1-b→3-1-c]

3-1-b of 0.0072 moles and 0.0095 moles of phosphorus oxychloride were added to 70 ml of toluene and the resulted solution was heatedly refluxed for 3.5 hours. After the toluene was distilled off, 0.1 mole of pyridine and 50 ml of acetonitrile were added and further the resulted solution was heatedly refluxed for 2.5 hours. After filtrating while it was still warm, 0.0041 moles of 3-1-c were obtained.

[3-1-c→3-1-d]

3-1-c of 0.0041 moles was added to a solvent mixed with 25 ml of acetic acid, 7 ml of sulfuric acid and 0.8 ml of water and the resulted solution was heatedly refluxed for 1.5 hours.

The resulted matter was neutralized with an aqueous sodium hydroxide solution and after extracted and condensed, water was added. Thus, deposited 3-1-d of 0.0030 moles were filtrated.

[3-1-d→3-1-e→3-1-g]

3-1-d of 0.0030 moles were dissolved in 50 ml of THF and the resulted solution was hydrogenated by making use of Pd/c. After Pd/c was filtrated and the solvent was then distilled off. The resulting deposited matter 3-1-d was dissolved in 100 ml of acetonitrile and 0.0052 moles of 3-1-f were added and, further, 0.004 moles of triethyleamine were dropped into the resulting solution. After stirring for 2 hours at room temperature, the deposited crystals were filtrated and recrystallized with ethyl acetate, so that 0.0024 moles of 3-1-g were obtained.

[3-1-g→II-3-1]

3-1-g of 0.0024 moles were dissolved in 15 ml of acetic acid and were then dropped gradually by 5 ml of an aqueous 35% hydrogen peroxide solution. After stirring for 2.5 hours at 55° C., 50 ml of water were added and the resulting solution was neutralized gradually with an aqueous sodium hydroxide solution and was then extracted and distilled with ethyl acetate. The deposited matter thus obtained thereby was recrystallized with acetonitrile. Thus, 0.0019 moles of the white needle crystals II-3-1 were obtained.

SYNTHESIS EXAMPLE 3-2 (Synthesis of II-3-18)

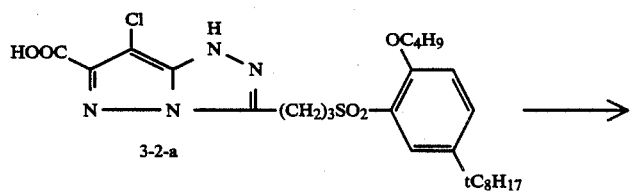

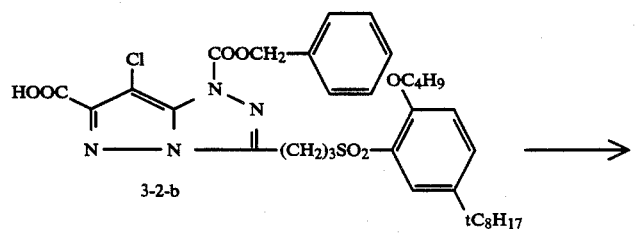

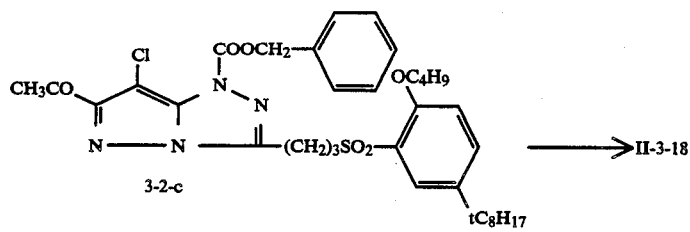

3-carboxy-4-chloro-5-aminopyrazole was used as the raw material and 3-2-a was synthesized in an ordinary method via a hydrorazine substance through a reaction with an acid chloride.

[3-2-a→3-2-b]

While 3-2-a of 0.01 mole and 5 ml of an aqueous 2N-sodium hydroxide solution were kept cooled with ice and stirred in 20 ml of acetonitrile, 0.01 mole of benzyloxy carbonyl chloride and 3 ml of an aqueous 4-sodium hydroxide solution were gradually dropped thereinto and the resulted solution was stirred for 30 minutes. After neutralizing with chloric acid, the neutralized matter was cooled and the precipitates were filtrated and washed by cooled water. Thus, 0.008 moles of 3-2-b were obtained.

[3-2-b→3-2-c]

Twenty (20) ml of a benzene solution containing 0.008 moles of 3-2-b were added with stirring into 22 ml of an diethyl ether solution containing 1N-methyl lithium and the resulted solution was stirred for 20 hours. After adding 100 ml of water with cooling, an extraction was made by making use of ethyl acetate and the solvents were then distilled off. The deposited matter was recrystallized with acetonitrile, so that 0.0040 moles of 3-2-c were obtained.

[3-2-c→II-3-18]

3-2-c of 0.0040 moles were dissolved in 60 ml of THF and a reduction was made with Pd/c.

After Pd/c was removed and the solvents wee distilled off, the resulted matter was recrystallized with ethyl acetate, so that 0.0030 moles of light-yellowish needle crystals of II-3-18 were obtained.

Synthesis Example 3-3 (Synthesis of III-3-1)

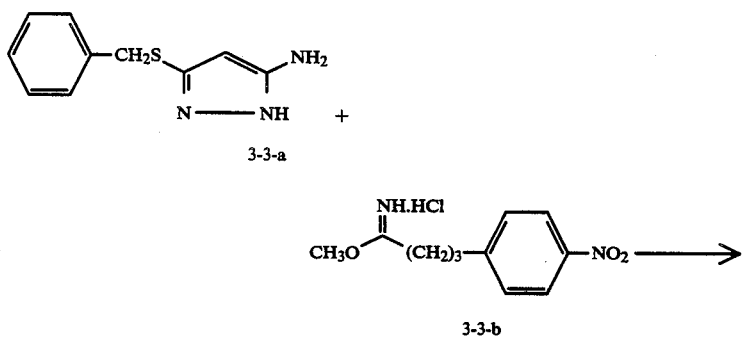

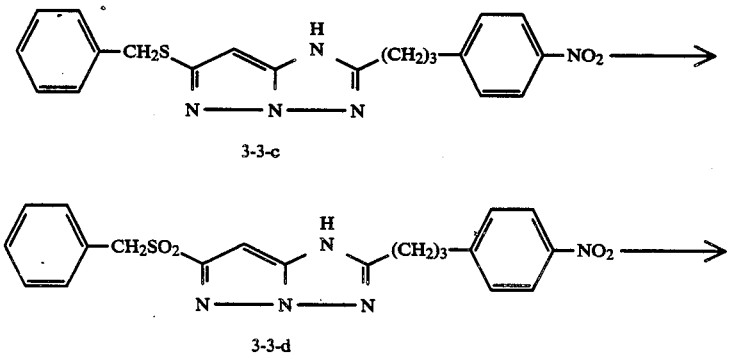

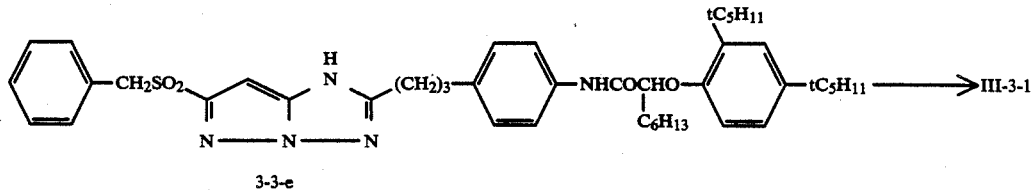

3-3-e

[Synthesis of 3-3-c]

3-3-a was synthesized in an ordinary mathod with reference to Japanese Patent Application No. 120054-1986.

In 20 ml of toluene, 0.01 mole of 3-3-a and 0.011 moles of 3-3-b were heatedly refluxed for 20 hours and the toluene was then distilled off. The residues were dissolved in 20 ml of methanol and a methanol solution containing hydroxylamine was added at 0° C. The resulted solution was stirred for 1.5 hours at room temperature and was then poured into 200 ml of water. After then, the deposited matter was filtrated and was then dissolved in 60 ml of THF. The resulted solution was added with 0.004 moles of triethylamine and stirred. While stirring, a THF solution containing 0.7 g of p-toluenesulfonic acid chloride was added and further stirred. After then, the insoluble matters were filtrated and the filtrate was heatedly refluxed for 7 hours in nitrogen atmosphere so that THF was distilled off. The residues were put into a small amount of 50 ml of methanol, so that 0.0045 moles of 3-3-c were obtained.

[3-3-c→3-3-d]

3-3-c of 0.0045 moles were oxidized in the same manner as in [3-1-g→II-3-1] of Synthesis Example 3-1, so that 0.0039 moles of 3-3-d were obtained.

[3-3-d→3-3-e]

3-3-d of 0.0039 moles were hydrogenated and reduced in the same manner as in [3-1-d→3-1-e→3-1-g] of Synthesis Example 3-1 and were further reacted with an appropriate acid chloride, so that 0.0031 moles of the coarse crystals of 3-3-e were obtained.

[3-3-e→III-3-1]

3-3-e of 0.0031 moles were dissolved in 50 ml of chloroform and 0.0050 moles of N-chlorosuccinimide were added thereto.
The resulted solution was stirred for 30 minutes at room temperature and the solvents were distilled off. The recrystallization was made with a mixed solvent of ethyl acetate and n-hexane, so that 0.0022 moles of white powdered crystals of III-3-1 were obtained.

Synthesis Example 3-4 (Synthesis of III-3-16)

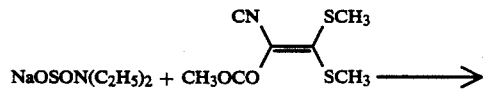

3-4-a

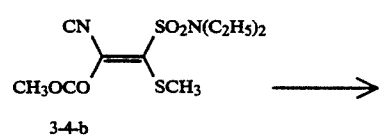

3-4-b

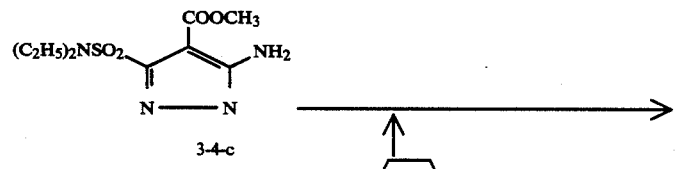

3-4-c

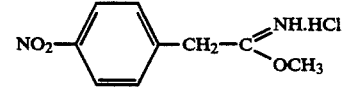

3-4-d

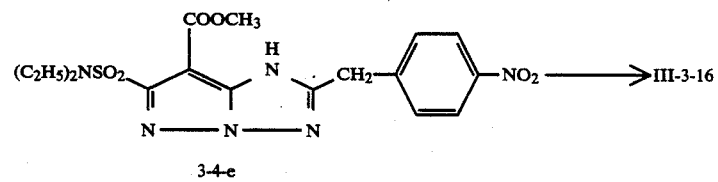

3-4-e

[3-4-a→3-4-b]

3-4-a of 0.01 mole and 0.022 moles of sodium diethylamino sulfinate were dissolved in 50 ml of methanol and the resulted solution was heatedly refluxed for 3 hours. The solvents were distilled off and the insoluble matters were filtrated after adding acetic acid to the residues and the filtrates were condensed, so that 0.0061 moles of 3-4-b were obtained.

[3-4-b→3-4-c]

3-4-b of 0.0061 moles were added to 100 ml of ethanol and 0.0080 moles of 100% hydrazine hydrate were dropped thereinto. After heatedly refluxing for 7 hours, the solvents were distilled off and the residues were recrystallized out of the ethanol, so that 0.0031 moles of 3-4-c were obtained.

[3-4-c→3-4-e]

3-4-c of 0.0031 moles were reacted with 3-4-d and were then the ring thereof was closed in the same manner as in [Synthsesis of 3-3-c] of Synthesis Example 3-3, so that 0.0014 moles of 3-4-e were obtained.

[3-4-e→III-3-16]

3-4-e of 0.0041 moles were applied to a hydrogenation-reduction and were then reacted with an acid chloride in the same manner as in [3-1-d→3-1-e→3-1-g] of Synthesis Example 3-1. The resulted coarse crystals of III-3-16 were recrystallized with acetonitrile, so that 0.0010 mole of III-3-16 was obtained.

Synthesis Example 3-5 (Synthesis of IV-3-1)

[Synthesis of 3-5-c]

3-5-a of 0.010 mole and 3-5-b of 0.010 mole were heatedly refluxed for 17 hours in 50 ml of anhydrous ethanol and the solvents were distilled off. After then, the resulted matter was distilled under reduced pressure, so that 0.0060 moles of 3-5-c were obtained.

[Synthesis of 3-5-d]

3-5-c of 0.0060 moles were heatedly refluxed for 6.5 hours in 70 ml of ethanol and 30 ml of a 25% sulfuric acid solution. after cooling, 0.05 moles of sodium carbonate was added and stirred. The resulted insoluble matters were filtrated and the solvents were distilled off. The resulted residues were recrystallized with acetonitrile, so that 0.0040 moles of 3-5-d were obtained.

[3-5-d→3-5-e]

3-5-d of 0.0040 moles were applied to a hydrogenation-reduction in the same manner as in [3-1-d→3-1-e→3-1-g] of Synthesis Example 3-1 and were further reacted with an acid chloride, so that 0.0032 moles of 3-5-e were synthesized. A mixed solvent of ethyl acetate and hexane was used as the recrystallizing solvent.

[3-5-e→III-3-1]

A peracetic acid oxidation was carried out by making use of 0.0032 moles of 3-5-e in the same amnner as in [3-1-g→II-3-1] of Synthesis Example 3-1. White needle crystals of IV-3-1 of 0.0020 moles were obtained through the recrystallization thereof with acetonitrile.

Synthesis Example 4-1

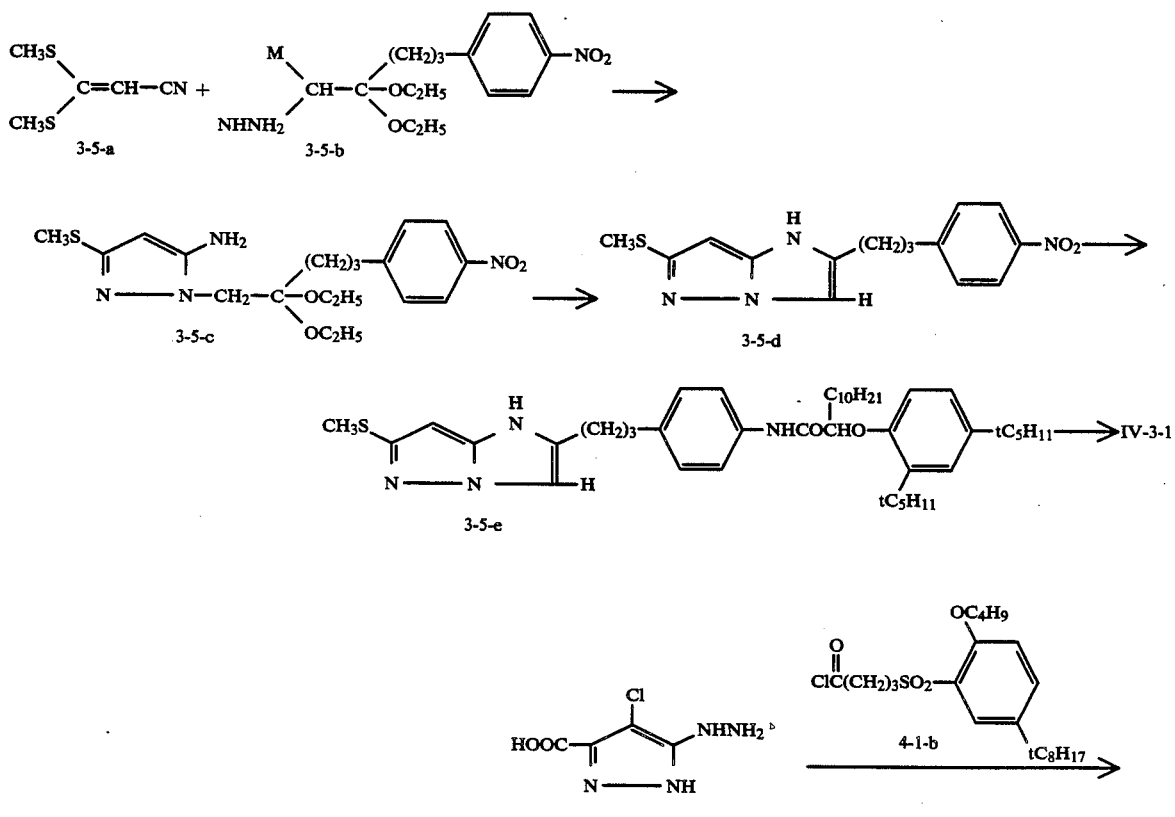

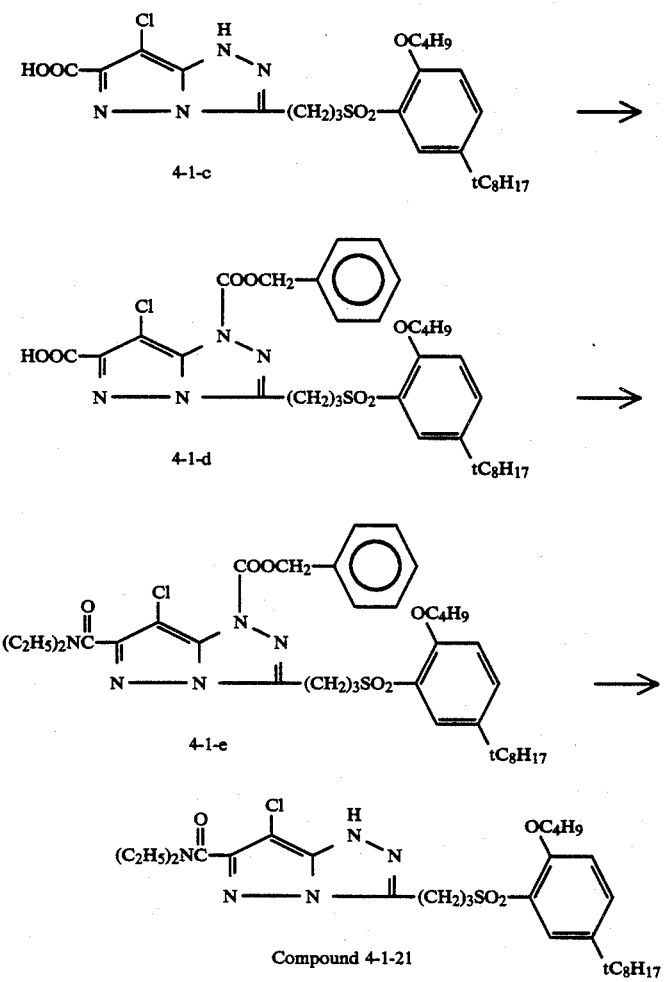

[Synthesis of 4-1-a]

3-carboxy-4-chloro-5-aminopyrazole of 0.25 moles were added to 1.5 liters of 6N-chloric acid and after the resulted solution was completely dissolved once, it was cooled down to 5° C. or lower and thereto 60 ml of an aqueous solution containing 19 g of sodium nitrite were added at a temperature of from 5° to 10° C. The resulted solution was stirred for 30 minuted at 0° C.

Next, 120 g of stannous chloride dihydrate were dissolved in 500 ml of a conc. chloric acid solution. The resulted solution was gradually dropped into the aforegoing solution at a temperature of 0° C. or lower. The resulted matter was stirred for one hour as it was and further stirred for another 2.5 hours at room temperature.

The solution was made to be 4 liters by adding water and was then introduced with hydrogen-sulfide gas for one hour. The deposited solids were filtrated and the filtrates were concentrated. Then, 400 ml of ethanol were added to the concentration and the deposited white crystals were filtrated. The filtrates were dossolved in water and neutralized in an aqueous sodium hydrogencarbonate solution, so that 0.15 moles of 4-1-a were obtained.

[4-1-a→4-1-c]

4-1-a of 0.15 moles were dissolved in 750 ml of acetonitrile and 0.18 moles of 4-1-b were added. Thereto, 210 ml of triethylamine were dropped. The resulted solution was stirred for 3 hours at room temperature, the deposited crystals were filtrated. The crystals and 0.15 moles of phosphorus oxychloride were added to one liter of toluene and the resulted solution was heatedly refluxed for 4 hours. Then, the toluene was distilled off and 750 ml of acetonitrile and 120 ml of pyridine were added. The resulted matter was further heatedly refluxed for 3.5 hours and was then filtrated when it was still warm, so that 0.062 moles of 4-1-c were obtained.

[4-1-c→4-1-d]

While cooling with ice and stirring in 120 ml of acetonitrile, 4-1-c of 0.062 moles and 31 ml of an aqueous 2N-sodium hydroxide solution were dropped gradually into 20 ml of an aqueous 4N-sodium hydroxide solution containing 0.062 moles of benzyloxycarbonyl chloride. The resulted solution was stirred for 30 minutes and neutralized with chloric acid. After then, it was cooled down and the precipitates were filtrated and washed with cooled water, so that 0.050 moles of 4-1-d were obtained.

[4-1-d→4-1-e]

4-1-d of 0.050 moles and 7 ml of triethylamine were dissolved in 100 ml of dichlormethane and thereinto 24

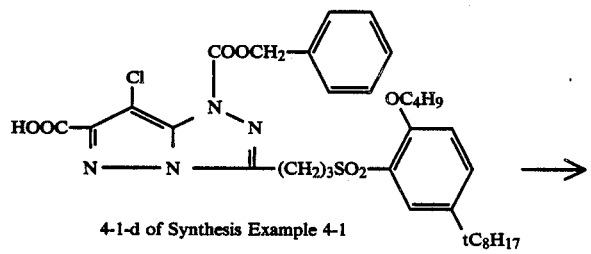

4-1-d of Synthesis Example 4-1 ml of a dichlormethane solution containing 6 ml of thionyl chloride were dropped. The resulted solution was stirred for one hour at room temperature and was further stirred by adding ice water. Therefrom, an organic layer was separated and the solvents were distilled off. After then, the obtained residues were dissolved in 100 ml of acetonitrile. The resulted solution was added with 7 ml of pyridine and 0.06 moles of diethylamine and was then stirred for one hour. After further stirring for 2 hours at 55° C., the solution was poured into 300 ml of water and the deposited matters were filtrated and recrystallized with ethyl acetate, so that 0.022 moles of 4-1-e were obtained.

[4-1-e→Compound 4-1-21]

4-1-e of 0.022 moles were dissolved in 300 ml of THF and the resulted solution was reduced with pd/c. The pd/c was removed therefrom and the solvents were distilled off. After then, the resulted matter was recrystallized with ethyl acetate, so that 0.014 moles of Compound 4-1-21 in the form of white needle crystals were obtained.

Synthesis Example 4-2

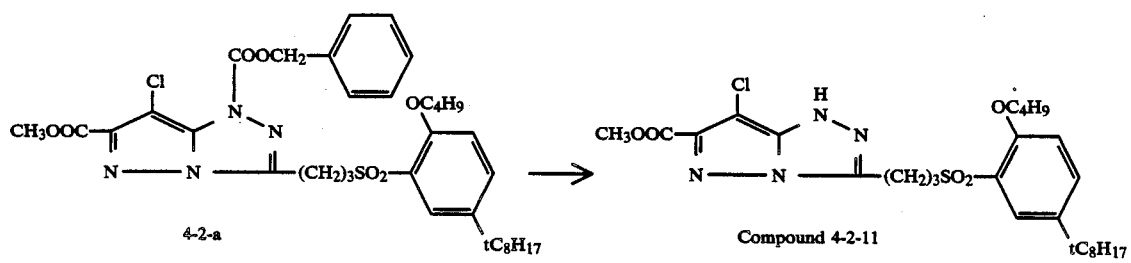

[Synthesis of 4-2-a]

4-1-d of Synthesis Example 4-1 was used as the raw material. A mixture of 0.025 moles of 4-1-d of Synthesis Examples 4-1, 3.05 ml of methanol and 50 ml of dichloroethane was added with 0.125 ml of sulfuric acid and the solution was refluxed for 7 hours. After cooled, 100 ml of water was added and an extraction was made with ethyl acetate. The extracted matter was washed with an aqueous sodium hydrogencarbonate solution and the solvents were dilstilled off. After then, the residues were recrystallized with acetonitrile, so that 0.015 moles of 4-2-a were obtained.

[4-2-a→Compound 4-2-11]

4-2-a of 0.015 moles were dissolved in 200 ml of methanol and the solution resulted was reduced with pd/c. After removing the pd/c, the solvents were distilled off. The resulted matter was recrystallized with ethyl acetate, so that 0.008 moles of Compound 4-2-11 in the form of white powder were obtained. Synthesis Example 6-1 Synthesis of compound 6-1-1)

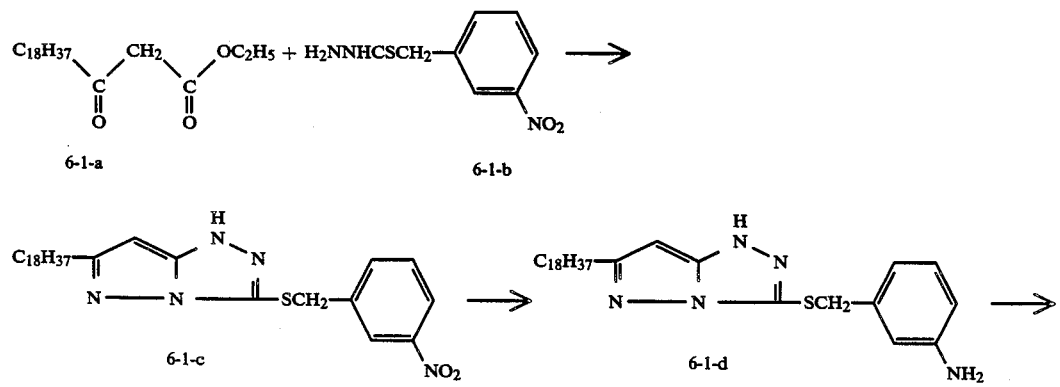

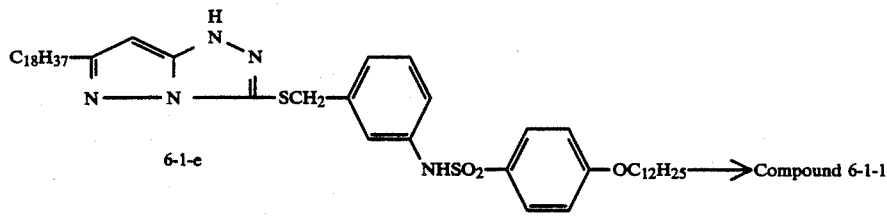

[Synthesis of 6-1-c]

6-1-a of 0.012 moles and 0.01 mole of 6-1-b, i.e., a hydroiodide, were heated in 30 ml of amyl alcohol for 30 minutes. After cooled, the deposited matters were filtrated and was then washed with ether, so that 0.0061 moles of 6-1-c were obtained.

[6-1-c→6-1-e]

6-1-c of 0.0061 moles was dissolved in 100 ml of THF and the resulted solution was hydrogenated by making use of Pd/C. After Pd/C was filtrated, the solvents were distilled off. Thus, the course crystals, 6-1-d, were obtained. 6-1-d thus obtained was dissolved in 200 ml of acetonitrile and added with 0.0092 moles of p-dodecaoxyphenylsulfonyl chloride. Triethylamine of 0.0081 moles were dropped into the resulted solution and stirred for 2 hours at room temperature. After then, the deposited crystals were filtrated and was recrystallized with ethyl acetate, so that 0.0042 moles of 6-1-e were obtained.

[6-1-e→Compound 6-1-1]

6-1-e of 0.0042 moles were dissolved in 30 ml of acetic acid and, thereto 10 ml of a 35% hydrogen peroxide solution were gradually dropped and stirred for 3 hours at 50° C. After then, 100 ml of water were added and gradually neutralized with an aqueous sodium hydroxide solution and an extraction was made with ethyl acetate. The deposited matters obtained by distillating the solvents off were recrystallized with acetonitrile, so that 0.0030 moles of Compaound 6-1-1 in the form of white needle crystals were obtained.

Synthesis Example 6-2 (Synthesis of compound 6-2-13)

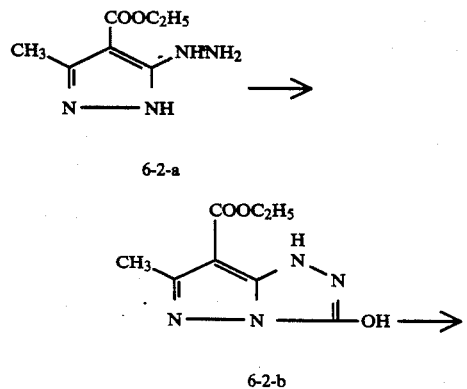

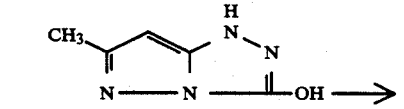

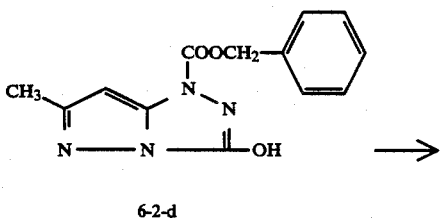

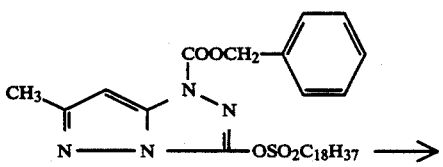

Compound 6-2-13

6-2-a was synthesized in an ordinary method.

[6-2-a→6-2-b→6-2-c]

6-2-a of 0.010 mole was dissolved in 50 ml of acetonitrile and added with 0.015 moles of urea. Then, the resulted solution was stirred for 2 hours and the deposited matters, 6-2-b, were filtrated. The filtrated deposited matters were heatedly refluxed for one hour in a mixed solvent of 30 ml of 6-2-b, 18 ml of acetic acid, 0.7 ml of sulfuric acid and water and were then neutralized with an aqueous sodium hydroxide solution. An extraction was made with ethyl acetate and the solvents were distilled off, so that 0.0049 moles of 6-2-c were obtained.

[6-2-c→6-2-d]

6-2-c of 0.0049 moles and 3 ml of an aqueous 2N-sodium hydroxide solution were added into 15 ml of acetonitrile. While cooling with ice and stirring the resulted solution, 0.0049 moles of benzyloxycarbonyl chloride and 1.5 ml of an aqueous 4N-sodium hyroxide solution were gradually dropped thereinto and then stirred for 30 minutes. The solution was neutralized with chloric acid and was then cooled. The precipitates were filtrated and washed with cooled water, so that 0.0034 moles of 6-2-d were obtained.

[6-2-d→6-2-e]

6-2-d of 0.0034 moles were dissolved in 30 ml of acetonitrile and thereinto 0.0040 moles of 6-2-d were dropped and 3 ml of pyridine were added. Then, the resulted solution was stirred at room temperature. The resulted reaction solution was poured into water and the deposited matters were filtrated and the filtrates were recrystallized with a mixed solvents of ethyl acetate and hexane, so that 0.0020 moles of 6-2-e were obtained.

[6-2-e→Compound 6-2-13]

6-2-e of 0.0020 moles were dissolved in 30 ml of THF and the solution was reduced with Pd/C. The Pd/C was removed and the solvents were distilled off. The resulted matter was recrystallized with ethyl acetate, so that 0.0015 moles of Compound 6-2-13 in the form of light-yellow powdered crystals were obtained.

Synthesis Example 7-1(Synthesis of II-7-1)

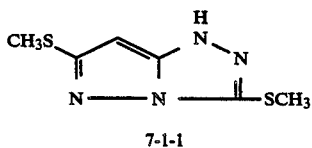

7-1-1

[Synthesizing Process 7-1-1]

o-ethyl-S-methyldiethyl malonate of 0.012 moles and S-methylisothiocarbohydrazide hydroiodide of 0.01 mole were heated in 25 ml of amyl alcohol for 30 minutes.

After cooling it, the deposited matters were filtrated and the filtrates were washed with ether, so that 0.006 moles of coarse crystals 7-1-1 were obtained.

[Synthesizing Process 7-1-2]

The above-obtained 7-1-1 of 0.006 moles were dissolved in 15 ml of acetic acid. Then, 5 ml of an aqueous 35% hydrogen peroxide solution were dropped gradually into the resulted solution and stirred for 2 hours. After then, 50 ml of water were added and neutralized with an aqueous sodium hydroxide solution. The resulted pH 6.5 reaction solution was extracted with ethyl acetate and the solvents were distilled off. The resulted deposited matters were washed with acetonitrile, so that 0.005 moles of white needle crystals II-7-1.

Synthesis Example 7-2 (Synthesis of II-7-2)

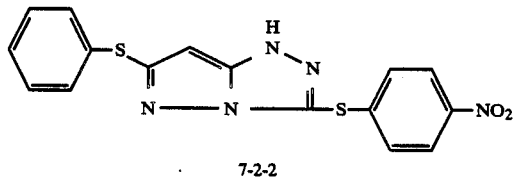

7-2-2

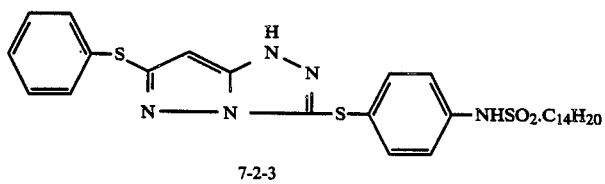

7-2-3

(Synthesizing Process 7-2-1)

o-ethyl-S-methyldiethyl malonate of 0.012 moles and S-(p-nitrophenyl)isothiocarbohydrazide hydroiodide of 0.01 mole were heated in 25 ml of amyl alcohol for one hour.

After cooling it, the deposited matters were filtrated and the filtrates were washed with ether and dried up, so that 0.0059 moles of 7-2-2 were obtained.

(Synthesizing Process 7-2-2)

The above-obtained 7-2-2 of 0.0059 moles were dissolved in 50 ml of THF hydrogenated by making use of pd/c. After the pd/c was filtrated, the reaction solution was distilled off and the deposited matters resulted were dissolved in 100 ml of acetonitrile. Then, 0.01 mole of tetradecanedulfonyl chloride was added and 0.012 moles of triethylamine were dropped. After stirring for 2 hours at room temperature, the deposited crystals were filtrated and further recrystallized with ethyl acetate, so that 0.0055 moles of Compound 7-2-3 were obtained.

Synthesizing Process 7-2-3

The above-obtained 7-2-3 were oxidized in the same manner as in Synthesizing Process 7-1-2 of Synthesis Example 7-1, so that 0.0039 moles of white needle crystals II-7-2 were obtained.

Synthesis Example 7-3 (Synthesis of II-7-3)

Synthesizing Process 7-3-1

According to the method described in Japanese Patent Application No. 120054-1986, 7-3-4 were obtained.

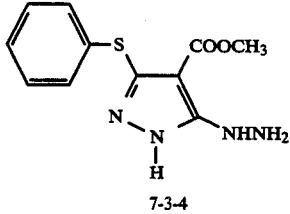

7-3-4

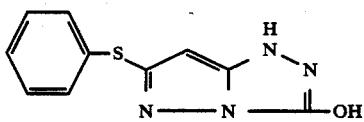

7-3-5

The above-obtained 7-3-4 of 0.02 moles were dissolved in 100 ml of acetonitrile and 0.030 moles of urea were added. The resulted solution was then stirred for 2 hours and the deposited matters were filtrated. The filtrates were heated and refluxed for one hour in a mixed solvent of 50 ml of acetic acid, 20 ml of sulfuric acid and 1.0 ml of water. The resulted matter was then neutralized with an aqueous sodium hydroxide solution and extracted with ethyl acetate, and the solvents were distilled off, so that 0.0128 moles of 7-3-5 were obtained.

Synthesizing Process 7-3-2

The above-obtained 7-3-5 of 0.0062 moles were dissolved in 60 ml of acetonitrile and 0.0070 moles of tetradecanecarbonyl chloride were dropped. After a small amount of pyridine was added, the resulted solution was stirred at room temperature. The resulted reaction solution was poured into water and the deposited matters were filtrated, so that 7-3-6 was obtained. Further, 0.0035 moles of II-7-3 were obtained in the same manner as in Synthesizing Process 7-1-2 of Synthesis Example 7-1.

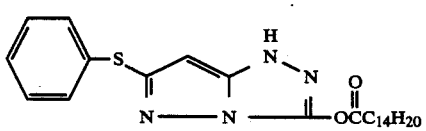

7-3-6

Synthesis Example 7-4 (Synthesis of II-7-4)

Compound 7-3-5 of Synthesis Example 7-3 was used.

The above-mentioned 7-3-5 of 0.006 moles were dissolved in 60 ml of acetonitrile and 0.0065 moles of m-nitrophenylsulfonyl chloride were dropped. After a small amount of pyridine was added, the resulted solution was stirred at room temperature. The resulted reaction solution was poured into water and the deposited matters were filtrated. The filtrates were further hydrogenated and reduced in the same manner as in Synthesizing Process 7-2-2 of Synthesis Example 7-2 and reacted with tetradecanecarbonyl chloride. The reacted manner was oxidized in the same manner as in Synthesizing Process 7-1-2 of Synthesis Example 7-1, so that 0.0028 moles of II-7-4 were obtained.

Synthesis Example 7-5 (Synthesis of II-7-6)

According to the methods described in J. Heterocycl. Chem., Vol. 11, p.423, 1974, Japanese Patent Application No. 120054-1986 and so forth, 7-5-7 was synthesized.

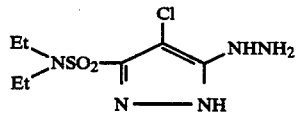

7-5-7

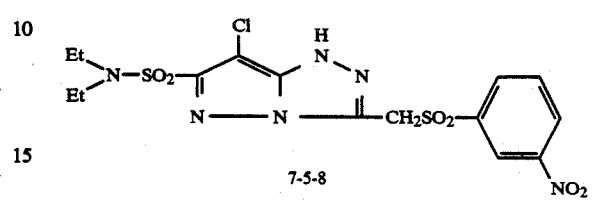

7-5-8

The above-mentioned 7-5-7 of 0.01 mole and 0.015 moles of m-nitrophenylsulfonylbenzoyl chloride were added to 50 ml of ethyl acetate and 1.0 g of triethylamine was dropped. After stirring for 2 hours, the deposited crystals were filtrated and washed. The resulted crystals and 0.01 mole of phosphorus oxychloride were heatedly refluxed for 2 hours in 30 ml of toluene and the solvents were distilled off. After 10 g of pyridine and 30 ml of acetonitrile were added and further heatedly refluxed for 2 hours, the deposited matters were recrystallized with acetonitrile, so that 0.0050 moles of 7-5-8 were obtained. Successively, a reaction was carried out in the same manner as in Synthesizing Process 7-2-2 of Synthesis Example 7-2, so that the objective matter of 0.0031 moles were obtained.

Synthesis Example 7-6 (Synthesis of III-7-1)

Synthesizing Process 7-6-1

According to an ordinary method, the following aminopyrazoles were synthesized, so that 7-6-9, 7-6-10 and 7-6-11 were obtained, respectively.

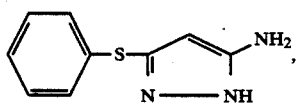

7-6-9

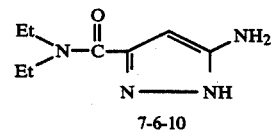

7-6-10

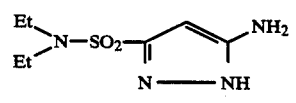

7-7-11

According to the method described in Japanese Patent O.P.I. Publication No. 65247-1986, the following 7-6-12 and 7-6-13 were synthesized with the corresponding nitrile compounds, respectively.

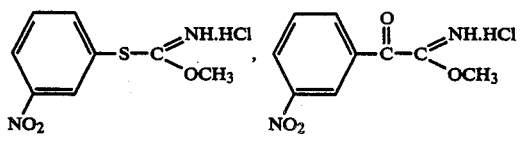

7-6-12, 7-6-13

Synthesizing Process 7-6-2

The above-mentioned 7-6-9 of 0.01 mole and 0.011 moles of 7-6-12 were heatedly reflexed for 20 hours in 20 ml of toluene and the solvents were then distilled off. The resulted residues were dissolved in 20 ml of methanol and a methanol solution containing hydroxylamine was added at 0° C. The resulted solution was stirred for one hour at room temperature. The obtained solution was poured into 200 ml of water, and the desposited matters were filtrated.

The filtrates were dissolved in 50 cc of THF and 0.004 moles of triethylamine were added and stirred. While stirring, a THF solution containing 0.7 g of p-toluenesulfonic chloride was added. After further stirring, the resulted insoluble matters were filtrated and the filtrate was heatedly reflexed for 7 hours in the nitrogen atmosphere. After then, THF was distilled off and the residues were dissolved in a small amount of methanol. When the resulted solution was poured into 50 ml of water, 0.0014 moles of 7-6-14 were obtained.

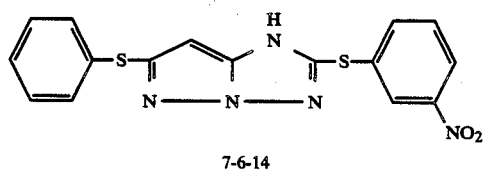

7-6-14

The above-obtained 7-6-14 of 0.0014 moles were hydrogenated and reduced in the same manner as in Synthesizing Process 7-2-2 of Synthesis Example 7-2 and were then reacted with an acid chloride. The resulted matter was further oxidized in the same manner as in Synthesizing Process 7-2-3 of Synthesis Example 7-2, so that 0.0026 moles of III-7-1 were obtained.

Synthesis Example 7-7 (Syntheses of III-7-2, -6 and -7)

According to the method of Synthesizing Process 7-6-2 of Synthesis Example 7-6, III-7-2 was synthesized by making use of 7-6-9 and 7-6-13 each synthesized in Synthesizing Process 7-6-1 of Synthesis Example 7-6, III-7-6 by 7-6-10 and 7-6-12 and III-7-7 by 7-6-11 and 7-6-13; and Their yields were 29%, 47% and 30%, respectively.

Synthesis Example 7-8 (Synthesis of IV-7-1)

According to J. Heterocycl. Chem. 10, p.411, 1973 and Japanese Patent O.P.I. Publication No. 162548-1984, 7-8-15 and 7-8-16 were synthesized.

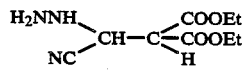

7-8-15

-continued

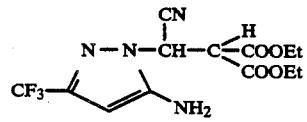

7-8-16

The above-given 7-8-15 of 0.01 mole and 0.012 moles of 7-8-16 were heatedly refluxed for 10 hours in anhydrous ethanol and the solvents were removed. After then, a distillation was applied under reduced pressure, so that 0.0072 moles of 7-8-17 were obtained.

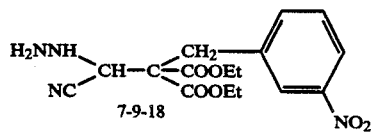

7-8-17

The resulted 7-8-17 of 0.0072 moles were heatedly refluxed for 3 hours in 300 ml of ethanol and 80 ml of a 20% sulfuric acid solution. After cooling, excessively solidified sodium carbonate was added and filtrated, and the solvents were removed. The residues were recrystallized with acetonitrile, so that 0.0040 moles of IV-7-1 were obtained.

Synthesis Example 7-9 (Synthesis of IV-7-5)

7-9-18 and 7-9-19 were synthesized in the same manner as in Synthesis Example 7-8.

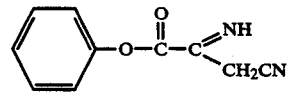

7-9-18

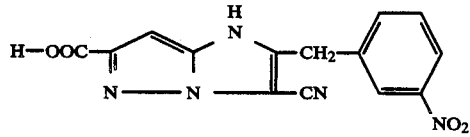

7-9-19

In the same manner as in Synthesis Example 7-8, 0.031 moles of 7-9-20 were obtained by making reaction with 0.06 moles of 7-9-19.

In the same manner as in Synthesizing Process 7-2-2 of Synthesis Example 7-2, 7-9-20 was hydrogenated and reduced, and was then reacted in ethyl acetate in the presence of pyridine with an acid chloride of 1.2 times more than the moles of 7-9-20 to produce coarse crystals. The coarse crystals were recrystallized with acetonitrile, so that 0.025 moles of IV-7-5 were obtained.

Synthesis Example 7-10 (Synthesis of IV-7-2)

A mixture of 0.01 mole of 7-9-20, 0.03 moles of methanol and 20 ml of dichloroethane were added with 0.05 moles of sulfuric acid and refluxed for 8 hours. After cooling, 50 ml of water were added and the resulted solution was extracted with ethyl acetate. The ethyl acetate solution was washed with an aqueous sodium hydrocarbonate and the solvents were removed. After then, the residues were recrystallized with acetonitrile. Further, a hydrogenation and reduction were made in the same manner as in Synthesizing Process 7-2-2 of Synthesis Example 2-2 and the reaction was made with an acid chloride, so that 0.0065 moles of IV-7-2 were obtained.

The couplers of the invention are ordinarily used in an amount within the range of from $1 \times 10^{-3}$ moles to 1 mole and more preferably from $1 \times 10^{-2}$ moles to $8 \times 10^{-1}$ moles per mole of silver halide used.

The couplers of the invention may be applied similarly with the methods and techniques applied to ordinary cyan dye forming couplers. It is typical to prepare a color light-sensitive material of the invention in such a manner that the cyan couplers of the invention are compounded into a silver halide emulsion and the resulting emulsion is coated over to a support.

When the aforementioned red light-sensitive silver halide emulsion containing a coupler of the invention represented by one of the aforegiven Formulas [I-1] through [I-7] is added with at least one kind of spectral sensitizing dyes selected from the group consisting of those represented by the following Formulas [A], [B], [C], [D], [E] and [F], the excellent effects can be displayed on both photosensitivity of emulsion layer and aging stability of coating liquid.

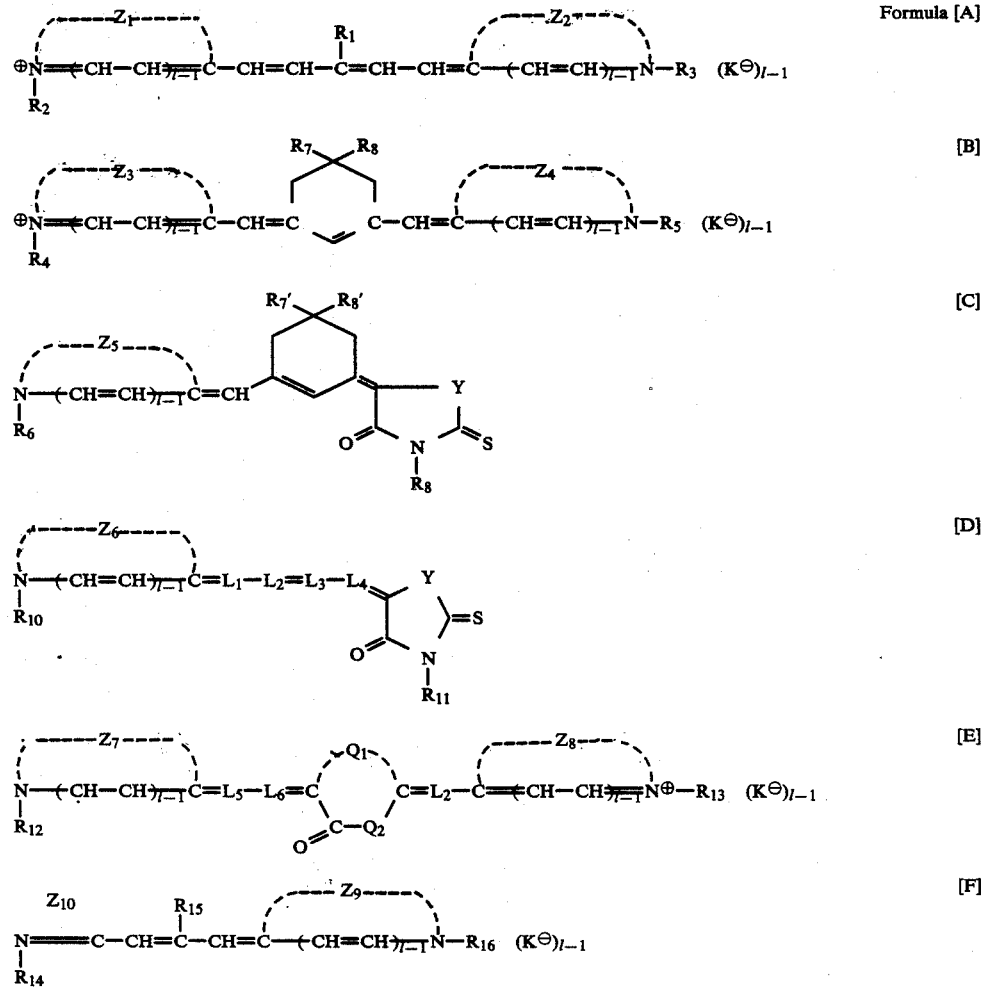

Wherein $Z_1$ through $Z_9$ each represent a group of atoms necessary for completing a benzene ring or a naphthalene ring condensed with a pyridine ring, an imidazole ring, a thiazole ring, a selenazole ring, an oxazole ring or a tetrazole ring; $Z_{10}$ represents a group of atoms necessary for completing a benzothiazole ring, a benzoselenazole ring, a β-naphthothiazole ring, a β-naphthoselenazole ring, a benzimidazole ring or a 2-quinoline ring; $Q_1$ and $Q_2$ each represent a group of atoms necessary for associatively completing a nucleus of 4-thiazolidinone, 5-thiazolidinone or 4-imidazolidinone; $R_1$ and $R_{15}$ each represent a hydrogen atom, an alkyl group or an aryl group; $R_7$, $R_8$, $R'_7$ and $R'_8$ each represent an alkyl group; $R_9$ and $R_{11}$ each represent an alkyl group, an aryl group or a heterocyclic group; $R_2$, $R_3$, $R_4$, $R_5$, $R_6$, $R_{10}$, $R_{12}$, $R_{13}$, $R_{14}$ and $R_{16}$ each represent an alkyl group or an aryl group;

l is an integer of 1 or 2; Y represents a sulfur atom or selenium atom; $L_1$ through $L_6$ each represent a substituted or nonsubstituted methine group; and K represents an acid anion.

The spectral sensitizing dyes, which are represented by the aboeve-given Formulas [A], [B], [C], [D], [E] and [F] respectively and may preferably be used in the invention, are well-known ones. They may readily be synthesized in such a method as described in, for example, F. M. Hamer, 'The Chemistry of Heterocyclic Compounds', Vol. 18; and A. Weissberger, 'The Cyanine Dyes and Related Compounds', Edited by Interscience, New York, 1964.

The typical examples of the above-mentioned spectral sensitizing dyes which may preferably be used in the invention will be given below.

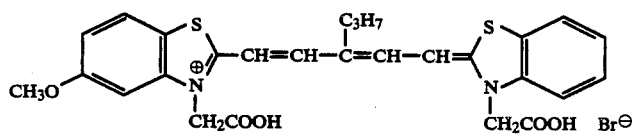
[S-1]

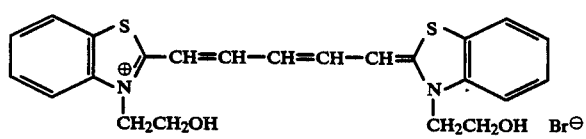
[S-2]

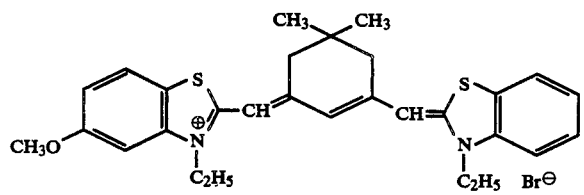
[S-3]

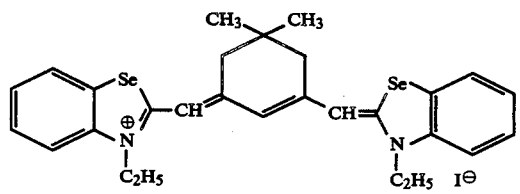
[S-4]

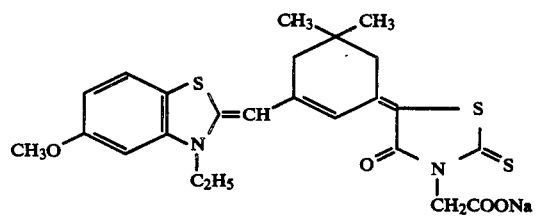
[S-5]

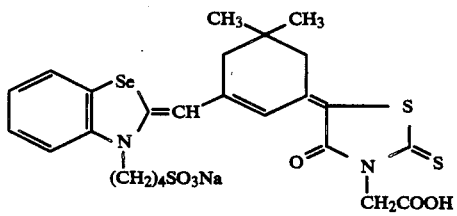
[S-6]

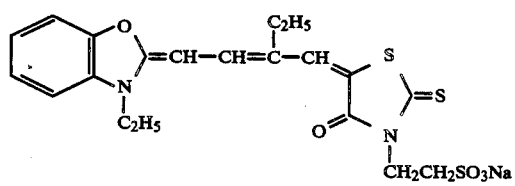
[S-7]

-continued

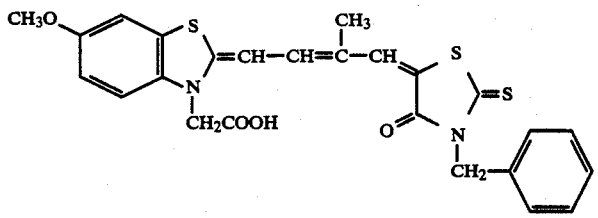 [S-8]

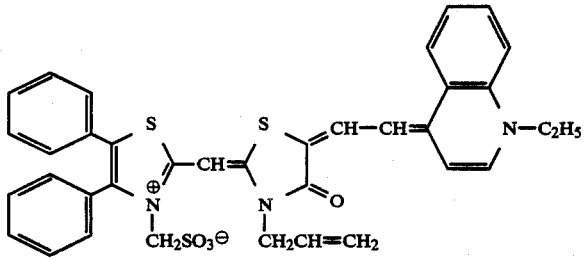 [S-9]

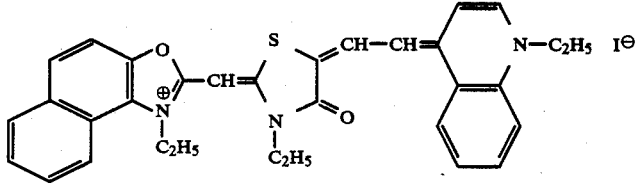 [S-10]

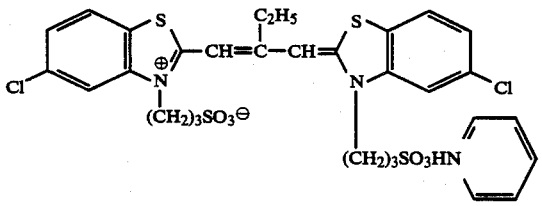 [S-11]

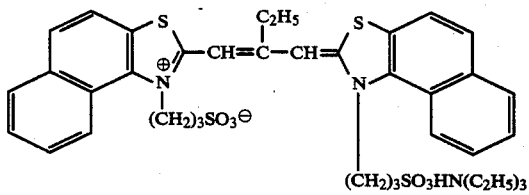 [S-12]

The above-mentioned spectral sensitizing dyes may be added into an emulsion in any method well-known in the art. For example, these spectral sensitizing dyes may be dispersed directly into an emulsion; or, they are dissolved in such a water-soluble solvent as pyridine, methyl alcohol, ethyl alcohol, methyl cellosolve, acetone or the mixture thereof, they are diluted with water, or they are dissolved in water, so that they may be added in the form of a solution into the emulsion. It is also allowed to use a supersonic wave oscillation in the course of the dissolution.

It is also allowed to use a method in which a spectral sensitizing dye is dissolved in a volatile organic solvent and the resulting solution is dispersed in a hydrophilic colloid and the resulting dispersion is added into an emulsion, as described in U.S. Pat. No. 3,469,987 and so forth; and another method in which a water-insoluble dye is dispersed in a water-soluble solvent without dissolving the dye and the resulting dispersion is added into an emulsion, as described in Japanese Patent Publication No. 24185-1971. In addition to the above, a spectral sensitizing dyes may be added in the form of a dispersion prepared in an acid dissolution-dispersion method, into an emulsion. Besides the above, the addition of a spectral sensitizing dye into an emulsion may be made in each of the methods described in U.S. Pat. Nos. 2,912,345, 3,342,605, 2,996,287 and 3,425,835; and so forth.

A point of time when adding the spectral sensitizing dyes of the invention into an emulsion may be any point of time in the course of preparing the emulsion. It is, however, preferable to add such a dye during or after a chemical sensitization. It is also allowed to add the dyes in parts during or after the chemical sensitization.

The spectral sensitizing dyes represented by Formulas [A] through [F] may be used together with other spectral sensitizing dyes in combination, in the form of the so-called supersensitizing combination. In this case, the respective spectral sensitizing dyes are dissolved in solvents which are the same with or the different from each other, respectively, and the resulting solutions are mixed together before adding the solutions into an emulsion and the mixed solution is then added into the emulsion, or each of the solutions may be added separately into the emulsion. When adding the solutions separately, the order and intervals of the addition may be determined according to the purposes.

An amount of the spectral sensitizing dyes used in the invention is within the range of from $1.20 \times 10^{-4}$ to $0.15 \times 10^{-4}$ moles, preferably from $1.0 \times 10^{-4}$ to $0.3 \times 10^{-4}$ moles and more preferably from $0.8 \times 10^{-4}$ to $0.4 \times 10^{-4}$ moles per mole of a silver halide used.

The color light-sensitive materials of the invention are available in the form of, for example, a color negative or positive film, a color print paper and so forth.

The light-sensitive materials, including the above-mentioned color print paper, may be those for either monochromatic or multicolor use. In the multicolor light-sensitive materials, the cyan couplers of the invention are contained in a red light-sensitive silver halide emulsion layer thereof. The multicolor light-sensitive materials each have dye image forming constitution units which are sensitive to the three primary color spectral regions, respectively. Each constitution unit may be made of a single-layered or multi-layered emulsion layer sensitive to a certain spectral region. The component layers of a light-sensitive material, including an image forming constitution unit layer, may be arranged in various order as known in the art.

The typical multicolor light-sensitive materials are comprised of a support carrying thereon a cyan dye image forming constitution unit, (in which at least one of cyan couplers is a cyan coupler of the invention), comprising at least one red light-sensitive silver halide emulsion layer containing at least one cyan coupler; a magenta dye image forming constitution unit comprising at least one green light-sensitive silver halide emulsion layer containing at least one magenta coupler; and a yellow dye image forming constitution unit comprising at least one blue light-sensitive silver halide emulsion layer containing at least one yellow coupler. The light-sensitive materials may be provided with supplementary layers such as a filter layer, an interlayer, a protective layer, a subbing layer and so forth.

To contain the cyan couplers of the invention into an emulsion, it will do to follow a conventionally known method. For example, a silver halide emulsion applicable to the invention may be prepared in the following manner. Namely, the cyan couplers of the invention are dissolved independently or in combination into a single solution of either a high boiling solvent such as tricresyl phosphate, dibutyl phthalate and so forth each having a boiling point of not lower than 175° C. or a low boiling solvent such as butyl acetate, butyl propionate and so forth, or the mixed solution thereof if required and, then, the resulting solution is mixed in an aqueous gelatin solution containing a surface active agent. Next, the mixed solution is homogenized by a high-speed rotary mixer or a colloid-mill and a silver halide is then added to the resulting emulsion.

The compositions of silver halides preferably used in the invention include that of silver chloride, silver chlorobromide or silver chloroiodobromide. Further, the mixture such as that of silver chlorobromide and silver bromide and so forth may also be used. Namely, when a silver halide emulsion relating to the invention is used in a color print paper, a high-speed developability in particular is demanded. It is, therefore, preferred that chlorine atom is added into the halogen composition of a silver halide and it is particularly preferred that silver chloride, silver chlorobromide or silver chloroiodobromide has at least 1% silver chloride content.

Silver halide emulsions may be chemically sensitized in an ordinary method and may also be optically sensitized to a desired spectral wavelength region.

With the purposes of preventing fog and/or keeping photographic characteristics stable in the course of manufacturing, storing or processing light-sensitive materials in photographic industry, it is allowed to add a compound well known as an antifogging agent or a stabilizer.

Color light-sensitive materials of the invention may be applied with an anti-color-foggant, a dye-image stabilizer, a UV absorbent, an antistatic agent, a matting agent, a surface active agent, and so forth, each of which are ordinarily used in light-sensitive materials.

The above-mentioned additives may be referred to Research Disclosure, Vol. 176, pp. 22–31, December, 1978, for example.

An image may be formed by processing a color light-sensitive material of the invention in a color development process which is well-known in the art.

Color light-sensitive materials relating to the invention may be treated in an alkaline active bath, if the hydrophilic colloidal layer of the sensitive material contains a color developing agent to serve as a color developing agent by itself or in the form of the precursor of the developing agent.

After color development, color light-sensitive materials of the invention may be bleached and fixed, provided that both of the bleaching and the fixing steps may be carried out at the same time.

After fixing step, a washing step is ordinarily carried out, but the washing step may be either substituted by a stabilizing step or carried out with the stabilizing step in combination.

EXAMPLES

Next, with reference to the following examples, the invention will be described in detail. It is, however, to be understood that the invention shall not be limited thereto.

EXAMPLE 1—1

Sample 1—1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 1.35 g of dioctyl phthalate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 1-2 through No. 1-13 each of the invention were prepared in quite the same manner as in Example 1—1, except that the comparative coupler a was replaced by the couplers indicated in Table 1—1 (provided that the amounts added were the same molar amounts as in the comparative coupler a).

The resulted Samples No. 1-1 through No. 1-13 were exosed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediaminetetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to thus processed Samples No. 1-1 through No. 1-13, the measurements were made respectively each of the maximum spectral absorption wavelengths ($\lambda$max), the reflection densities of 420 nm (D$\lambda$420) when the reflection densities of $\lambda$max were 1.0, and the half band widths (W$\frac{1}{2}$) which are the difference between one point on the longer wavelength side that each $\lambda$max and the shorter wavelength side that each $\lambda$max when the reflection densities of $\lambda$max were 0.5. After then, the spectral absorption characteristics and the color reproducibility of each Sample were examined.

The smaller a value of D$\lambda$420 is, the less an irregular absorption in green region is. The smaller a value of W$\frac{1}{2}$ is, the sharper an absorption is. The facts mean that a color reproducibility is excellent.

FIG. 1—1 shows the absorption spectra of Sample Nos. 1—1, 1-2 and 1-6. Wherein, 1 represents Comparative Coupler a (of Sample 1—1), 2 and 6 represent Coupler II-1—1 (of Sample 1-2) and Coupler II-1—1 (of Sample 1-6) each of the invention, respectively.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 1—1, wherein the heat and moisture resisting properties of the dye-images are indicated by the percentage of the residual dyes which still remained after the heat and moisture resistance tests were tried, to the initial density of 1.0.

For those measurements, a densitometer, Model KD-7R (manufactured by Konishiroku Photo Ind. Co., Ltd.), was used.

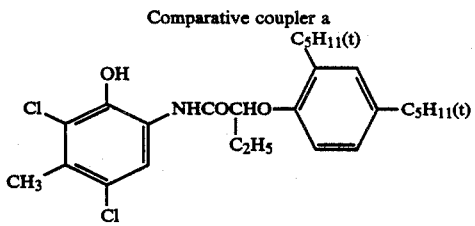

Comparative coupler a

TABLE 1-1

| Sample No. | Coupler used | λ max (nm) | W½ | Dλ 420 | Residual dye (%) |
|---|---|---|---|---|---|
| 1-1 | Comp. a | 650 | 208 | 0.46 | 60 |
| 1-2 | Inv. II-1-1 | 610 | 113 | 0.29 | 96 |
| 1-3 | Inv. II-1-4 | 612 | 119 | 0.32 | 97 |
| 1-4 | Inv. II-1-5 | 606 | 124 | 0.27 | 94 |
| 1-5 | Inv. II-1-11 | 595 | 121 | 0.24 | 96 |
| 1-6 | Inv. III-1-1 | 615 | 112 | 0.30 | 97 |
| 1-7 | Inv. III-1-2 | 597 | 126 | 0.24 | 95 |
| 1-8 | Inv. III-1-3 | 608 | 113 | 0.27 | 96 |
| 1-9 | Inv. III-1-4 | 602 | 120 | 0.26 | 97 |
| 1-10 | Inv. IV-1-2 | 604 | 146 | 0.25 | 91 |
| 1-11 | Inv. IV-1-6 | 595 | 153 | 0.24 | 89 |
| 1-12 | Inv. V-1-1 | 597 | 167 | 0.24 | 89 |
| 1-13 | Inv.-VI-1-2 | 591 | 181 | 0.22 | 92 |

As is obvious from Table 1—1, it is found that every sample having the couplers of the invention has excellent spectral absorption characteristics, because their half band widths are extremely narrower than those of the sample having the comparative coupler and the irregular absorptions are relatively less, as compared with the sample used the comparative coupler. It is further found that every sample having the couplers of the invention is relatively solid, because of the high percentage of residual dyes and the relatively excellent moisture resisting property.

In addition, FIG. 1—1 shows the fact that the couplers of the invention are relatively less in undesirable irregular absorption caused in green region and relatively sharp in absorption in the regions around $\lambda$max, as compared with the conventional phenol type couplers.

EXAMPLE 1-2

Samples No. 1-14 through No. 1-19 of red-sensitive color reversal photographic light-sensitive materials were prepared by coating the following layers over to a triacetyl cellulose film support, in order from the support side.

The amounts of the compounds added are expressed by the amounts thereof per sq. meter unless otherwise specially stated. (Amounts of silver halides are expressed in terms of the contents of silver.)

Layer 1: An emulsion layer

A red-sensitive emulsion layer comprising 1.4 g of gelatin, 0.5 g of red-sensitive silver chlorobromide emulsion (containing silver chloride of 96 mol%) and the couplers shown in Table 1-2 dissolved in 1.50 g of dibutyl phthalate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

| (Reversal processing steps) | | |
|---|---|---|
| Step | Time | Temperature |
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| (Primary developer) | |
|---|---|
| Water | 700 ml |
| Sodium tetrapolyphosphate | 2 g |
| Sodium sulfite | 20 g |
| Hyroquinone. monosulfonate | 30 g |
| Sodium carbonate, monohydrate | 30 g |
| 1-phenyl,4 methyl,4-hydroxymethyl-3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |
| hexasodium nitrilo,N,N,N—trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer C) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |
| Sodium hydroxide | 3 g |
| Citrazinic acid | 1.5 g |
| N,ethyl-N—(β-methanesulfonamidoethyl)-3,methyl-4-aminoaniline,sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |

| -continued | |
|---|---|
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediaminetetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt. %) | 5.0 ml |
| Water to be added to make | 1000 ml |

With each of the processed samples No. 1-14 through No. 1-19, the maximum spectral absorption wavelength ($\lambda$max), the half band width (W$\frac{1}{2}$) and D$\lambda$420 were measured in the same manner as in Example 1—1. The results thereof are shown in Table 1-2.

The measurements of transmission densities relating to the Example 1-2 were made with a densitometer, Model KD-7R.

TABLE 1-2

| Sample No. | Coupler used | $\lambda$ max (nm) | W$\frac{1}{2}$ | D$\lambda$ 420 | Residual dye (%) |
|---|---|---|---|---|---|
| 1-14 | Comp. a | 651 | 170 | 0.47 | 62 |
| 1-15 | Inv. II-1-7 | 599 | 101 | 0.24 | 96 |
| 1-16 | Inv. II-1-10 | 613 | 103 | 0.29 | 96 |
| 1-17 | Inv. III-1-7 | 616 | 95 | 0.31 | 95 |
| 1-18 | Inv. III-1-9 | 596 | 100 | 0.22 | 96 |
| 1-19 | Inv. IV-1-1 | 601 | 128 | 0.25 | 91 |

As is obvious from Table 1-2, it is found that every sample having the couplers of the invention has excellent spectral absorption characteristics and excellent color reproducibility, because their half band widths are extremely narrower and their D$\lambda$420 are also less than those of the sample having the comparative coupler.

It is also found that the Samples used the couplers of the invention are relatively solid, because the percentage of the residual dye-images was remarkably improved.

EXAMPLE 2-1

[Preparation of a red light-sensitive silver halide emulsion]

A silver chlorobromide emulsion containing silver chloride of 96 mol% was added with sodium thiosulfate in an amount of $1 \times 10^{-5}$ moles per mole of the silver chlorobromide emulsion and was then chemically sensitized. Five minutes before completely the chemical sensitization, the resulted chemically sensitized emulsion was added with the following spectral sensitizing dye a, which is to be used in red light-sensitive emulsion layers and was in the form of a 0.1% solution, in an amount of $5.0 \times 10^{-5}$ moles per mole of a silver halide used. Fiver minutes later, the resulted emulsion was added, at the point of time when the chemical sensitization was completed, with an aqueous 0.5% solution of 4-hydroxy-6-methyl-1,3,3a,7-tetrazaindene and, thereafter, with an aqueous 10% gelatin solution. The resulted mixture was stirred and cooled, so that a red light-sensitive silver halide emulsion was prepared.

(Preparation of light-sensitive material)

Sample 2-1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion and 0.45 g of comparative cyan coupler a dissolved in 0.24 g of dioctyl phthalate.

Layer 2: A protective layer

A protective layer containing 1.2 g of gelatin, whereto 2,4-dichloro-6-hydroxy-s-triazine sodium salt was added as a hardener in an amount of 0.017 g per g of the gelatin used.

Next, Samples No. 2—2 through No. 2-21 each of the invention were prepared in quite the same manner as in Example 2-1, except that the comparative coupler a and the spectral sensitizing dye a were replaced by the couplers of the invention shown in Table 2-1 and the spectral sensitizing dyes shown in Table 2-1, respectively. (The amounts of the couplers and spectral sensitizing dyes were in the amounts of the same moles as in Example 2-1.)

With respect to the above-mentioned Samples No. 2-1 through No. 2-21, for the purpose of checking up the aging stability of the coating liquids used, there prepared two kinds of each sample, i.e., one kind thereof was coated with the first emulsion layer coating liquid aged for one hour after the coating liquid had been prepared and another kind thereof was coated with the same coating liquid but aged for five hours after it had been prepared.

The resulted Samples No. 2-1 through No. 2-21 were exposed to light through a wedge and were then processed in the following processing steps.

| (Processing steps) | | |
| --- | --- | --- |
| Developing | 38° C. | 3 min. 30 sec. |
| Bleach-fixing | 38° C. | 1 min. 30 sec. |
| Stabilizing of washing | 25 to 30° C. | 3 min. |
| Drying | 75 to 80° C. | 2 min. |

The processing liquids use in each of the steps were as follows.

| (Color developer) | |
| --- | --- |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |

| -continued | |
| --- | --- |
| Water to be added to make | 1 liter |
| pH to be adjusted to | pH 10.20 |
| (Bleach-fixer) | |
| Ferric ammonium ethylenediaminetetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

Figures 1, 2:
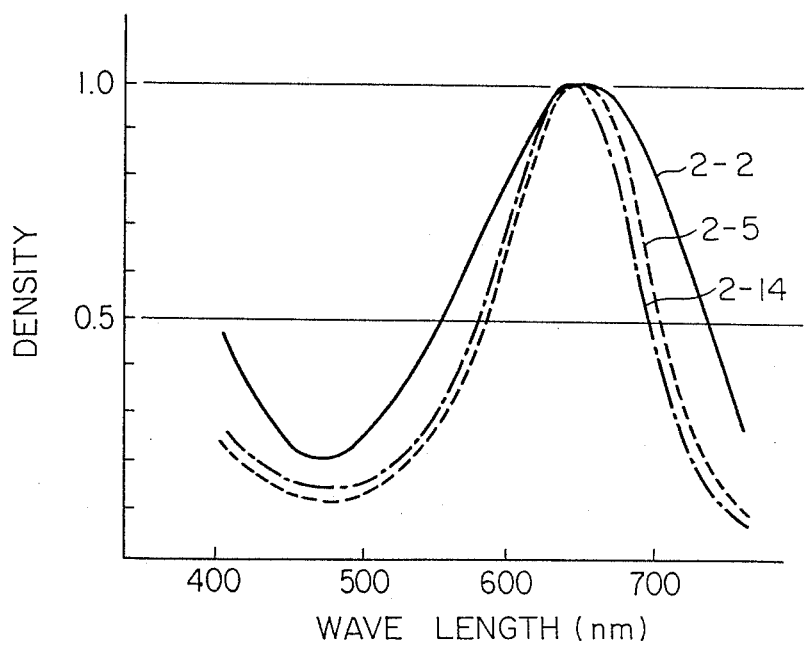

With respect to each sample thus processed and coated after aged for one hour, the measurements were made of the maximum spectral absorption wavelength (λmax), the reflection density of 420 nm when the reflection density of λmax was 1.0, and the half band width (i.e., the difference between the wavelength of the reflection density of 0.5 on the side of the wavelength longer than λmax and the wavelength of the reflection density of 0.5 on the side of the wavelength shorter than λmax). The smaller a value of Dλ420 is, the less an irregular absorption in red region is. The smaller a half band width is, the sharper an absorption is. The facts mean that a color reproducibility is excellent. FIG. 2-1 shows the absorption spectra of Sample Nos. 2-2, 2-5 and 2-14.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 2-1, wherein the heat and moisture resisting properties of the dye-images are indicated by the percentage of the residual dyes which still remained after the heat and moisture resistance tests were tried, to the initial density of 1.0.

With respect to the samples coated with the coating liquids respectively aged for one hour and for 5 hours, the densities thereof were measured with a densitometer to check up the sensitivities and fogs thereof. The standard optical density point for determining the sensitivities of the samples was set to be a point of fog plus 0.20.

For the relative sensitivity ratio, Sample No. 2-1 containing comparative coupler a and spectral sensitizing dye a, whose coating liquid was allowed to stand for one hour, was regarded as the criterion of 100%.

For those measurements, a densitometer, Model KD-7R (manufactured by Konishiroku Photo Ind. Co., Ltd.), was used.

The results thereof are correctively shown in Table 2-1.

Comparative coupler a

-continued

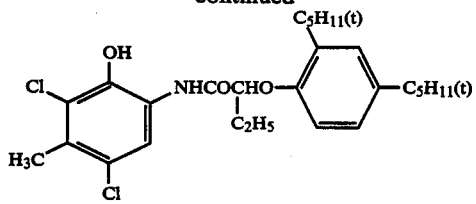

Spectral sensitizing dye a

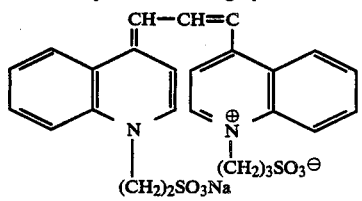

TABLE 2-1

| Sample No. | Coupler used | Spectr. sensi. dye | λ max (nm) | W½ | Dλ 420 | Residual dye (Heat-resist) % | Sensitivity 1-hr | Sensitivity 5-hrs |
| --- | --- | --- | --- | --- | --- | --- | --- | --- |
| 2-1 | Comp. a | a | 652 | 208 | 0.44 | 60 | 100 | 71 |
| 2-2 | Comp. a | S-3 | 652 | 202 | 0.42 | 62 | 115 | 104 |
| 2-3 | Inv. 2-(2) | a | 648 | 129 | 0.23 | 95 | 102 | 79 |
| 2-4 | Inv. 2-(2) | S-1 | 650 | 120 | 0.20 | 98 | 126 | 121 |
| 2-5 | Inv. 2-(2) | S-3 | 649 | 120 | 0.19 | 99 | 131 | 129 |
| 2-6 | Inv. 2-(2) | S-5 | 650 | 119 | 0.20 | 97 | 122 | 117 |
| 2-7 | Inv. 2-(2) | S-9 | 651 | 120 | 0.20 | 98 | 119 | 118 |
| 2-8 | Inv. 2-(1) | S-3 | 627 | 98 | 0.22 | 96 | 129 | 126 |
| 2-9 | Inv. 2-(3) | S-3 | 647 | 101 | 0.28 | 96 | 131 | 124 |
| 2-10 | Inv. 2-(6) | S-3 | 623 | 122 | 0.21 | 94 | 128 | 124 |
| 2-11 | Inv. 2-(10) | S-3 | 590 | 131 | 0.15 | 87 | 127 | 122 |
| 2-12 | Inv. 2-(16) | S-3 | 625 | 105 | 0.18 | 96 | 127 | 124 |
| 2-13 | Inv. 2-(28) | S-3 | 610 | 121 | 0.19 | 98 | 129 | 125 |
| 2-14 | Inv. 2-(35) | S-3 | 645 | 115 | 0.23 | 98 | 130 | 128 |
| 2-15 | Inv. 2-(41) | S-3 | 611 | 98 | 0.16 | 96 | 127 | 125 |
| 2-16 | Inv. 2-(43) | S-3 | 632 | 97 | 0.20 | 96 | 131 | 129 |
| 2-17 | Inv. 2-(44) | S-3 | 627 | 108 | 0.15 | 94 | 129 | 126 |
| 2-18 | Inv. 2-(55) | S-3 | 597 | 115 | 0.11 | 96 | 127 | 124 |
| 2-19 | Inv. 2-(58) | S-3 | 638 | 158 | 0.20 | 95 | 126 | 124 |
| 2-20 | Inv. 2-(64) | S-3 | 630 | 175 | 0.48 | 92 | 125 | 124 |
| 2-21 | Inv. 2-(68) | S-3 | 639 | 160 | 0.31 | 97 | 129 | 126 |

As is obvious from Table 2-1, it is found that every sample having the couplers of the invention has excellent color reproducibility, because their half band widths are narrower, irregular absorptions are less and the percentages of residual dyes are higher, as compared with those of the samples having the comparative couplers, It is further found that the examples of the invention are desirable embidiments, because a sensitivity lowering caused by aging coating liquids can be improved when using the spectral sensitizing dyes preferably applicable to the invention in combination.

In addition, FIG. 2-1 shows the fact that the couplers of the invention are relatively less in undesirable irregular absorption caused in green region (of 550 nm) and relatively sharp in absorption in the regions around λmax, as compared with the conventional phenol type couplers.

EXAMPLE 2-2

A red light-sensitive silver halide emulsion was prepared in the same amnner as in Example 2-1, except that the couplers and spectral sensitizing dyes used in Example 2-1 were replaced by those shown in Table 2-2 when preparing.

Samples No. 2-22 through No. 2-29 of red-sensitive color reversal photographic light-sensitive materials were prepared by coating the following layers over to a triacetyl cellulose film support, in order from the support side.

The amounts of the compounds added are expressed by the amounts thereof per sq. meter unless otherwise specially stated. (Amounts of silver halides are expressed in terms of the contents of silver.)

Layer 1: An emulsion layer

A red-sensitive emulsion layer comprising 1.4 g of gelatin, 0.5 g of red-sensitive silver chlorobromide emulsion and the couplers shown in Table 2-2 dissolved in 0.24 g of dibutyl phthalate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

| (Reversal processing steps) | | |
| --- | --- | --- |
| Step | Time | Temperature |
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| (Primary developer) | |
| --- | --- |
| Water | 700 ml |
| Sodium tetrapolyphosphate | 2 g |
| Sodium sulfite | 20 g |
| Hyroquinone. monosulfonate | 30 g |
| Sodium carbonate, monohydrate | 30 g |
| 1-phenyl,4 methyl,4-hydroxymethyl- | |

| | |
|---|---|
| 3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |
| hexasodium nitrilo,N,N,N— | |
| trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer C) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |
| Sodium hydroxide | 3 g |
| Citrazinic acid | 1.5 g |
| N,ethyl-N—(β-methanesulfonamidoethyl)- | |
| 3,methyl-4-aminoaniline,sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediamine- tetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt %) | 5.0 ml |
| Water to be added to make | 1000 ml |

With respect to the samples coated with the primary emulsion layer coating liquid so prepared as to have the aforementioned composition, there obtained each sensitivitiy ratio of the samples coated with the coating liquids which were aged respectively for one hour and for 5 hours in the same manner as in Example 2-1 and, at the same time, there measured the maximum spectral absorption wavelength (λmax) and half band width (W½) of each sample thus processed, in the same manner as in Example 2-1. The results thereof are shown in Table 2-2.

The measurements of transmission densities relating to the Example 2-2 were made with a densitometer, Model KD-7R.

For the relative sensitivity ratio, Sample No. 2-22 containing comparative coupler a and spectral sensitizing dye b, whose coating liquid was allowed to stand for one hour, was regarded as the criterion of 100%.

Spectral sensitizing dye b

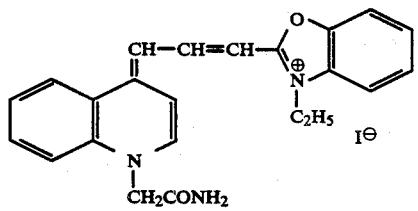

TABLE 2-2

| Sample No. | Coupler used | Spectr. sensi. dye | λ max (nm) | W½ | Dλ 420 | Residual dye (Heat-resist) % | Sensitivity 1-hr | Sensitivity 5-hrs |
|---|---|---|---|---|---|---|---|---|
| 2-22 | Comp. a | b | 650 | 195 | 0.43 | 63 | 100 | 74 |
| 2-23 | Comp. a | S-11 | 651 | 198 | 0.42 | 63 | 114 | 105 |
| 2-24 | Inv. 2-(2) | b | 651 | 102 | 0.24 | 97 | 106 | 82 |
| 2-25 | Inv. 2-(2) | S-11 | 651 | 100 | 0.20 | 99 | 131 | 128 |
| 2-26 | Inv. 2-(35) | S-11 | 643 | 101 | 0.19 | 100 | 129 | 126 |
| 2-27 | Inv. 2-(58) | S-11 | 638 | 142 | 0.21 | 94 | 128 | 126 |
| 2-28 | Inv. 2-(64) | S-11 | 631 | 161 | 0.47 | 94 | 128 | 127 |
| 2-29 | Inv. 2-(68) | S-11 | 637 | 141 | 0.29 | 95 | 129 | 127 |

As is obvious from Table 2-2, it is found that the samples using the couplers of the invention are relatively narrow in half band width and excellent in color reproducibility and that the percentage of residual dye images are remarkably improved as compared to those of the comparative samples.

It is also found that the couplers of the invention are high in sensitivity and excellent in aging stability of coating liquids, provided that the couplers are used together with the spectral sensitizing dyes which may preferably be used in the invention.

EXAMPLE 3-1

Sample 3-1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 0.20 g of dioctyl phthalate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 3-2 through No. 3-24 each of the invention were prepared in quite the same manner as in Example 3-1, except that the comparative coupler a was replaced by the couplers indicated in Table 3-1 (provided that the amounts added were the same molar amounts as in the comparative coupler a).

The resulted Samples No. 3-1 through No. 3-24 were exposed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—($\beta$-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediaminetetraacetate. dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to thus processed Samples No. 3-1 through No. 3-13, the measurements were made respectively each of the maximum spectral absorption wavelengths ($\lambda$max), the reflection densities of 420 nm (D$\lambda$420) when the reflection densities of $\lambda$max were 1.0, and the half band widths (W$\frac{1}{2}$) which are the difference between one point on the longer wavelength side than each $\lambda$max and the shorter wavelength side than each $\lambda$max when the reflection densities of $\lambda$max were 0.5. After then, the spectral absorption characteristics and the color reproducibility of each Sample were examined.

The smaller a value of D$\lambda$420 is, the less an irregular absorption in green region is. The smaller a value of W$\frac{1}{2}$ is, the sharper an absorption is. The facts mean that a color reproducibility is excellent.

Figures 1, 3:
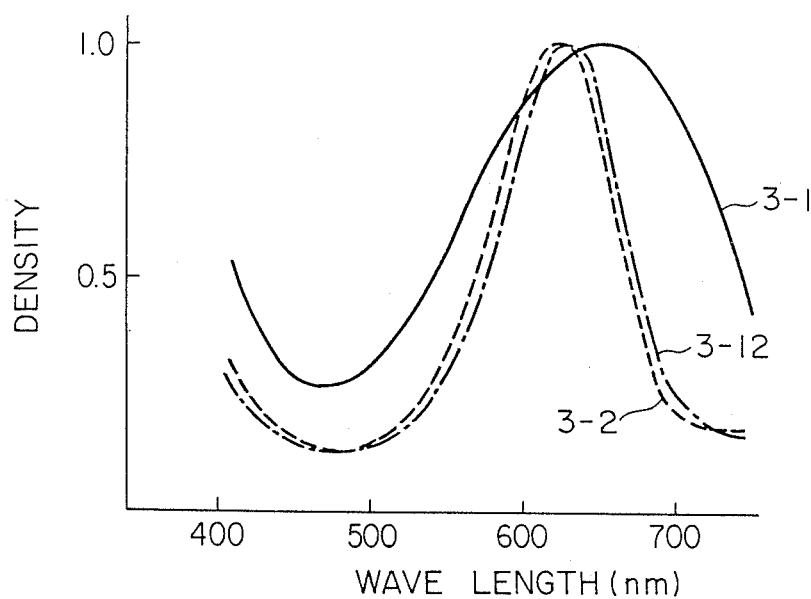

FIG. 3-1 shows the absorption spectra of Sample Nos. 3-1, 3-2 and 3-12.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 3-1, wherein the heat and moisture resisting properties of the dye-images are indicated by the percentage of the residual dyes which still remained after the heat and moisture resistance tests were tried, to the initial density of 1.0.

For those measurements, a densitometer, Model KD-7R (manufactured by Konishiroku Photo Ind. Co., Ltd.), was used.

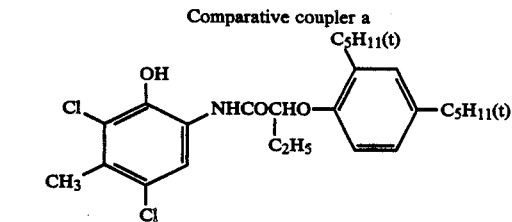

Comparative coupler a

TABLE 3-1

| Sample No. | Coupler used | $\lambda$ max (nm) | W$\frac{1}{2}$ | D$\lambda$ 420 | Residual dye (%) |
|---|---|---|---|---|---|
| 3-1 | Comp. a | 650 | 208 | 0.47 | 62 |
| 3-2 | Inv. II-3-2 | 620 | 97 | 0.24 | 100 |
| 3-3 | Inv. II-3-3 | 610 | 98 | 0.18 | 98 |
| 3-4 | Inv. II-3-4 | 631 | 98 | 0.21 | 98 |
| 3-5 | Inv. II-3-9 | 611 | 100 | 0.18 | 99 |
| 3-6 | Inv. II-3-10 | 600 | 98 | 0.12 | 97 |
| 3-7 | Inv. II-3-12 | 609 | 98 | 0.21 | 100 |
| 3-8 | Inv. II-3-14 | 614 | 100 | 0.17 | 98 |
| 3-9 | Inv. II-3-21 | 601 | 103 | 0.18 | 99 |
| 3-10 | Inv. III-3-2 | 628 | 101 | 0.24 | 100 |
| 3-11 | Inv. III-3-3 | 630 | 98 | 0.21 | 100 |
| 3-12 | Inv. III-3-4 | 628 | 96 | 0.22 | 99 |
| 3-13 | Inv. III-3-7 | 617 | 100 | 0.18 | 99 |
| 3-14 | Inv. III-3-8 | 632 | 96 | 0.25 | 100 |
| 3-15 | Inv. III-3-11 | 617 | 98 | 0.22 | 98 |
| 3-16 | Inv. III-3-13 | 607 | 102 | 0.22 | 97 |
| 3-17 | Inv. III-3-15 | 620 | 100 | 0.24 | 99 |
| 3-18 | Inv. III-3-17 | 610 | 97 | 0.21 | 98 |
| 3-19 | Inv. III-3-20 | 606 | 99 | 0.15 | 98 |
| 3-20 | Inv. IV-3-2 | 621 | 129 | 0.22 | 95 |
| 3-21 | Inv. IV-3-4 | 613 | 121 | 0.20 | 94 |
| 3-22 | Inv. IV-3-7 | 600 | 127 | 0.17 | 95 |
| 3-23 | Inv. V-3-1 | 610 | 140 | 0.21 | 92 |
| 3-24 | Inv. VI-3-1 | 605 | 146 | 0.31 | 97 |

As is obvious from Table 3-1, it is found that every sample having the couplers of the invention has excellent spectral absorption characteristics, because their half band widths are extremely narrower and the irregular absorptions are relatively less, as compared with the sample used the comparative coupler. It is further found that every sample having the couplers of the invention is relatively solid, because of the high percentage of residual dyes and the relatively excellent moisture resisting property.

In addition, FIG. 3-1 shows the fact that the couplers of the invention are relatively less in undesirable irregular absorption caused in green region and relatively sharp in absorption in the regions around $\lambda$max, as compared with the conventional phenol type couplers.

EXAMPLE 3-2

Samples No. 3-25 through No. 3-32 of red-sensitive color reversal photographic light-sensitive materials were prepared by coating the following layers in order from a triacetyl cellulose film support side over to the support.

The amounts of the compounds added are expressed by the amounts thereof per sq. meter unless otherwise specially stated. (Amounts of silver halides are expressed in terms of the contents of silver.)

Layer 1: An emulsion layer

A red-sensitive emulsion layer comprising 1.4 g of gelatin, 0.5 g of red-sensitive silver chlorobromide emulsion (containing silver chloride of 96 mol%) and the couplers shown in Table 3-2 dissolved in 0.24 g of dibutyl phthalate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

(Reversal processing steps)

| Step | Time | Temperature |
|---|---|---|
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An Ordinary temperature |
| Drying | | |

The compositions of the processing liquids were as follows.

| (Primary developer) | |
|---|---|
| Water | 700 ml |
| Sodium tetrapolyphosphate | 2 g |
| Sodium sulfite | 20 g |
| Hydroquinone. monosulfonate | 30 g |
| Sodium carbonate, monohydrate | 30 g |
| 1-phenyl,4 methyl,4-hydroxymethyl-3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |
| hexasodium nitrilo,N,N,N—trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer C) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |
| Sodium hydroxide | 3 g |
| Citrazinic acid | 1.5 g |
| N,ethyl-N—($\beta$-methanesulfonamidoethyl)-3,methyl-4-aminoaniline,sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediamine-tetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt %) | 5.0 ml |
| Water to be added to make | 1000 ml |

With each of the processed samples No. 3-25 through No. 3-32, the maximum spectral absorption wavelength ($\lambda$max) and the half band width ($W_{\frac{1}{2}}$). D$\lambda$420 were measured in the same manner as in Example 3-1. The results thereof are shown in Table 3-2.

TABLE 3-2

| Sample No. | Coupler used | $\lambda$ max (nm) | $W_{\frac{1}{2}}$ | D$\lambda$ 420 | Residual dye (%) |
|---|---|---|---|---|---|
| 3-25 | Comp. a | 651 | 168 | 0.45 | 66 |
| 3-26 | Inv. II-3-1 | 630 | 72 | 0.21 | 99 |
| 3-27 | Inv. II-3-5 | 628 | 75 | 0.23 | 100 |
| 3-28 | Inv. II-3-15 | 612 | 81 | 0.19 | 98 |
| 3-29 | Inv. III-3-6 | 631 | 78 | 0.22 | 99 |
| 3-30 | Inv. III-3-13 | 620 | 81 | 0.19 | 98 |
| 3-31 | Inv. III-3-16 | 627 | 74 | 0.21 | 100 |
| 3-32 | Inv. IV-3-3 | 621 | 107 | 0.25 | 94 |

As is obvious from Table 3-2, it is found that every sample having the couplers of the invention has excellent spectral absorption characteristics and excellent color reproducibility, because their half band widths are extremely narrower and their D$\lambda$420 are also less than those of the sample having the comparative coupler.

It is also found that the samples used the couplers of the invention were remarkably improved in the percentage of the residual dye-images and were also relatively solid.

EXAMPLE 4-1

Sample 4-1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 1.50 g of trioctyl phosphate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 4-2 through No. 4-9 each of the invention were prepared in quite the same manner as in Example 4-1, except that the comparative coupler a was replaced by the couplers indicated in Table 4-1 (provided that the amounts added were the same molar amounts as in the comparative coupler a).

The resulted Samples No. 4-1 through No. 4-9 were exposed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium choride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—($\beta$-metanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediamine-tetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to each processed Sample, the measurements were made respectively each of the maximum spectral absorption wavelengths ($\lambda$max), the reflection densities of 420 nm (D$\lambda$420) when the reflection densities of $\lambda$max were 1.0, and the half band widths (W$\frac{1}{2}$) which are the difference between the reflection density 0.5 on the side of the wavelength longer than $\lambda$max and the reflection density of 0.5 on the side of the wavelength shorter than $\lambda$max). After then, the spectral absorption characteristics and the color reproducibility of each sample were examined.

The smaller a value of D$\lambda$420 is, the less an irregular absorption in green region is. The smaller a value of W$\frac{1}{2}$ is, the sharper an absorption is. The facts mean that a color reproducibility is excellent.

Figures 1, 4:
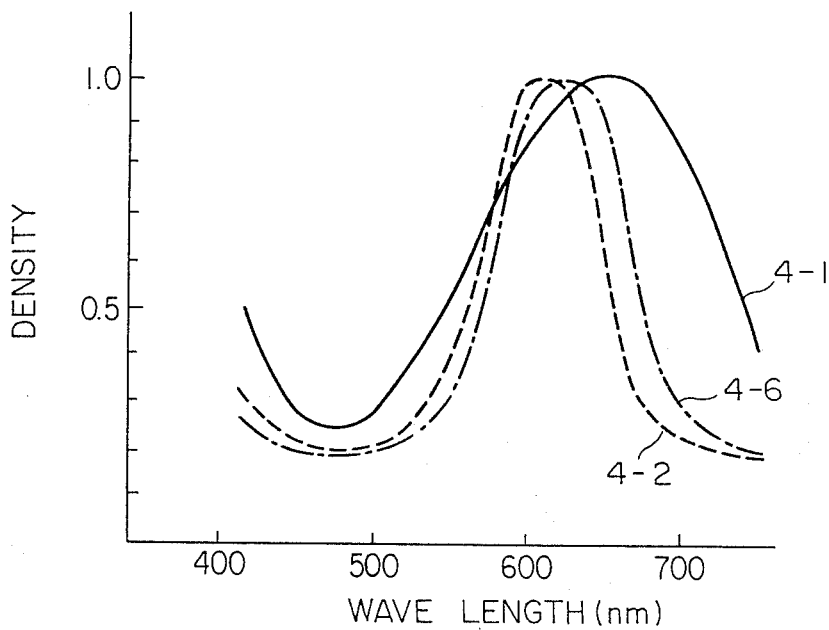

FIG. 4-1 shows the absorption spectra of Sample Nos. 4-1, 4-2 and 4-6.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 4-1, wherein the heat and moisture resisting properties of the dye-images are indicated by the percentage of the residual dyes which still remained after the heat and moisture resistance tests were tried, to the initial density of 1.0.

For those measurements, a densitometer, Model KD-7R (manufactured by Konishiroku Photo Ind. Co., Ltd.), was used.

The results thereof are correctively shown in Table 4-1.

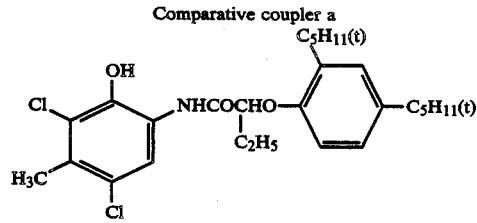

Comparative coupler a

TABLE 1

| Sample No. | Coupler used | $\lambda$ max (nm) | W$\frac{1}{2}$ | D$\lambda$ 420 | Residual dye (%) |
|---|---|---|---|---|---|
| 1 | Comp. a | 650 | 207 | 0.47 | 60 |
| 2 | Inv. 2 | 609 | 97 | 0.29 | 100 |
| 3 | Inv. 5 | 604 | 103 | 0.27 | 100 |
| 4 | Inv. 7 | 610 | 100 | 0.29 | 98 |
| 5 | Inv. 11 | 598 | 94 | 0.15 | 99 |
| 6 | Inv. 17 | 623 | 105 | 0.23 | 98 |
| 7 | Inv. 20 | 602 | 100 | 0.14 | 100 |
| 8 | Inv. 24 | 598 | 95 | 0.24 | 99 |
| 9 | Inv. 26 | 611 | 102 | 0.17 | 98 |

As is obvious from Table 4-1, it is found that every sample having the couplers of the invention has excellent spectral absorption characteristics, because their half band widths are extremely narrower than those of the sample having the comparative coupler and their irregular absorptions represented by D$\lambda$420 are relatively less, as compared with the sample used the comparative coupler.

It is further found that every sample having the couplers of the invention can provide solid cyan images, because of their high percentage of residual dyes and excellent moisture resisting property.

In addition, FIG. 4-1 shows the fact that the couplers of the invention (e.g., Sample No. 4-2 and No. 4-6) are relatively less in undesirable irregular absorption caused in green region and relatively sharp in absorption in the regions around $\lambda$max, as compared with the conventional phenol type couplers.

EXAMPLE 4-2

Samples No. 4-10 through No. 4-16 of red-sensitive color reversal photographic light-sensitive materials were prepared by coating the following layers in order from the support side over to a triacetyl cellulose film support.

The amounts of the compounds added are expressed by the amounts thereof per sq. meter unless otherwise specially stated. (Amounts of silver halides are expressed in terms of the contents of silver).

Layer 1: An emulsion layer

A red-sensitive emulsion layer comprising 1.4 g of gelatin, 0.5 g of red-sensitive silver chlorobromide emulsion (containing silver chloride of 96 mol%) and the couplers ($9.1 \times 10^{-4}$ moles) shown in Table 4-2 dissolved in 1.65 g of dioctyl phosphate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

(Reversal processing steps)

| Step | Time | Temperature |
|---|---|---|
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| (Primary developer) | |
|---|---|
| Water | 700 ml |
| Sodium tetrapolyphosphate | 2 g |
| Sodium sulfite | 20 g |
| Hydroquinone. monosulfonate | 30 g |
| Sodium carbonate, monohydrate | 30 g |
| 1-phenyl.4 methyl.4-hydroxymethyl-3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |
| hexasodium nitrilo.N.N.N-trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |
| Sodium hydroxide | 3 g |
| Citrazinic acid | 1.5 g |
| N.ethyl-N—($\beta$-methanesulfonamidoethyl)-3.methyl-4-aminoaniline.sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediamine-tetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt %) | 5.0 ml |
| Konidux (manufactured by Konishiroku Photo Industry Co. Ltd.) | 5.0 ml |
| Water to be added to make | 1000 ml |

With each of the processed samples, the maximum spectral absorption wavelength ($\lambda$max), the half band width ($W\frac{1}{2}$) and $D\lambda 420$ were measured in the same manner as in Example 4-1. The results thereof are shown in Table 4-2.

The measurements of transmission densities relating to the Example 4-2 were made with a densitometer, Model KD-7R.

TABLE 4-2

| Sample No. | Coupler used | $\lambda$ max (nm) | $W\frac{1}{2}$ | $D\lambda$ 420 | Residual dye (%) |
|---|---|---|---|---|---|
| 4-10 | Comp. a | 649 | 165 | 0.44 | 61 |
| 4-11 | Inv. II-4-3 | 629 | 91 | 0.21 | 97 |
| 4-12 | Inv. II-4-9 | 588 | 78 | 0.12 | 99 |
| 4-13 | Inv. II-4-13 | 619 | 90 | 0.20 | 100 |
| 4-14 | Inv. II-4-15 | 601 | 82 | 0.15 | 99 |
| 4-15 | Inv. II-4-21 | 598 | 85 | 0.25 | 98 |
| 4-16 | Inv. II-4-22 | 608 | 93 | 0.16 | 96 |

As is obvious from Table 4-2, it is found that every eample having the couplers of the invention has excellent spectral absorption characteristics, because their half band widths are extremely narrower and their $D\lambda 420$ are also less than those of the sample having the comparative coupler. They can accordingly provide cyan images having excellent color reproducibility.

They can also provide solid cyan images, because their percentage of residual dyes is extremely high in heat resisting test.

[Dispersion stability tests]

A dispersion was prepared in the following manner.

Comparative cyan coupler b of $2 \times 10^{-3}$ moles, 3.0 g of dioctyl phthalate and 3 g of ethyle acetate were mixed and heated up to 60° C. The resulted solution was mixed with 17 ml of an aqueous 5% gelatin solution containing 1.7 ml of an aqueous solution of Alkanol B (i.e., alkylnaphthalene sulfonate, manufactured by DuPont). The resulted mixture solution was emulsified and dispersed by means of a supersonic homogenizer.

From the resulted dispersion, ethyl acetate was distilled off under reduced pressure, so that dispersion sample 4-1 was prepared. For the purpose of observing the dispersion stability of cyan couplers, the dispersion was stored in a refrigerator (at 5° C.) for six days and was then put in a warm water bath at 40° C. to keep temperature. The conditions of each crystal deposition were observed by an optical microscope, immediately after, 6 hours after and 12 hours after keeping temperature, respectively.

Further, dispersion samples No. 4-2 through No. 4-5 were prepared by making use of the couplers shown in Table 4-3 in the same manner as in Sample 4-1, and the dispersion stability of the couplers were also checked up. The results thereof are shown in Table 4-3.

Comparative coupler b

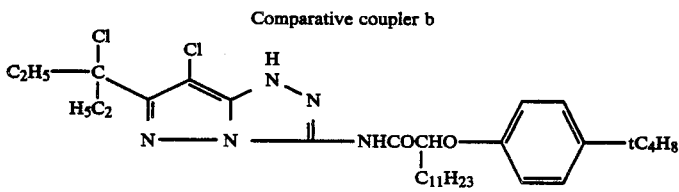

TABLE 4-3

| Dispersion sample No. | Coupler used | deposition* | | |
|---|---|---|---|---|
| | | Immediate | 6 hours | 12 hours |
| 4-1 | Comp. b | Δ | Δ | X |
| 4-2 | II-4-1 | O | O | Δ |
| 4-3 | II-4-10 | O | O | O |
| 4-4 | II-4-12 | O | O | Δ |
| 4-5 | II-4-23 | O | O | O |

*In Table 4-3, the depositions were evaluated in the following manner.
O: Not deposited.
Δ: Partly deposited, but no problem for practical use.
X: Deposited and problematic for practical use.

As is obvious from Table 4-3, it is found that, when using the cyan couplers of the invention are used, dispersions having excellent dispersion stability can be obtained, because deposition is hardly produced as compared to those produced with comparative coupler b.

EXAMPLE 5-1

Sample 5-1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 0.20 g of dioctyl phthalate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 5-2 through No. 5-9 each of the invention were prepared in quite the same manner as in Example 5-1 except that comparative coupler a was replaced by the couplers of the invention (5-2), (5-9), (5-21), (5-25), (5-26), (5-39), (5-42) and (5-45), respectively, (provided that the amounts added are as shown in Table 5-1).

The resulted Samples No. 5-1 through No. 5-9 were exposed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in the steps are given below.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediaminetetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to thus processed Samples No. 5-1 through No. 5-9, the measurements were made respectively each of the maximum spectral absorption wavelengths (λmax) and both of the reflection densities of 550 nm and 700 nm (Dλ550 and Dλ700)) at the time when the respective reflection densities of λmax were 1.0.

The smaller a value of Dλ550 is, the less an irregular absorption in green region is. The smaller a value of Dλ700 is, the sharper an absorption is. The facts mean that a color reproducibility is excellent.

Figures 1, 5:
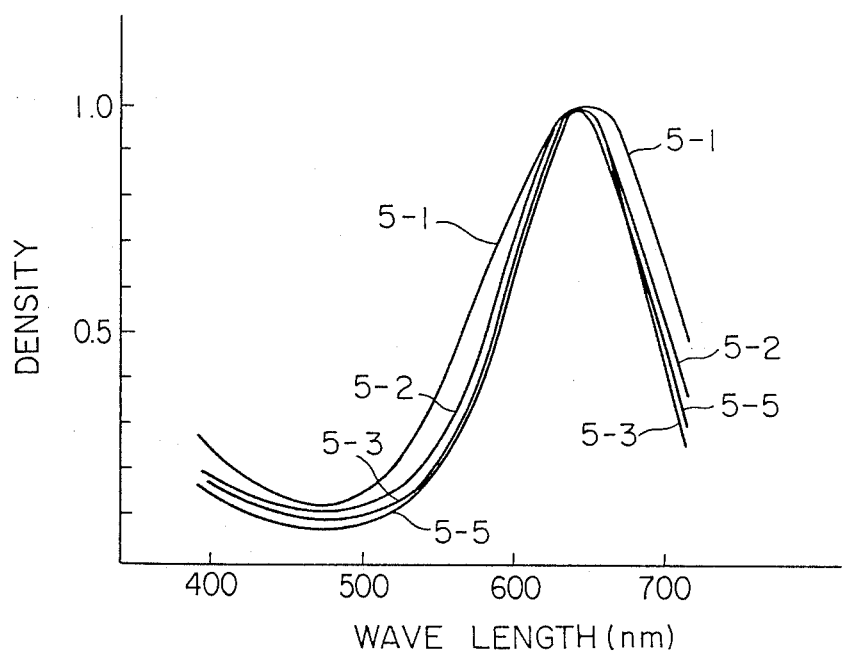

FIG. 5-1 shows the absorption spectra of Sample Nos. 5-1, 5-2, 5-3 and 5-5.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 5-1, wherein the heat and moisture resisting properties of the dye-images are indicated by the percentage of the residual dyes which still remained after the heat and moisture resistance tests were tried, to the initial density of 1.0.

For those measurements, a densitometer, Model KD-7R (manufactured by Konishiroku Photo Ind. Co., Ltd.), was used.

Comparative coupler a

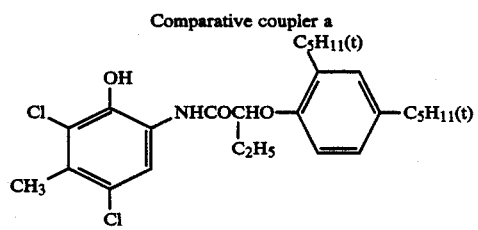

TABLE 5-1

| Sample No. | Coupler used | Amt. added g/m² | Dλ 550 | Dλ 700 | λ max. (nm) | Residual dye (%) |
|---|---|---|---|---|---|---|
| 5-1 (Comp) | Comp. a | 0.45 | 0.34 | 0.68 | 652 | 60 |
| 5-2 (Inv) | Inv. 5-2 | 0.46 | 0.23 | 0.55 | 629 | 97 |
| 5-3 (Inv) | Inv. 5-9 | 0.63 | 0.20 | 0.42 | 647 | 100 |
| 5-4 (Inv) | Inv. 5-21 | 0.49 | 0.22 | 0.40 | 638 | 96 |
| 5-5 (Inv) | Inv. 5-25 | 0.63 | 0.20 | 0.45 | 649 | 94 |
| 5-6 (Inv) | Inv. 5-26 | 0.65 | 0.19 | 0.45 | 645 | 98 |
| 5-7 (Inv) | Inv. 5-39 | 0.58 | 0.22 | 0.39 | 632 | 99 |
| 5-8 (Inv) | Inv. 5-42 | 0.60 | 0.27 | 0.39 | 620 | 95 |
| 5-9 (Inv) | Inv. 5-45 | 0.44 | 0.24 | 0.37 | 619 | 96 |

It is found from Table 5-1 that Samples No. 5-2 through No. 5-9 used the couplers of the invention are less in both Dλ550 and Dλ700 and excellent in color reproducibility. Among them, Couplers (5-9), (5-21), (5-25) and (5-26) are particularly excellent from the viewpoint of λmax. It is also found that the percentage of residual dye-images of the samples of the invention are remarkably improved as compared to those of the comparative samples and that color fading hardly occurs even when they are put in the circumstances of high temperature and humid.

FIG. 5-1 indicates that the couplers of the invention are relatively less in undesirable absorption in green spectral region and sharp in absorption caused around λmax.

EXAMPLE 6-1

Sample 6-1 of red-sensitive color light-sensitive material was prepared by coating the following layers over to a paper support laminated with polyethylene on the both sides thereof in order from the support side, respectively. The amounts of the compounds added are expressed in terms of those added per sq. meter, unless otherwise particularly stated. (Amounts of silver halides are expressed in terms of the contents of silver.)

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 1.05 g of dioctyl phthalate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 6-2 through No. 6-11 each of the invention were prepared in quite the same manner as in Example 6-1, except that comparative coupler a was replaced by the couplers shown in Table 6-1 (provided that the amounts added were the same molar amounts as in comparative coupler (a).

The resulted Samples No. 6-1 through No. 6-11 were exposed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| (Color developer) | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediaminetetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to thus processed Samples No. 6-1 through No. 6-11, the measurements were made respectively each of the maximum spectral absorption wavelengths (λmax), the reflection densities of 420 nm (Dλ420) when the reflection densities of λmax were 1.0, and the half band widths (W½) which are the difference between one point on the longer wavelength side than each λmax and the shorter wavelength side than each λmax when the reflection densities of λmax were 0.5. After then, the spectral absorption characteristics and the color reproducibility of each Sample were examined.

The smaller a value of Dλ420 is, the less an irregular absorption in green region is. The smaller a value of W½ is, the sharper an absorption is. The facts mean that a color reproducibility is excellent.

Figures 1, 6:
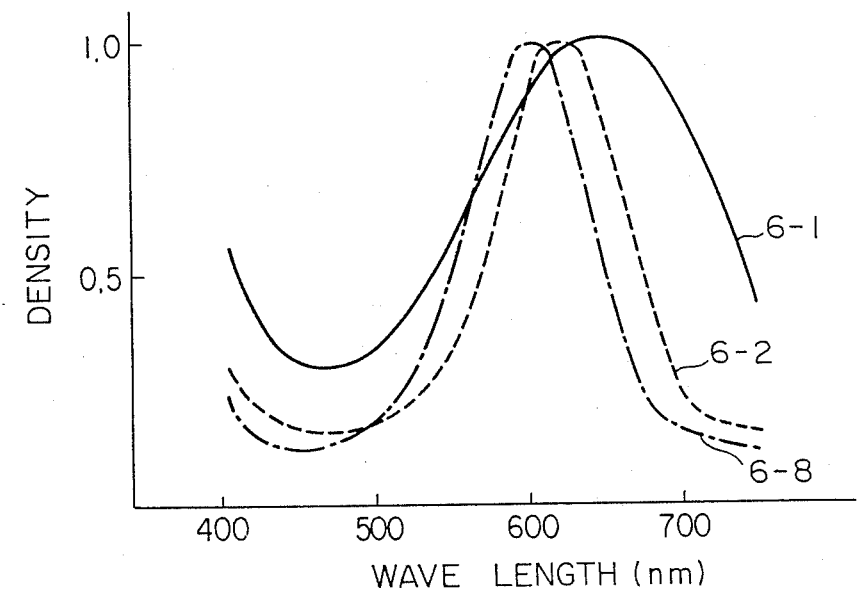

FIG. 6-1 shows the absorption spectra of Sample Nos. 6-1, 6-2 and 6-8.

Further, each of the processed samples was allowed to stand for 14 days under the circumstances of a high temperature and humidity (at 60° C. and 80% RH), and the heat and moisture resisting properties of the resulted dye-images were checked up. The results thereof are also shown in Table 6-1, wherein the heat and moisture resisting properties of the dye-images are indicated by the percentage of the residual dyes which still remained after the heat and moisture resistance tests were tried, to the initial density of 1.0.

For those measurements, a densitometer, Model KD-7R (manufactured by Konishiroku Photo Ind. Co., Ltd.), was used.

Comparative coupler a

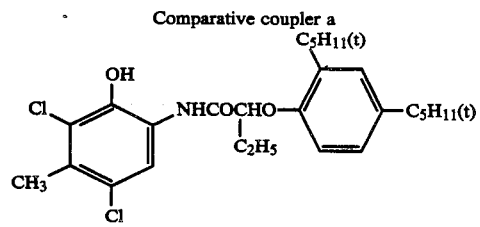

TABLE 6-1

| Sample No. | Coupler used | λ max (nm) | W½ | Dλ 420 | Residual dye (%) |
|---|---|---|---|---|---|
| 6-1 | Comp. a | 649 | 205 | 0.48 | 58 |
| 6-2 | Inv. II-6-3 | 618 | 112 | 0.21 | 99 |
| 6-3 | Inv. II-6-4 | 607 | 100 | 0.16 | 100 |
| 6-4 | Inv. II-6-6 | 622 | 102 | 0.23 | 99 |
| 6-5 | Inv. II-6-10 | 612 | 108 | 0.17 | 98 |
| 6-6 | Inv. II-6-12 | 603 | 115 | 0.14 | 96 |
| 6-7 | Inv. II-6-14 | 587 | 92 | 0.12 | 99 |
| 6-8 | Inv. II-6-16 | 600 | 103 | 0.15 | 100 |
| 6-9 | Inv. II-6-18 | 598 | 98 | 0.15 | 98 |
| 6-10 | Inv. II-6-20 | 604 | 105 | 0.14 | 97 |
| 6-11 | Inv. II-6-25 | 593 | 96 | 0.12 | 99 |

As is obvious from Table 6-1, it is found that every sample having the couplers of the invention has excellent spectral absorption characteristics, because their half band widths are extremely narrower and their irregular absorptions are also less, as compared with those of the sample having the comparative coupler.

It is also found that the Samples using the couplers of the invention are relatively solid, because the percentage of the residual dye-images was remarkably improved and the heat- and moisture-resisting properties are excellent.

In addition, FIG. 6-1 shows the fact that the couplers (II-6-2, II-6-8) of the invention are relatively less in undesirable irregular absorption caused in green region and relatively sharp in absorption in the regions around λmax, as compared with the conventional phenol type coupler (1).

EXAMPLE 6-2

A red-sensitive color reversal potographic light-sensitive materials No. 6-12 through No. 6-16 were prepared by coating the following layers in order from a triacetyl cellulose film support over to the support.

The amounts of the compounds added are expressed by the amounts thereof per sq. meter unless otherwise specially stated. (Amounts of silver halides are expressed in terms of the contents of silver).

Layer 1: An emulsion layer

A red-sensitive emulsion layer comprising 1.4 g of gelatin, 0.5 g of red-sensitive silver chlorobromide emulsion and the couplers ($9.1 \times 10^{-4}$ moles) shown in Table 6-2 dissolved in 1.25 g of dibutyl phthalate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

| (Reversal processing steps) | | |
|---|---|---|
| Step | Time | Temperature |
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| (Primary developer) | |
|---|---|
| Water | 700 ml |
| Sodium tetrapolyphosphate | 2 g |
| Sodium sulfite | 20 g |
| Hydroquinone. monosulfonate | 30 g |
| Sodium carbonate, monohydrate | 30 g |
| 1-phenyl.4 methyl.4-hydroxymethyl-3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |
| hexasodium nitrilo.N.N.N—trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer C) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |

-continued

| | |
|---|---|
| Sodium hydroxide | 3 g |
| Citrazinic acid | 1.5 g |
| N.ethyl-N—(β-methanesulfonamidoethyl)-3.methyl-4-aminoaniline.sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediamine-tetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt %) | 5.0 ml |
| Konidux (manufactured by Konishiroku Photoindustry Co. LTD.) | 5.0 ml |
| Water to be added to make | 1000 ml |

With each of the processed samples No. 6-12 through No. 6-16, the maximum spectral absorption wavelength (λmax) and the half band width (W½), Dλ420 were measure in the same manner as in Example 6-1. The results thereof are shown in Table 6-2.

The measurements of transmission densities relating to the Example 6-2 were made with a densitometer, Model KD-7R.

TABLE 6-2

| Sample No. | Coupler used | λmax (nm) | W½ | Dλ 420 | Residual dye (%) |
|---|---|---|---|---|---|
| 6-12 | Comp. a | 650 | 169 | 0.43 | 60 |
| 6-13 | Inv. II-6-2 | 607 | 88 | 0.16 | 98 |
| 6-14 | Inv. II-6-8 | 619 | 97 | 0.20 | 100 |
| 6-15 | Inv. II-6-17 | 607 | 91 | 0.16 | 99 |
| 6-16 | Inv. II-6-27 | 587 | 85 | 0.12 | 99 |

As is obvious from Table 6-2, it is found that every sample having the couplers of the invention has excellent spectral absorption characteristics and excellent color reproducibility, because their half band widths are extremely narrower and their Dλ420 are also less, as compared with those of the sample having the comparative coupler.

It is also found that the samples used the couplers of the invention were remarkably improved in the percentage of the residual dye-images and were also relatively solid.

EXAMPLE 7-1

Sample 7-1 of red-sensitive color light-sensitive material was prepared by coating the following layers over to a paper support laminated with polyethylene on the both sides thereof in order from the support side, resectively. The amounts of the compounds added are expressed in terms of those added per sq. meter, unless otherwise particularly stated. (Amounts of silver halides are expressed in terms of the contents of silver).

Layer 1: An emulsion layer

A red-sensitive emulsion layer comprising 1.2 g of gelatin, 0.30 g of red-sensitive silver chlorobromide emulsion (containing silver chloride of 96 mol%) and 0.45 g of comparative cyan coupler a dissolved in 1.50 g of trioctyl phosphate.

Layer 2: A protective layer

A protective layer containing 0.50 g of gelatin, whereto 2,4-dichloro-6-hydroxy-s-triazine sodium salt was added as a hardener in an amount of 0.017 g per g of the gelatin used.

Next, Samples No. 7-2 through No. 7-20 each of the invention were prepared in quite the same manner as in Example 7-1, except that the comparative coupler a was replaced by the couplers of the invention indicated in Table 7-1 (provided that the amounts added were the same molar amounts as in Sample 7-1).

The resulted Samples No. 7-1 through No. 7-20 were exposed to light through a wedge in an ordinary method and were then processed in the following processing steps.

| (Processing steps) | | |
|---|---|---|
| Developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

The processing liquids used in each of the steps were as follows.

| | |
|---|---|
| (Color developer) | |
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N—ethyl-N—(β-methanesulfonamidoethyl) aniline sulfate | 5.5 g |
| Optical brightening agent (a 4,4'-diaminostilbene disulfonic acid derivative) | 1.0 g |
| Potassium hydroxide | 2.0 g |
| Water to be added to make | 1 liter |
| pH to be adjusted to | pH 10.20 |
| (Bleach-fixer) | |
| Ferric ammonium ethylenediamine-tetraacetate, dihydrate | 60 g |
| Ethylenediaminetetraacetic acid | 3 g |
| Ammonium thiosulfate (a 70% solution) | 100 ml |
| Ammonium sulfite (a 40% solution) | 27.5 ml |
| pH to be adjusted with potassium carbonate or glacial acetic acid to | pH 7.1 |
| Water to be added to make | 1 liter |
| (Stabilizer) | |
| 5-chloro-2-methyl-4-isothiazoline-3-one | 1.0 g |
| Ethylene glycol | 10 g |
| Water to be added to make | 1 liter |

With respect to each sample thus processed, the measurements were made respectively each of the maximum spectral absorption wavelengths (λmax) when the reflection densities of λmax were 1.0, and the reflection densities of 420 nm and the half band widths of spectral absorption (i.e., W½) which are the difference between the wavelength of reflection density 0.5 on the side of a wavelength longer than that of λmax and the wavelength of reflection density 0.5 on the side of a wavelength shorter than that of λmax.)

The smaller a value of Dλ420 is, the less an irregular absorption in blue region is. The smaller a value of half band width is, the sharper an absorption is. The facts mean that a color reproducibility is excellent.

Figures 1, 7:
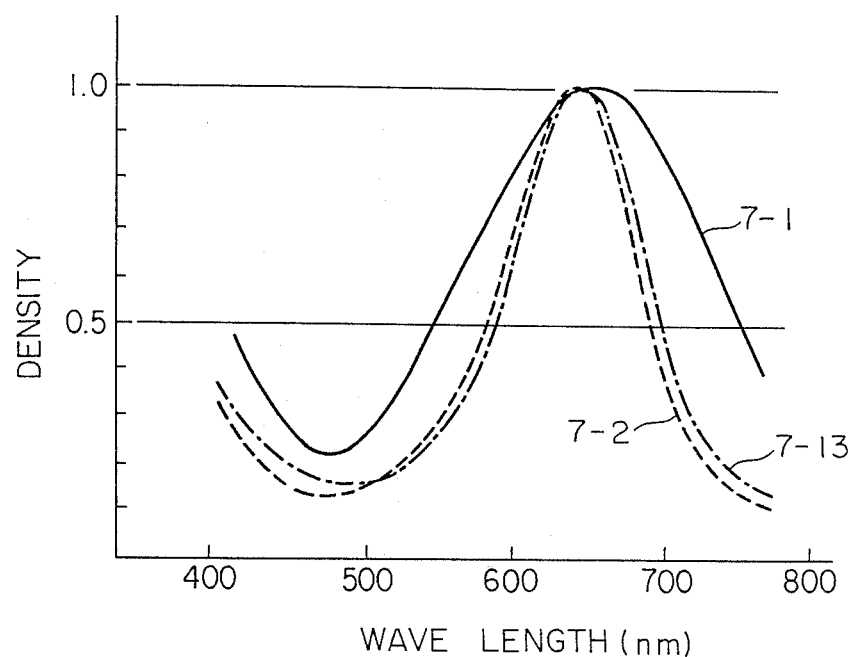

FIG. 7–1 shows the absorption spectra of Sample Nos. 7–1, 7–2 and 7–13.

Further, each of the processed samples was allowed to stand for 14 days under the circumstances of a high temperature and humidity (at 60° C. and 80%RH), and the heat and moisture resisting properties of the resulted dye-images were checked up. The results thereof are also shown in Table 7–1, wherein the heat and moisture resisting properties of the dye-images are indicated by the percentage of the residual dyes to the initial density of 1.0 after testing the heat and moisture resistance.

For these measurements, a densitometer, Model KD-7R (manufactured by Konishiroku Photo Ind. Co., Ltd.), was used.

The results thereof are collectively shown in Table 7–1.

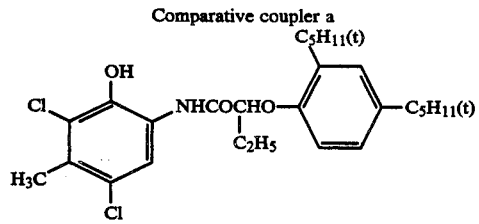

Comparative coupler a

TABLE 7-1

| Sample No. | Coupler used | λ max (nm) | W½ | Dλ 420 | Residual dye (%) |
|---|---|---|---|---|---|
| 7-1 | Comp. a | 652 | 219 | 0.46 | 56 |
| 7-2 | Inv. II-7-2 | 635 | 96 | 0.25 | 100 |
| 7-3 | Inv. II-7-4 | 627 | 109 | 0.21 | 98 |
| 7-4 | Inv. II-7-5 | 640 | 90 | 0.28 | 99 |
| 7-5 | Inv. II-7-10 | 620 | 110 | 0.17 | 94 |
| 7-6 | Inv. II-7-15 | 627 | 100 | 0.20 | 97 |
| 7-7 | Inv. II-7-25 | 637 | 101 | 0.25 | 98 |
| 7-8 | Inv. II-7-27 | 626 | 94 | 0.27 | 98 |
| 7-9 | Inv. III-7-2 | 630 | 102 | 0.28 | 98 |
| 7-10 | Inv. III-7-3 | 635 | 94 | 0.27 | 95 |
| 7-11 | Inv. III-7-5 | 627 | 102 | 0.19 | 97 |
| 7-12 | Inv. III-7-6 | 628 | 112 | 0.20 | 97 |
| 7-13 | Inv. III-7-10 | 642 | 98 | 0.29 | 99 |
| 7-14 | Inv. III-7-14 | 626 | 104 | 0.21 | 100 |
| 7-15 | Inv. III-7-23 | 630 | 94 | 0.26 | 99 |
| 7-16 | Inv. IV-7-3 | 610 | 138 | 0.20 | 93 |
| 7-17 | Inv. IV-7-4 | 619 | 130 | 0.24 | 92 |
| 7-18 | Inv. IV-7-8 | 637 | 135 | 0.29 | 92 |
| 7-19 | Inv. VI-7-2 | 612 | 158 | 0.38 | 92 |
| 7-20 | Inv. V-7-1 | 617 | 162 | 0.58 | 95 |

As is obvious from the results shown in Table 7–1, it is found that every sample having the couplers of the invention has extremely excellent color reproducibility, because their half band widths (W½) are narrower and the irregular absorptions detectable by λmax are also less, as compared with the sample used the comparative coupler. Further, the samples of the invention can provide excellently color-reproduced cyan images as compared with the comparative samples, because their spectral waveforms are excellent, the λmax value thereof are small though.

Still further, it is found that the samples having the couplers of the invention are also high in dye-residual percentage and excellent in heat- and moisture-resistance, as compared with the comparative samples.

In addition, FIG. 7–1 shows the fact that the couplers of the invention are relatively less in undesirable irregular absorption caused in green region e.g., 550 nm) and relatively sharp in absorption in the regions around λmax, as compared with the conventional phenol type couplers.

EXAMPLE 7-2

Samples No. 7–21 through No. 7–29 of red-sensitive color reversal photographic light-sensitive materials were prepared by coating the following layers over to a triacetyl cellulose film support, in order from the support side.

The amounts of the compounds added are expressed by the amounts thereof per sq. meter unless otherwise specially stated. (Amounts of silver halides are expressed in terms of the contents of silver.)

Layer 1: An emulsion layer

A red-sensitive emulsion layer comprising 1.4 g of gelatin, 0.5 g of red-sensitive silver chlorobromide emulsion (containing silver chloride of 96 mol%) and the couplers ($9.1 \times 10^{-4}$ moles) shown in Table 7–2 dissolved in 1.65 g of dioctylphenyl phosphate.

Layer 2: A protective layer

A protective layer containing 0.5 g of gelatin, whereto 2,4-dichloro-6-hydroxy-s-triazine sodium salt was added as a hardener in an amount of 0.017 g per g of the gelatin used.

The resulted Samples were exposed to light through a wedge in an ordinary method and were then processed in the following processing steps.

| (Reversal processing steps) | | |
|---|---|---|
| Step | Time | Temperature |
| Primary developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | An ordinary temperature |
| Drying | | |

The compositions of the processing liquids were as follows.

| (Primary developer) | |
|---|---|
| Water | 700 ml |
| Sodium tetrapolyphosphate | 2 g |
| Sodium sulfite | 20 g |
| Hydroquinone. monosulfonate | 30 g |
| Sodium carbonate, monohydrate | 30 g |
| 1-phenyl.4 methyl.4-hydroxymethyl-3 pyrazolidone | 2 g |
| Potassium bromide | 2.5 g |
| Potassium thiocyanate | 1.2 g |
| Potassium iodide (in a 0.1% solution) | 2 ml |
| Water to be added to make | 1000 ml |
| pH to be adjusted to | pH 10.1 |
| (Reversal bath) | |
| Water | 700 ml |

| | |
|---|---|
| hexasodium nitrilo.N.N.N—trimethylene phosphanate | 3 g |
| Stannous chloride, dihydrate | 1 g |
| p-aminophenol | 0.1 g |
| Sodium hydroxide | 5 g |
| Glacial acetic acid | 15 ml |
| Water to be added to make | 1000 ml |
| (Color developer C) | |
| Water | 700 ml |
| Sodium tetrapolyphosphate | 2 g |
| Sodium sulfite | 7 g |
| Sodium tertiary phosphate, dodecahydrate | 36 g |
| Potassium bromide | 1 g |
| Potassium iodide (in a 0.1% solution) | 90 ml |
| Sodium hydroxide | 3 g |
| Citrazinic acid | 1.5 g |
| N.ethyl-N—(β-methanesulfonamidoethyl)-3.methyl-4-aminoaniline.sulfate | 11 g |
| Ethylenediamine | 3 g |
| Water to be added to make | 1000 ml |
| (Adjuster) | |
| Water | 700 ml |
| Sodium sulfite | 12 g |
| Sodium ethylenediaminetetraacetate, dihydrate | 8 g |
| Thioglycerol | 0.4 ml |
| Glacial acetic acid | 3 ml |
| Water to be added to make | 1000 ml |
| (Bleaching bath) | |
| Water | 500 ml |
| Sodium ethylenediaminetetraacetate, dihydrate | 2.0 g |
| Ferriammonium ethylenediamine-tetraacetate, dihydrate | 120.0 g |
| Potassium bromide | 100.0 g |
| Water to be added to make | 1000 ml |
| (Fixer) | |
| Water | 800 ml |
| Ammonium thiosulfate | 80.0 g |
| Sodium sulfite | 5.0 g |
| Sodium hydrogensulfite | 5.0 g |
| Water to be added to make | 1000 ml |
| (Stabilizer) | |
| Water | 800 ml |
| Formalin (at 37 wt %) | 5.0 ml |
| Water to be added to make | 1000 ml |

With each of the processed samples, the maximum spectral absorption wavelength (λmax) and the half band width (W½) were measured in the same manner as in Example 7-1. The results thereof are shown in Table 7-2.

The measurements of transmission densities relating to the Example 7-2 were made with a densitometer, Model KD-7R.

TABLE 7-2

| sample No. | Coupler used | λ max (nm) | W½ | Dλ 420 | Residual dye (%) (Heat-resistance) |
|---|---|---|---|---|---|
| 7-21 | Comp. a | 653 | 150 | 0.42 | 65 |
| 7-22 | Inv. II-7-2 | 636 | 62 | 0.24 | 99 |
| 7-23 | Inv. II-7-3 | 627 | 67 | 0.22 | 97 |
| 7-24 | Inv. II-7-7 | 631 | 71 | 0.18 | 93 |
| 7-25 | Inv. III-7-8 | 637 | 71 | 0.27 | 96 |
| 7-26 | Inv. III-7-15 | 629 | 65 | 0.20 | 98 |
| 7-27 | Inv. IV-7-6 | 630 | 98 | 0.24 | 94 |
| 7-28 | Inv. VI-7-4 | 620 | 101 | 0.38 | 92 |
| 7-29 | Inv. V-7-3 | 612 | 109 | 0.50 | 96 |

As is obvious from Table 7-2, it is found that every sample having the couplers of the invention has remarkably excellent color reproducibility, because their half band widths are narrower and their irregular absorptions are also less, as compared with the comparative couplers.

It is also found that the samples used the couplers of the invention were high in the percentage of the residual dye-images and excellent in heat- and moisture-resistance.

What is claimed is:

1. A light-sensitive silver halide color photographic material comprising a support and, provided thereon, a red light-sensitive silver halide emulsion layer containing a pyrazoloazole type cyan dye-forming coupler having at least one electron attractive group at a substitutable position except the active site of the coupler for coupling reaction.

2. The light-sensitive silver halide color photographic material of claim 1 wherein a cyan dye produced from the cyan dye-forming coupler has a maximum spectral absorption wavelength between 580 nm to 710 nm.

3. The light-sensitive silver halide color photographic material of claim 2, wherein a cyan dye produced from the cyan dye-forming coupler has a maximum spectral absorption wavelength between 600 nm to 700 nm.

4. The light-sensitive silver halide color photographic material of claim 1, wherein said cyan dye-forming coupler is represented by Formula [I]-1;

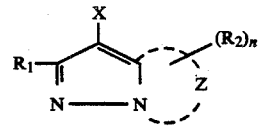

Formula [I]-1 wherein $R_1$ is a hydrogen atom or a substituent, $R_2$ is a hydrogen atom or a substituent provided that at least one of $R_1$ and $R_2$ (at least one of $R_2$s when there are more than 2 $R_2$s) is an electron attractive group; Z represents a group of non-metal atoms necessary to complete a nitrogen-containing heterocyclic ring; $R_2$ being connected with a carbon atom of said heterocyclic ring; X represents a hydrogen atom or a substituent capable of being split off upon reaction with the oxidized product of a color developing agent; and n is an integer of 1 or 2.

5. The light-sensitive silver halide color photographic material of claim 4, wherein said $R_1$ is an electron attractive group.

6. The light-sensitive silver halide color photographic material of claim 5, wherein said electron attractive group is selected from the group consisting of a sulfonyl group, a sulfinyl group, a sulfonyloxy group, a sulfonylmethyl group, a sulfamoyl group, a phosphoryl group, a tetrazolyl group, a pyrrolyl group, a halogenated alkoxy group, a halogenated aryloxy group, an acyl group, a halogen group, a nitro group and a carboxy group.

7. The light-sensitive silver halide color photographic material of claim 1, wherein said cyan dye-forming coupler is represented by Formula [I]-4;

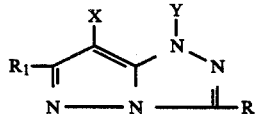

Formula [I]-4 wherein $R_1$ is selected from the group consisting of a cyano group, an acyloxy group, an oxycarbonyl group or a carbamoyl group; $R_2$ and Y independently represent a hydrogen atom or a substituent; and X represents a hydrogen atom or a group capable of beeing split off upon reaction with the oxidized product of a color developing agent.

8. The light-sensitive silver halide color photograhic material of claim 4, wherein at least one of said $R_2$ is an electron attractive group.

9. The light-sensitive silver halide color photographic material of claim 1, wherein said cyan dye-forming coupler is represented by Formula [I]-6;

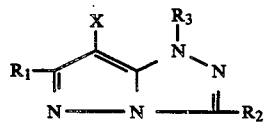

Formula [I]-6 wherein $R_2$ represents a substituent selected from the group consisting of a sulfonyl group, a sulfonyloxy group, a sulfinyl group, a sulfamoyl group, a phosphoryl group, a tetrazolyl group, a pyrrolyl group, a halogenated alkoxy group, a halogenated aryloxy group, a halogen atom, a cyano group, a nitro group, an acyl group and a carbamoyl group; $R_1$ and $R_3$ independently represent a hydrogen atom or a substituent; and X represents a hydrogen atom or a group capable of being split off upon reaction with the oxidized product of a color developing agent.

10. The light-sensitive silver halide color photographic material of claim 4, wherein at least two of said $R_1$ and $R_2$ (s) are electron attractive groups.

11. The light-sensitive silver halide color photographic material of claim 1, wherein said red light-sensitive emulsion layer contains a spectral sensitizing dye selected from the group consisting of ones represented by formulas [A], [B], [C], [D], [E] and [F]:

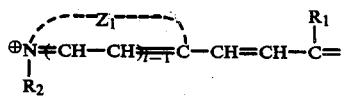
Formula [A]

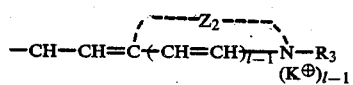
[B]

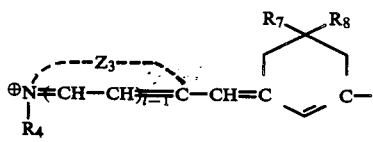

-continued

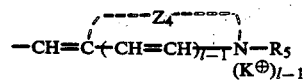

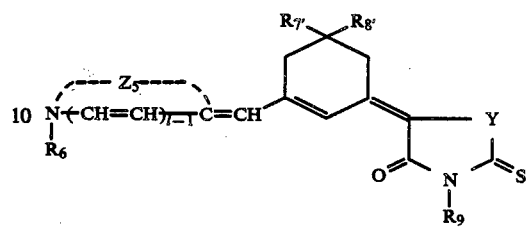
[C]

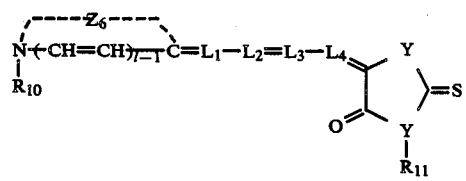
[D]

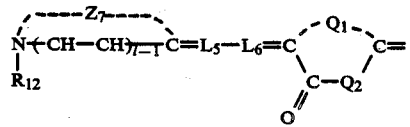
[E]

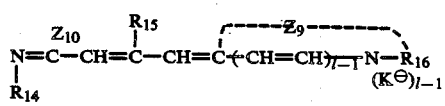
[F]

wherein $Z_1$ through $Z_9$ each represent a group of atoms necessary for completing a benzene ring or a naphthalene ring condensed with a pyridine ring, an imidazole ring, a thiazole ring, a selenazole ring, an oxazole ring or a tetrazole ring; $Z_{10}$ represents a group of atoms necessary for completing a benzothiazole ring, a benzoselenazole ring a β-naphthothiazole ring a β-naphthoselenazole ring, a benzimidazole ring or a 2-quinoline ring; $Q_1$ and $Q_2$ each represent a group of atoms necessary for associatively completeing a nucleus of 4-thiazolidinone, 5-thiazolidinone or 4-imidazolidinone; $R_1$ and $R_{15}$ each represent a hydrogen atom, an alkyl group or an aryl group; $R_7$, $R_8$, $R'_7$ and $R'_8$, each represent an alkyl group; $R_9$ and $R_{11}$ each represent an alkyl group, an aryl group or a heterocyclic group; $R_2$, $R_3$, $R_4$, $R_5$, $R_6$, $R_{10}$, $R_{12}$, $R_{13}$, $R_{14}$ and $R_{16}$ each represent an alkyl group or an aryl group;

l is an integer of 1 or 2; Y represents a sulfur atom or selenium atom; $L_1$ through $L_6$ each represent a substituted or nonsubstituted methine group; and K represents an acid anion.

* * * * *

UNITED STATES PATENT AND TRADEMARK OFFICE
CERTIFICATE OF CORRECTION

PATENT NO. : 4,873,183

DATED : October 10, 1989

INVENTOR(S) : Kimie Tachibana et al

It is certified that error appears in the above-identified patent and that said Letters Patent is hereby corrected as shown below:

Claim 11, column 204, line 44, "ring" (2nd occurrence) should be followed by --,--.

Claim 11, column 204, line 45, "ring" (1st occurrence) should be followed by --,--.

Claim 11, column 204, line 51, change "R $_8$" (2nd occurrence) to --R'$_8$--.

Claim 11, column 204, line 56, change "1" to --$\ell$--.

Signed and Sealed this

Tenth Day of March, 1992

Attest:

HARRY F. MANBECK, JR.

*Attesting Officer*      *Commissioner of Patents and Trademarks*